United States Patent
Aranyi et al.

(10) Patent No.: US 10,349,950 B2
(45) Date of Patent: Jul. 16, 2019

(54) APPARATUS FOR APPLYING SURGICAL CLIPS

(71) Applicant: Covidien LP, Mansfield, MA (US)

(72) Inventors: Ernest Aranyi, Easton, CT (US); Kenneth H. Whitfield, North Haven, CT (US); Greg Sorrentino, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 278 days.

(21) Appl. No.: 15/606,020

(22) Filed: May 26, 2017

(65) Prior Publication Data

US 2017/0258472 A1   Sep. 14, 2017

Related U.S. Application Data

(63) Continuation of application No. 14/551,546, filed on Nov. 24, 2014, now Pat. No. 9,687,247, which is a continuation of application No. 11/245,866, filed on Oct. 7, 2005, now Pat. No. 8,920,438.

(60) Provisional application No. 60/617,017, filed on Oct. 8, 2004.

(51) Int. Cl.
| | |
|---|---|
| *A61B 17/128* | (2006.01) |
| *A61B 17/12* | (2006.01) |
| *A61B 17/00* | (2006.01) |
| *A61B 17/28* | (2006.01) |

(52) U.S. Cl.
CPC ......... *A61B 17/1285* (2013.01); *A61B 17/12* (2013.01); *A61B 17/128* (2013.01); *A61B 2017/00407* (2013.01); *A61B 2017/12004* (2013.01); *A61B 2017/2837* (2013.01)

(58) Field of Classification Search
CPC ... A61B 17/12; A61B 17/128; A61B 17/1285; A61B 2017/2837; A61B 2017/00407; A61B 2017/12004
See application file for complete search history.

(56) References Cited

U.S. PATENT DOCUMENTS

| | | |
|---|---|---|
| 3,120,230 A | 2/1964 | Skold |
| 3,363,628 A | 1/1968 | Wood |
| 3,638,847 A | 2/1972 | Noiles et al. |
| (Continued) | | |

FOREIGN PATENT DOCUMENTS

| | | |
|---|---|---|
| AU | 2010200641 A1 | 10/2010 |
| AU | 2013254887 A1 | 11/2013 |
| (Continued) | | |

OTHER PUBLICATIONS

Chinese First Office Action corresponding to Chinese Appln. No. CN 201410076318.8 dated Jan. 23, 2017.

(Continued)

*Primary Examiner* — Phong Son H Dang

(57) ABSTRACT

A clip applying apparatus is described for applying clips seriatim to tissue. The apparatus includes a lockout member for limiting distal movement of the camming member after the proximal-most clip has been applied to tissue. In one embodiment, the apparatus includes a jaw locking member for preventing approximation of the jaw members of the apparatus. In one embodiment, a latch assembly is provided to releasably engage a clip pusher of the apparatus to the camming member of the apparatus.

10 Claims, 32 Drawing Sheets

(56) References Cited

U.S. PATENT DOCUMENTS

| | | |
|---|---|---|
| 3,675,688 A | 7/1972 | Bryan et al. |
| 3,735,762 A | 5/1973 | Bryan et al. |
| 3,867,944 A | 2/1975 | Samuels |
| 4,242,902 A | 1/1981 | Green |
| 4,296,751 A | 10/1981 | Blake, III et al. |
| 4,372,316 A | 2/1983 | Blake, III et al. |
| 4,408,603 A | 10/1983 | Blake, III et al. |
| 4,412,539 A | 11/1983 | Jarvik |
| 4,418,694 A | 12/1983 | Beroff et al. |
| 4,430,997 A | 2/1984 | DiGiovanni et al. |
| 4,449,531 A | 5/1984 | Cerwin et al. |
| 4,471,780 A | 9/1984 | Menges et al. |
| 4,478,220 A | 10/1984 | Di Giovanni et al. |
| 4,480,640 A | 11/1984 | Becht |
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,592,498 A | 6/1986 | Braun et al. |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,796,625 A | 1/1989 | Kees, Jr. |
| 4,799,481 A | 1/1989 | Transue et al. |
| 4,815,466 A | 3/1989 | Perlin |
| 4,821,721 A | 4/1989 | Chin et al. |
| 4,822,348 A | 4/1989 | Casey |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,931,058 A | 6/1990 | Cooper |
| 4,934,364 A | 6/1990 | Green |
| 4,951,860 A | 8/1990 | Peters et al. |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A * | 7/1991 | Green .................. A61B 17/128 227/901 |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,563 A | 11/1991 | Green et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A * | 3/1993 | Green .................. A61B 17/128 606/139 |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,356,064 A | 10/1994 | Green et al. |
| 5,366,458 A | 11/1994 | Korthoff et al. |
| 5,366,459 A | 11/1994 | Yoon |
| 5,368,600 A | 11/1994 | Failla et al. |
| 5,381,943 A | 1/1995 | Allen et al. |
| 5,382,253 A | 1/1995 | Hogendijk |
| 5,382,254 A | 1/1995 | McGarry et al. |
| 5,382,255 A | 1/1995 | Castro et al. |
| 5,383,880 A | 1/1995 | Hooven |
| 5,383,881 A | 1/1995 | Green et al. |
| 5,395,375 A | 3/1995 | Turkel et al. |
| 5,395,381 A | 3/1995 | Green et al. |

(56) References Cited

U.S. PATENT DOCUMENTS

| | | |
|---|---|---|
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,499 A | 1/1996 | Sorrentino et al. |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,587 A | 5/1997 | Bishop et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,662 A | 9/1997 | Bishop et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,697,942 A | 12/1997 | Palti |
| 5,700,270 A * | 12/1997 | Peyser .............. A61B 17/1285 606/142 |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,749,881 A | 5/1998 | Sackier et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A * | 6/1998 | Cuny ................ A61B 17/1285 227/901 |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,279 A | 10/1998 | Hughett et al. |
| 5,827,306 A | 10/1998 | Yoon |
| 5,827,323 A | 10/1998 | Klieman et al. |
| 5,833,695 A | 11/1998 | Yoon |
| 5,833,696 A * | 11/1998 | Whitfield ............ A61B 17/1285 606/143 |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,906,625 A | 5/1999 | Bito et al. |
| 5,913,862 A | 6/1999 | Ramsey et al. |
| 5,913,876 A | 6/1999 | Taylor et al. |
| 5,918,791 A | 7/1999 | Sorrentino et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A * | 8/1999 | Peyser ................ A61B 17/1285 606/142 |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,009,551 A | 12/1999 | Sheynblat |
| 6,017,358 A | 1/2000 | Yoon et al. |
| 6,053,908 A | 4/2000 | Crainich et al. |
| RE36,720 E | 5/2000 | Green et al. |
| 6,059,799 A * | 5/2000 | Aranyi ................ A61B 17/1285 606/143 |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |

(56) References Cited

U.S. PATENT DOCUMENTS

| | | |
|---|---|---|
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan et al. |
| 6,546,935 B2 | 4/2003 | Hooven |
| 6,551,333 B2 | 4/2003 | Kuhns et al. |
| 6,562,051 B1 | 5/2003 | Bolduc et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,656,193 B2 | 12/2003 | Grant et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,743,240 B2 | 6/2004 | Smith et al. |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,682 B1 | 5/2005 | McClellan et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,052,504 B2 | 5/2006 | Hughett |
| 7,056,330 B2 | 6/2006 | Gayton |
| 7,108,703 B2 | 9/2006 | Danitz et al. |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,232,445 B2 | 6/2007 | Kortenbach et al. |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,316,693 B2 | 1/2008 | Viola |
| 7,316,696 B2 | 1/2008 | Wilson, Jr. et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,431,724 B2 * | 10/2008 | Manetakis ......... A61B 17/1285 606/139 |
| 7,510,562 B2 | 3/2009 | Lindsay |
| 7,552,853 B2 | 6/2009 | Mas et al. |
| 7,637,917 B2 | 12/2009 | Whitfield et al. |
| 7,644,848 B2 | 1/2010 | Swayze |
| 7,686,820 B2 | 3/2010 | Huitema et al. |
| 7,695,482 B2 | 4/2010 | Viola |
| 7,717,926 B2 | 5/2010 | Whitfield et al. |
| 7,727,248 B2 | 6/2010 | Smith et al. |
| 7,731,724 B2 | 6/2010 | Huitema et al. |
| 7,740,641 B2 | 6/2010 | Huitema |
| 7,752,853 B2 | 7/2010 | Singh et al. |
| 7,753,250 B2 | 7/2010 | Clauson et al. |
| 7,766,207 B2 | 8/2010 | Mather et al. |
| 7,819,886 B2 | 10/2010 | Whitfield et al. |
| 7,887,553 B2 | 2/2011 | Lehman et al. |
| 7,905,890 B2 | 3/2011 | Whitfield et al. |
| 7,942,885 B2 | 5/2011 | Sixto, Jr. et al. |
| 7,952,060 B2 | 5/2011 | Watanabe et al. |
| 7,963,433 B2 | 6/2011 | Whitman et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,178 B2 | 9/2011 | Olson et al. |
| 8,021,375 B2 | 9/2011 | Aldrich et al. |
| 8,021,378 B2 | 9/2011 | Sixto, Jr. et al. |
| 8,038,686 B2 | 10/2011 | Huitema et al. |
| 8,056,565 B2 | 11/2011 | Zergiebel |
| 8,062,310 B2 | 11/2011 | Shibata et al. |
| 8,066,720 B2 | 11/2011 | Knodel et al. |
| 8,066,721 B2 | 11/2011 | Kortenbach et al. |
| 8,066,722 B2 | 11/2011 | Miyagi et al. |
| 8,070,760 B2 | 12/2011 | Fujita |
| 8,075,571 B2 | 12/2011 | Vitali et al. |

(56) References Cited

U.S. PATENT DOCUMENTS

| | | |
|---|---|---|
| 8,080,021 B2 | 12/2011 | Griego |
| 8,083,668 B2 | 12/2011 | Durgin et al. |
| 8,088,061 B2 | 1/2012 | Wells et al. |
| 8,091,755 B2 | 1/2012 | Kayan et al. |
| 8,100,926 B1 | 1/2012 | Filshie et al. |
| 8,128,643 B2 | 3/2012 | Aranyi et al. |
| 8,133,240 B2 | 3/2012 | Damarati |
| 8,142,451 B2 | 3/2012 | Boulnois et al. |
| 8,157,145 B2 | 4/2012 | Shelton, IV et al. |
| 8,157,149 B2 | 4/2012 | Olson et al. |
| 8,157,151 B2 | 4/2012 | Ingmanson et al. |
| 8,172,859 B2 | 5/2012 | Matsuno et al. |
| 8,172,870 B2 | 5/2012 | Shipp |
| 8,187,290 B2 | 5/2012 | Buckman et al. |
| 8,211,120 B2 | 7/2012 | Itoh |
| 8,211,124 B2 | 7/2012 | Ainsworth et al. |
| 8,216,255 B2 | 7/2012 | Smith et al. |
| 8,216,257 B2 | 7/2012 | Huitema et al. |
| 8,236,012 B2 | 8/2012 | Molitor et al. |
| 8,246,634 B2 | 8/2012 | Huitema et al. |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino et al. |
| 8,267,945 B2 | 9/2012 | Nguyen et al. |
| 8,267,946 B2 | 9/2012 | Whitfield et al. |
| 8,272,554 B2 | 9/2012 | Whitman et al. |
| 8,282,655 B2 | 10/2012 | Whitfield et al. |
| 8,308,743 B2 | 11/2012 | Matsuno et al. |
| 8,328,822 B2 | 12/2012 | Huitema et al. |
| 8,336,556 B2 | 12/2012 | Zergiebel |
| 8,348,130 B2 | 1/2013 | Shah et al. |
| 8,357,171 B2 | 1/2013 | Whitfield et al. |
| 8,366,709 B2 | 2/2013 | Schechter et al. |
| 8,366,726 B2 | 2/2013 | Dennis |
| 8,371,491 B2 | 2/2013 | Huitema et al. |
| 8,372,095 B2 | 2/2013 | Viola |
| 8,382,773 B2 | 2/2013 | Whitfield et al. |
| 8,398,655 B2 | 3/2013 | Cheng et al. |
| 8,403,945 B2 | 3/2013 | Whitfield et al. |
| 8,403,946 B2 | 3/2013 | Whitfield et al. |
| 8,408,442 B2 | 4/2013 | Racenet et al. |
| 8,409,222 B2 | 4/2013 | Whitfield et al. |
| 8,409,223 B2 | 4/2013 | Sorrentino et al. |
| 8,419,752 B2 | 4/2013 | Sorrentino et al. |
| 8,430,892 B2 | 4/2013 | Bindra et al. |
| 8,444,660 B2 | 5/2013 | Adams et al. |
| 8,465,460 B2 | 6/2013 | Yodfat et al. |
| 8,465,502 B2 | 6/2013 | Zergiebel |
| 8,475,473 B2 | 7/2013 | Vandenbroek et al. |
| 8,480,688 B2 | 7/2013 | Boulnois et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,506,580 B2 | 8/2013 | Zergiebel et al. |
| 8,512,357 B2 | 8/2013 | Viola |
| 8,518,055 B1 | 8/2013 | Cardinale et al. |
| 8,523,882 B2 | 9/2013 | Huitema et al. |
| 8,529,585 B2 | 9/2013 | Jacobs et al. |
| 8,529,586 B2 | 9/2013 | Rosenberg et al. |
| 8,529,588 B2 | 9/2013 | Ahlberg et al. |
| 8,545,486 B2 | 10/2013 | Malkowski |
| 8,556,920 B2 | 10/2013 | Huitema et al. |
| 8,568,430 B2 | 10/2013 | Shipp |
| 8,579,918 B2 | 11/2013 | Whitfield et al. |
| 8,585,717 B2 | 11/2013 | Sorrentino et al. |
| 8,603,109 B2 | 12/2013 | Aranyi et al. |
| 8,652,151 B2 | 2/2014 | Lehman et al. |
| 8,652,152 B2 | 2/2014 | Aranyi et al. |
| 8,663,247 B2 | 3/2014 | Menn et al. |
| 8,685,048 B2 | 4/2014 | Adams et al. |
| 8,690,899 B2 | 4/2014 | Kogiso et al. |
| 8,708,213 B2 | 4/2014 | Shelton, IV et al. |
| 8,709,027 B2 | 4/2014 | Adams et al. |
| 8,715,299 B2 | 5/2014 | Menn et al. |
| 8,720,766 B2 | 5/2014 | Hess et al. |
| 8,734,469 B2 | 5/2014 | Pribanic et al. |
| 8,747,423 B2 | 6/2014 | Whitfield et al. |
| 8,753,356 B2 | 6/2014 | Vitali et al. |
| 8,814,884 B2 | 8/2014 | Whitfield et al. |
| 8,821,516 B2 | 9/2014 | Huitema |
| 8,839,954 B2 | 9/2014 | Disch |
| 8,845,659 B2 | 9/2014 | Whitfield et al. |
| 8,894,665 B2 | 11/2014 | Sorrentino et al. |
| 8,894,666 B2 | 11/2014 | Schulz et al. |
| 8,900,253 B2 | 12/2014 | Aranyi et al. |
| 8,915,930 B2 | 12/2014 | Huitema et al. |
| 8,920,438 B2 | 12/2014 | Aranyi et al. |
| 8,939,974 B2 | 1/2015 | Boudreaux et al. |
| 8,950,646 B2 | 2/2015 | Viola |
| 8,961,542 B2 | 2/2015 | Whitfield et al. |
| 8,968,337 B2 | 3/2015 | Whitfield et al. |
| 8,968,342 B2 | 3/2015 | Wingardner, III et al. |
| 8,973,804 B2 | 3/2015 | Hess et al. |
| 9,011,464 B2 | 4/2015 | Zammataro |
| 9,011,465 B2 | 4/2015 | Whitfield et al. |
| 9,089,334 B2 | 7/2015 | Sorrentino et al. |
| 9,113,892 B2 | 8/2015 | Malkowski et al. |
| 9,113,893 B2 | 8/2015 | Sorrentino et al. |
| 9,119,629 B2 | 9/2015 | Cardinale et al. |
| 9,186,136 B2 | 11/2015 | Malkowski et al. |
| 9,186,153 B2 | 11/2015 | Zammataro |
| 9,208,429 B2 | 12/2015 | Thornton et al. |
| 9,220,507 B1 | 12/2015 | Patel et al. |
| 9,282,961 B2 | 3/2016 | Whitman et al. |
| 9,326,776 B2 | 5/2016 | Gadberry et al. |
| 9,358,011 B2 | 6/2016 | Sorrentino et al. |
| 9,358,015 B2 | 6/2016 | Sorrentino et al. |
| 9,364,216 B2 | 6/2016 | Rockrohr et al. |
| 9,364,239 B2 | 6/2016 | Malkowski |
| 9,364,240 B2 | 6/2016 | Whitfield et al. |
| 9,370,400 B2 | 6/2016 | Parihar |
| 9,393,024 B2 | 7/2016 | Whitfield et al. |
| 9,398,917 B2 | 7/2016 | Whitfield et al. |
| 9,408,610 B2 | 8/2016 | Hartoumbekis |
| 9,414,844 B2 | 8/2016 | Zergiebel et al. |
| 9,433,411 B2 | 9/2016 | Racenet et al. |
| 9,439,654 B2 | 9/2016 | Sorrentino et al. |
| 9,480,477 B2 | 11/2016 | Aranyi et al. |
| 9,498,227 B2 | 11/2016 | Zergiebel et al. |
| 9,526,501 B2 | 12/2016 | Malkowski |
| 9,532,787 B2 | 1/2017 | Zammataro |
| 9,545,254 B2 | 1/2017 | Sorrentino et al. |
| 9,549,741 B2 | 1/2017 | Zergiebel |
| 9,642,627 B2 | 5/2017 | Zammataro |
| 9,687,247 B2 | 6/2017 | Aranyi et al. |
| 9,717,505 B2 | 8/2017 | Whitfield et al. |
| 9,737,310 B2 | 8/2017 | Whitfield et al. |
| 9,750,500 B2 | 9/2017 | Malkowski |
| 9,763,668 B2 | 9/2017 | Whitfield et al. |
| 9,775,623 B2 | 10/2017 | Zammataro et al. |
| 9,775,624 B2 | 10/2017 | Rockrohr et al. |
| 9,848,886 B2 | 12/2017 | Malkowski et al. |
| 9,855,043 B2 | 1/2018 | Malkowski |
| 9,931,124 B2 | 4/2018 | Gokharu |
| 9,968,361 B2 | 5/2018 | Aranyi et al. |
| 9,968,362 B2 | 5/2018 | Malkowski et al. |
| 10,004,502 B2 | 6/2018 | Malkowski et al. |
| 10,159,484 B2 | 12/2018 | Sorrentino et al. |
| 10,159,491 B2 | 12/2018 | Gokharu |
| 10,159,492 B2 | 12/2018 | Zammataro |
| 10,166,027 B2 | 1/2019 | Aranyi et al. |
| 2001/0047178 A1 | 11/2001 | Peters |
| 2002/0040226 A1 | 4/2002 | Laufer et al. |
| 2002/0068947 A1 | 6/2002 | Kuhns et al. |
| 2002/0082618 A1 | 6/2002 | Shipp et al. |
| 2002/0087169 A1 | 7/2002 | Brock et al. |
| 2002/0087170 A1 | 7/2002 | Kuhns et al. |
| 2002/0099388 A1 | 7/2002 | Mayenberger |
| 2002/0120279 A1 | 8/2002 | Deguillebon et al. |
| 2002/0128668 A1* | 9/2002 | Manetakis ......... A61B 17/1285 606/143 |
| 2002/0177859 A1 | 11/2002 | Monassevitch et al. |
| 2002/0198537 A1 | 12/2002 | Smith et al. |

(56) References Cited

U.S. PATENT DOCUMENTS

| | | |
|---|---|---|
| 2002/0198538 A1 | 12/2002 | Kortenbach et al. |
| 2002/0198539 A1 | 12/2002 | Sixto et al. |
| 2002/0198540 A1 | 12/2002 | Smith et al. |
| 2002/0198541 A1 | 12/2002 | Smith et al. |
| 2003/0014060 A1 | 1/2003 | Wilson et al. |
| 2003/0018345 A1 | 1/2003 | Green |
| 2003/0023249 A1 | 1/2003 | Manetakis |
| 2003/0040759 A1 | 2/2003 | de Guillebon et al. |
| 2003/0105476 A1 | 6/2003 | Sancoff et al. |
| 2003/0114867 A1 | 6/2003 | Bolduc et al. |
| 2003/0135224 A1 | 7/2003 | Blake |
| 2003/0167063 A1 | 9/2003 | Kerr |
| 2003/0208231 A1 | 11/2003 | Williamson et al. |
| 2003/0220657 A1 | 11/2003 | Adams |
| 2003/0225423 A1 | 12/2003 | Huitema |
| 2003/0229360 A1 | 12/2003 | Gayton |
| 2003/0233105 A1 | 12/2003 | Gayton |
| 2004/0010272 A1 | 1/2004 | Manetakis et al. |
| 2004/0044352 A1 | 3/2004 | Fowler et al. |
| 2004/0097970 A1 | 5/2004 | Hughett |
| 2004/0097971 A1 | 5/2004 | Hughett |
| 2004/0097972 A1 | 5/2004 | Shipp et al. |
| 2004/0106936 A1 | 6/2004 | Shipp et al. |
| 2004/0133215 A1 | 7/2004 | Baxter |
| 2004/0138681 A1 | 7/2004 | Pier |
| 2004/0153100 A1 | 8/2004 | Ahlberg et al. |
| 2004/0158266 A1 | 8/2004 | Damarati |
| 2004/0162567 A9 | 8/2004 | Adams |
| 2004/0167545 A1 | 8/2004 | Sadler et al. |
| 2004/0176776 A1 | 9/2004 | Zubok et al. |
| 2004/0176783 A1 | 9/2004 | Edoga et al. |
| 2004/0176784 A1 | 9/2004 | Okada |
| 2004/0193213 A1 | 9/2004 | Aranyi et al. |
| 2004/0232197 A1 | 11/2004 | Shelton et al. |
| 2005/0010242 A1 | 1/2005 | Lindsay |
| 2005/0080440 A1 | 4/2005 | Durgin et al. |
| 2005/0090837 A1 | 4/2005 | Sixto et al. |
| 2005/0090838 A1 | 4/2005 | Sixto et al. |
| 2005/0096670 A1 | 5/2005 | Wellman et al. |
| 2005/0096671 A1 | 5/2005 | Wellman et al. |
| 2005/0096672 A1 | 5/2005 | Manetakis et al. |
| 2005/0101975 A1 | 5/2005 | Nguyen et al. |
| 2005/0107807 A1 | 5/2005 | Nakao |
| 2005/0107809 A1 | 5/2005 | Litscher et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0107871 A1 | 5/2005 | Realyvasquez et al. |
| 2005/0113847 A1 | 5/2005 | Gadberry et al. |
| 2005/0119671 A1 | 6/2005 | Reydel et al. |
| 2005/0119673 A1 | 6/2005 | Gordon et al. |
| 2005/0119677 A1 | 6/2005 | Shipp |
| 2005/0125010 A1 | 6/2005 | Smith et al. |
| 2005/0143767 A1 | 6/2005 | Kimura et al. |
| 2005/0149063 A1 | 7/2005 | Young et al. |
| 2005/0149064 A1 | 7/2005 | Peterson et al. |
| 2005/0149068 A1 | 7/2005 | Williams et al. |
| 2005/0149069 A1 | 7/2005 | Bertolero et al. |
| 2005/0165415 A1 | 7/2005 | Wales |
| 2005/0165418 A1 | 7/2005 | Chan |
| 2005/0171560 A1 | 8/2005 | Hughett |
| 2005/0175703 A1 | 8/2005 | Hunter et al. |
| 2005/0177176 A1 | 8/2005 | Gerbi et al. |
| 2005/0203547 A1 | 9/2005 | Weller et al. |
| 2005/0203548 A1 | 9/2005 | Weller et al. |
| 2005/0216036 A1 | 9/2005 | Nakao |
| 2005/0216056 A1 | 9/2005 | Valdevit et al. |
| 2005/0222588 A1 | 10/2005 | Vandenbroek et al. |
| 2005/0222590 A1 | 10/2005 | Gadberry et al. |
| 2005/0222665 A1 | 10/2005 | Aranyi |
| 2005/0228411 A1 | 10/2005 | Manzo |
| 2005/0228416 A1 | 10/2005 | Burbank et al. |
| 2005/0234478 A1 | 10/2005 | Wixey et al. |
| 2005/0251183 A1 | 11/2005 | Buckman et al. |
| 2005/0251184 A1 | 11/2005 | Anderson |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277951 A1 | 12/2005 | Smith et al. |
| 2005/0277952 A1 | 12/2005 | Arp et al. |
| 2005/0277953 A1 | 12/2005 | Francese et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2005/0288690 A1 | 12/2005 | Bourque et al. |
| 2006/0000867 A1 | 1/2006 | Shelton et al. |
| 2006/0004388 A1 | 1/2006 | Whayne et al. |
| 2006/0004390 A1 | 1/2006 | Rosenberg et al. |
| 2006/0009789 A1 | 1/2006 | Gambale et al. |
| 2006/0009790 A1 | 1/2006 | Blake et al. |
| 2006/0009792 A1 | 1/2006 | Baker et al. |
| 2006/0020270 A1 | 1/2006 | Jabba et al. |
| 2006/0020271 A1 | 1/2006 | Stewart et al. |
| 2006/0047305 A1 | 3/2006 | Ortiz et al. |
| 2006/0047306 A1 | 3/2006 | Ortiz et al. |
| 2006/0064117 A1 | 3/2006 | Aranyi et al. |
| 2006/0079115 A1 | 4/2006 | Aranyi et al. |
| 2006/0079913 A1 | 4/2006 | Whitfield et al. |
| 2006/0085015 A1 | 4/2006 | Whitfield et al. |
| 2006/0100649 A1 | 5/2006 | Hart |
| 2006/0111731 A1 | 5/2006 | Manzo |
| 2006/0129170 A1 | 6/2006 | Royce et al. |
| 2006/0135992 A1 | 6/2006 | Bettuchi et al. |
| 2006/0163312 A1 | 7/2006 | Viola et al. |
| 2006/0173470 A1 | 8/2006 | Oray et al. |
| 2006/0178683 A1 | 8/2006 | Shimoji et al. |
| 2006/0184182 A1 | 8/2006 | Aranyi et al. |
| 2006/0190013 A1 | 8/2006 | Menn |
| 2006/0195125 A1 | 8/2006 | Sakakine et al. |
| 2006/0200179 A1 | 9/2006 | Barker et al. |
| 2006/0212050 A1 | 9/2006 | D'Agostino et al. |
| 2006/0217749 A1 | 9/2006 | Wilson et al. |
| 2006/0224165 A1 | 10/2006 | Surti et al. |
| 2006/0224170 A1 | 10/2006 | Duff |
| 2006/0235437 A1 | 10/2006 | Vitali et al. |
| 2006/0235438 A1 | 10/2006 | Huitema et al. |
| 2006/0235439 A1 | 10/2006 | Molitor et al. |
| 2006/0235440 A1 | 10/2006 | Huitema et al. |
| 2006/0235441 A1 | 10/2006 | Huitema et al. |
| 2006/0235442 A1 | 10/2006 | Huitema |
| 2006/0235443 A1 | 10/2006 | Huitema et al. |
| 2006/0235444 A1 | 10/2006 | Huitema et al. |
| 2006/0241655 A1 | 10/2006 | Viola |
| 2006/0259045 A1 | 11/2006 | Damarati |
| 2006/0259049 A1 | 11/2006 | Harada et al. |
| 2006/0264987 A1 | 11/2006 | Sgro |
| 2006/0271072 A1 | 11/2006 | Hummel et al. |
| 2007/0016228 A1 | 1/2007 | Salas |
| 2007/0021761 A1 | 1/2007 | Phillips |
| 2007/0021766 A1 | 1/2007 | Belagali et al. |
| 2007/0023476 A1 | 2/2007 | Whitman et al. |
| 2007/0023477 A1 | 2/2007 | Whitman et al. |
| 2007/0027458 A1 | 2/2007 | Sixto, Jr. et al. |
| 2007/0034669 A1 | 2/2007 | de la Torre et al. |
| 2007/0038233 A1 | 2/2007 | Martinez et al. |
| 2007/0049947 A1 | 3/2007 | Menn et al. |
| 2007/0049948 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0049953 A2 | 3/2007 | Shimoji et al. |
| 2007/0066981 A1 | 3/2007 | Meagher |
| 2007/0073314 A1 | 3/2007 | Gadberry et al. |
| 2007/0083218 A1 | 4/2007 | Morris |
| 2007/0093790 A1 | 4/2007 | Downey et al. |
| 2007/0093856 A1 | 4/2007 | Whitfield et al. |
| 2007/0106314 A1 | 5/2007 | Dunn |
| 2007/0112365 A1 | 5/2007 | Hilal et al. |
| 2007/0118155 A1 | 5/2007 | Goldfarb et al. |
| 2007/0118161 A1 | 5/2007 | Kennedy et al. |
| 2007/0118163 A1 | 5/2007 | Boudreaux et al. |
| 2007/0118174 A1 | 5/2007 | Chu |

(56) References Cited

U.S. PATENT DOCUMENTS

| | | |
|---|---|---|
| 2007/0123916 A1 | 5/2007 | Maier et al. |
| 2007/0142848 A1 | 6/2007 | Ainsworth et al. |
| 2007/0142851 A1 | 6/2007 | Sixto et al. |
| 2007/0149988 A1 | 6/2007 | Michler et al. |
| 2007/0149989 A1 | 6/2007 | Santilli et al. |
| 2007/0162060 A1 | 7/2007 | Wild |
| 2007/0173866 A1 | 7/2007 | Sorrentino et al. |
| 2007/0175949 A1 | 8/2007 | Shelton et al. |
| 2007/0185504 A1 | 8/2007 | Manetakis et al. |
| 2007/0191868 A1 | 8/2007 | Theroux et al. |
| 2007/0203509 A1 | 8/2007 | Bettuchi |
| 2007/0203510 A1 | 8/2007 | Bettuchi |
| 2007/0213747 A1 | 9/2007 | Monassevitch et al. |
| 2007/0250080 A1 | 10/2007 | Jones et al. |
| 2007/0265640 A1 | 11/2007 | Kortenbach et al. |
| 2007/0276417 A1 | 11/2007 | Mendes, Jr. et al. |
| 2007/0282355 A1 | 12/2007 | Brown et al. |
| 2007/0288039 A1 | 12/2007 | Aranyi et al. |
| 2007/0293875 A1 | 12/2007 | Soetikno et al. |
| 2008/0004636 A1 | 1/2008 | Walberg et al. |
| 2008/0004637 A1 | 1/2008 | Klassen et al. |
| 2008/0004639 A1 | 1/2008 | Huitema et al. |
| 2008/0015615 A1 | 1/2008 | Molitor et al. |
| 2008/0027465 A1 | 1/2008 | Vitali et al. |
| 2008/0027466 A1 | 1/2008 | Vitali et al. |
| 2008/0045981 A1 | 2/2008 | Margolin et al. |
| 2008/0051808 A1 | 2/2008 | Rivera et al. |
| 2008/0065118 A1 | 3/2008 | Damarati |
| 2008/0083813 A1 | 4/2008 | Zemlok et al. |
| 2008/0103510 A1 | 5/2008 | Taylor et al. |
| 2008/0147092 A1 | 6/2008 | Rogge et al. |
| 2008/0147093 A1 | 6/2008 | Roskopf et al. |
| 2008/0154287 A1 | 6/2008 | Rosenberg et al. |
| 2008/0167665 A1 | 7/2008 | Arp et al. |
| 2008/0167671 A1 | 7/2008 | Giordano et al. |
| 2008/0228199 A1 | 9/2008 | Cropper et al. |
| 2008/0243145 A1 | 10/2008 | Whitfield et al. |
| 2008/0255413 A1 | 10/2008 | Zemlok et al. |
| 2008/0255589 A1 | 10/2008 | Blakeney et al. |
| 2008/0306492 A1 | 12/2008 | Shibata et al. |
| 2008/0306493 A1 | 12/2008 | Shibata et al. |
| 2008/0312665 A1 | 12/2008 | Shibata et al. |
| 2008/0312670 A1 | 12/2008 | Lutze et al. |
| 2008/0319456 A1 | 12/2008 | Hart et al. |
| 2009/0076533 A1 | 3/2009 | Kayan et al. |
| 2009/0088777 A1 | 4/2009 | Miyagi et al. |
| 2009/0088783 A1 | 4/2009 | Kennedy et al. |
| 2009/0171380 A1 | 7/2009 | Whiting |
| 2009/0182193 A1 | 7/2009 | Whitman et al. |
| 2009/0209946 A1 | 8/2009 | Swayze et al. |
| 2009/0222003 A1 | 9/2009 | Otley |
| 2009/0228023 A1 | 9/2009 | Cui |
| 2009/0228024 A1 | 9/2009 | Whitfield et al. |
| 2009/0264904 A1 | 10/2009 | Aldrich et al. |
| 2009/0299382 A1 | 12/2009 | Zergiebel |
| 2009/0326558 A1 | 12/2009 | Cui et al. |
| 2010/0049216 A1 | 2/2010 | Zergiebel |
| 2010/0057105 A1 | 3/2010 | Sorrentino et al. |
| 2010/0057107 A1 | 3/2010 | Sorrentino et al. |
| 2010/0069935 A1 | 3/2010 | Crainich |
| 2010/0274262 A1 | 10/2010 | Schulz et al. |
| 2010/0274264 A1 | 10/2010 | Schulz et al. |
| 2010/0318103 A1 | 12/2010 | Cheng et al. |
| 2011/0054498 A1 | 3/2011 | Monassevitch et al. |
| 2011/0082474 A1 | 4/2011 | Bindra et al. |
| 2011/0087241 A1 | 4/2011 | Nguyen |
| 2011/0087243 A1 | 4/2011 | Nguyen et al. |
| 2011/0112552 A1 | 5/2011 | Lehman et al. |
| 2011/0137323 A1 | 6/2011 | Malkowski et al. |
| 2011/0137324 A1 | 6/2011 | Boudreaux et al. |
| 2011/0144662 A1 | 6/2011 | McLawhorn et al. |
| 2011/0144665 A1 | 6/2011 | Malkowski |
| 2011/0190791 A1 | 8/2011 | Jacobs et al. |
| 2011/0208211 A1 | 8/2011 | Whitfield et al. |
| 2011/0208212 A1 | 8/2011 | Zergiebel et al. |
| 2011/0218553 A1 | 9/2011 | Huitema et al. |
| 2011/0218554 A1 | 9/2011 | Cheng et al. |
| 2011/0218555 A1 | 9/2011 | Huitema |
| 2011/0218556 A1 | 9/2011 | Nguyen et al. |
| 2011/0224696 A1 | 9/2011 | Huitema et al. |
| 2011/0224700 A1 | 9/2011 | Schmidt et al. |
| 2011/0224701 A1 | 9/2011 | Menn |
| 2011/0230900 A1 | 9/2011 | Sarradon |
| 2011/0245847 A1 | 10/2011 | Menn et al. |
| 2011/0245848 A1 | 10/2011 | Rosenberg et al. |
| 2011/0251608 A1 | 10/2011 | Timm et al. |
| 2011/0295290 A1 | 12/2011 | Whitfield |
| 2011/0313437 A1 | 12/2011 | Yeh |
| 2012/0029534 A1 | 2/2012 | Whitfield et al. |
| 2012/0041455 A1 | 2/2012 | Martinez |
| 2012/0046671 A1 | 2/2012 | Matsuoka et al. |
| 2012/0048759 A1 | 3/2012 | Disch et al. |
| 2012/0053402 A1 | 3/2012 | Conlon et al. |
| 2012/0059394 A1 | 3/2012 | Brenner et al. |
| 2012/0065647 A1 | 3/2012 | Litscher et al. |
| 2012/0109158 A1 | 5/2012 | Zammataro |
| 2012/0116420 A1 | 5/2012 | Sorrentino et al. |
| 2012/0197269 A1 | 8/2012 | Zammataro |
| 2012/0226291 A1 | 9/2012 | Malizia et al. |
| 2012/0253298 A1 | 10/2012 | Henderson et al. |
| 2012/0265220 A1 | 10/2012 | Menn |
| 2012/0277765 A1 | 11/2012 | Zammataro et al. |
| 2012/0330326 A1 | 12/2012 | Creston et al. |
| 2013/0110135 A1 | 5/2013 | Whitfield et al. |
| 2013/0131697 A1 | 5/2013 | Hartoumbekis |
| 2013/0165951 A1 | 6/2013 | Blake, III |
| 2013/0165952 A1 | 6/2013 | Whitfield et al. |
| 2013/0172909 A1 | 7/2013 | Harris |
| 2013/0172910 A1 | 7/2013 | Malkowski |
| 2013/0172911 A1 | 7/2013 | Rockrohr et al. |
| 2013/0172912 A1 | 7/2013 | Whitfield et al. |
| 2013/0175320 A1 | 7/2013 | Mandakolathur Vasudevan et al. |
| 2013/0226200 A1 | 8/2013 | Kappel et al. |
| 2013/0253540 A1 | 9/2013 | Castro et al. |
| 2013/0253541 A1 | 9/2013 | Zergiebel |
| 2013/0274767 A1 | 10/2013 | Sorrentino et al. |
| 2013/0289583 A1 | 10/2013 | Zergiebel et al. |
| 2013/0296891 A1 | 11/2013 | Hartoumbekis |
| 2013/0296892 A1 | 11/2013 | Sorrentino et al. |
| 2013/0310849 A1 | 11/2013 | Malkowski |
| 2013/0325040 A1 | 12/2013 | Zammataro |
| 2014/0005693 A1 | 1/2014 | Shelton, IV et al. |
| 2014/0039526 A1 | 2/2014 | Malkowski |
| 2014/0052157 A1 | 2/2014 | Whitfield et al. |
| 2014/0058412 A1 | 2/2014 | Aranyi et al. |
| 2014/0074143 A1 | 3/2014 | Fitzgerald et al. |
| 2014/0194903 A1 | 7/2014 | Malkowski et al. |
| 2014/0207156 A1 | 7/2014 | Malkowski |
| 2014/0263565 A1 | 9/2014 | Lytle, IV et al. |
| 2014/0276970 A1 | 9/2014 | Messerly et al. |
| 2014/0296879 A1 | 10/2014 | Menn et al. |
| 2014/0316441 A1 | 10/2014 | Zergiebel et al. |
| 2014/0330291 A1 | 11/2014 | Whitfield et al. |
| 2015/0005790 A1 | 1/2015 | Whitfield et al. |
| 2015/0032131 A1 | 1/2015 | Sorrentino et al. |
| 2015/0045816 A1 | 2/2015 | Aranyi et al. |
| 2015/0066057 A1 | 3/2015 | Rockrohr et al. |
| 2015/0080916 A1 | 3/2015 | Aranyi et al. |
| 2015/0127022 A1 | 5/2015 | Whitfield et al. |
| 2015/0164511 A1 | 6/2015 | Whitfield et al. |
| 2015/0190138 A1 | 7/2015 | Whitfield et al. |
| 2015/0190139 A1 | 7/2015 | Zammataro |
| 2015/0282808 A1 | 10/2015 | Sorrentino et al. |
| 2015/0351771 A1 | 12/2015 | Malkowski et al. |
| 2015/0351772 A1 | 12/2015 | Malkowski et al. |
| 2016/0030044 A1 | 2/2016 | Zammataro |
| 2016/0030045 A1 | 2/2016 | Malkowski et al. |
| 2016/0113655 A1 | 4/2016 | Holsten |
| 2016/0151071 A1 | 6/2016 | Tokarz et al. |
| 2016/0192940 A1 | 7/2016 | Gokharu |
| 2016/0213377 A1 | 7/2016 | Shankarsetty |
| 2016/0242767 A1 | 8/2016 | Kasvikis |
| 2016/0242789 A1 | 8/2016 | Sorrentino et al. |
| 2016/0256157 A1 | 9/2016 | Rockrohr et al. |

(56) References Cited

U.S. PATENT DOCUMENTS

| | | |
|---|---|---|
| 2016/0256158 A1 | 9/2016 | Whitfield et al. |
| 2016/0262764 A1 | 9/2016 | Gokharu |
| 2016/0296236 A1 | 10/2016 | Whitfield et al. |
| 2016/0338695 A1 | 11/2016 | Hartoumbekis |
| 2016/0338699 A1 | 11/2016 | Sorrentino et al. |
| 2017/0027581 A1 | 2/2017 | Zergiebel et al. |
| 2017/0049449 A1 | 2/2017 | Aranyi et al. |
| 2017/0065277 A1 | 3/2017 | Malkowski |
| 2017/0065281 A1 | 3/2017 | Zammataro |
| 2017/0086846 A1 | 3/2017 | Sorrentino et al. |
| 2017/0086850 A1 | 3/2017 | Zergiebel |
| 2017/0128071 A1 | 5/2017 | Holsten et al. |
| 2017/0172780 A1 | 6/2017 | Murthy Aravalli |
| 2017/0238936 A1 | 8/2017 | Mujawar |
| 2017/0258472 A1 | 9/2017 | Aranyi et al. |
| 2017/0325814 A1 | 11/2017 | Malkowski |
| 2017/0340325 A1 | 11/2017 | Baril et al. |
| 2017/0340331 A1 | 11/2017 | Hu et al. |
| 2017/0340332 A1 | 11/2017 | Whitfield et al. |
| 2017/0360449 A1 | 12/2017 | Rockrohr et al. |
| 2018/0008276 A1 | 1/2018 | Bhatnagar et al. |
| 2018/0008277 A1 | 1/2018 | Baril |
| 2018/0070952 A1 | 3/2018 | Malkowski et al. |
| 2018/0116671 A1 | 5/2018 | Prior |
| 2018/0116673 A1 | 5/2018 | Baril et al. |
| 2018/0116674 A1 | 5/2018 | Baril |
| 2018/0116675 A1 | 5/2018 | Baril |
| 2018/0116676 A1 | 5/2018 | Williams |
| 2018/0168660 A1 | 6/2018 | Gokharu |
| 2018/0214156 A1 | 8/2018 | Baril et al. |
| 2018/0221028 A1 | 8/2018 | Williams |
| 2018/0228492 A1 | 8/2018 | Aranyi et al. |
| 2018/0228567 A1 | 8/2018 | Baril et al. |
| 2018/0235632 A1 | 8/2018 | Mujawar et al. |
| 2018/0235633 A1 | 8/2018 | Baril et al. |
| 2018/0235637 A1 | 8/2018 | Xu et al. |
| 2018/0242977 A1 | 8/2018 | Tan et al. |
| 2018/0263624 A1 | 9/2018 | Malkowski et al. |
| 2018/0271526 A1 | 9/2018 | Zammataro |
| 2018/0317927 A1 | 11/2018 | Cai et al. |
| 2018/0317928 A1 | 11/2018 | P V R |
| 2018/0325519 A1 | 11/2018 | Baril et al. |
| 2019/0000449 A1 | 1/2019 | Baril et al. |
| 2019/0000482 A1 | 1/2019 | Hu et al. |
| 2019/0000584 A1 | 1/2019 | Baril |

FOREIGN PATENT DOCUMENTS

| | | | |
|---|---|---|---|
| CA | 1163889 A | | 3/1984 |
| CA | 2740831 A1 | | 4/2010 |
| CN | 1994236 A | | 7/2007 |
| CN | 101401737 A | | 4/2009 |
| CN | 101530340 A | | 9/2009 |
| CN | 100571640 C | | 12/2009 |
| CN | 101658437 A | | 3/2010 |
| CN | 101664329 A | | 3/2010 |
| CN | 101664331 A | | 3/2010 |
| CN | 201683954 U | | 12/2010 |
| CN | 103083059 A | | 5/2013 |
| CN | 103181809 A | | 7/2013 |
| CN | 103181810 A | | 7/2013 |
| CN | 104487006 A | | 4/2015 |
| CN | 104605911 B | | 2/2017 |
| DE | 202007003398 U1 | | 6/2007 |
| DE | 20 2009 006113 U1 | | 7/2009 |
| EP | 0000756 A1 | | 2/1979 |
| EP | 0073655 A1 | | 3/1983 |
| EP | 0085931 A2 | | 8/1983 |
| EP | 0086721 A2 | | 8/1983 |
| EP | 0089737 A1 | | 9/1983 |
| EP | 0092300 A1 | | 10/1983 |
| EP | 0324166 A2 | | 7/1989 |
| EP | 0392750 A1 | | 10/1990 |
| EP | 0406724 A1 | | 1/1991 |
| EP | 0409569 A1 | | 1/1991 |
| EP | 0 510 826 A1 | | 10/1992 |
| EP | 0514139 A3 | | 3/1993 |
| EP | 0569223 A1 | | 11/1993 |
| EP | 0594003 A1 | | 4/1994 |
| EP | 0598529 A2 | | 5/1994 |
| EP | 0622049 A1 | | 11/1994 |
| EP | 0685204 A1 | | 12/1995 |
| EP | 0732078 A2 | | 9/1996 |
| EP | 0755655 A2 | | 1/1997 |
| EP | 0760230 A1 | | 3/1997 |
| EP | 0769274 A1 | | 4/1997 |
| EP | 0769275 A1 | | 4/1997 |
| EP | 0 793 944 A1 | | 9/1997 |
| EP | 0834286 A1 | | 4/1998 |
| EP | 1317906 A1 | | 6/2003 |
| EP | 1468653 A2 | | 10/2004 |
| EP | 1609427 A1 | | 12/2005 |
| EP | 1712187 A2 | | 10/2006 |
| EP | 1712191 A2 | | 10/2006 |
| EP | 1757236 A2 | | 2/2007 |
| EP | 1813199 A1 | | 8/2007 |
| EP | 1813207 A1 | | 8/2007 |
| EP | 1894531 A2 | | 3/2008 |
| EP | 1908423 A2 | | 4/2008 |
| EP | 1913881 A1 | | 4/2008 |
| EP | 1939231 A1 | | 7/2008 |
| EP | 2000102 A2 | | 12/2008 |
| EP | 2140817 A1 | | 1/2010 |
| EP | 2229895 A1 | | 9/2010 |
| EP | 2 263 570 A1 | | 12/2010 |
| EP | 2332471 A1 | | 6/2011 |
| EP | 2412318 A2 | | 2/2012 |
| EP | 2412319 A2 | | 2/2012 |
| EP | 2 752 165 A2 | | 7/2014 |
| GB | 1134832 A | | 11/1968 |
| GB | 2073022 A | | 10/1981 |
| GB | 2 132 899 A | | 7/1984 |
| JP | 10118083 | | 5/1998 |
| JP | 2003033361 A | | 2/2003 |
| JP | 2006501954 A | | 1/2006 |
| JP | 2006154230 A | | 6/2006 |
| JP | 2006209948 A | | 8/2006 |
| JP | 2006277221 A | | 10/2006 |
| JP | 2007250843 A | | 9/2007 |
| JP | 2008017876 A | | 1/2008 |
| JP | 2008047498 A | | 2/2008 |
| JP | 2008055165 A | | 3/2008 |
| JP | 2008515550 A | | 5/2008 |
| JP | 2009198991 A | | 9/2009 |
| JP | 5499386 B2 | | 5/2014 |
| WO | 0042922 A1 | | 7/2000 |
| WO | 01/65997 A2 | | 9/2001 |
| WO | 2001-66001 A2 | | 9/2001 |
| WO | 2001-67965 A1 | | 9/2001 |
| WO | 2003-086207 A1 | | 10/2003 |
| WO | 2003-092473 A2 | | 11/2003 |
| WO | 2004032762 A1 | | 4/2004 |
| WO | 2005091457 A1 | | 9/2005 |
| WO | 2006042076 A2 | | 4/2006 |
| WO | 2006042084 A2 | | 4/2006 |
| WO | 2006042110 A2 | | 4/2006 |
| WO | 2006042141 A2 | | 4/2006 |
| WO | 2006135479 A2 | | 12/2006 |
| WO | 2008118928 A2 | | 10/2008 |
| WO | 2008127968 A2 | | 10/2008 |
| WO | 2016192096 A1 | | 12/2016 |
| WO | 2016192718 A2 | | 12/2016 |
| WO | 2016197350 A1 | | 12/2016 |
| WO | 2016206015 A1 | | 12/2016 |

OTHER PUBLICATIONS

Extended European Search Report corresponding to European Appln. No. EP 16 18 3184.7 dated Jan. 24, 2017.

Japanese Office Action corresponding to Japanese Appln. No. JP 2016-097807 dated Feb. 14, 2017.

European Office Action corresponding to European Appln. No. EP 12 19 3447.5 dated Apr. 4, 2017.

(56) References Cited

OTHER PUBLICATIONS

Chinese First Office Action corresponding to Chinese Appln. No. CN 201410008877.5 dated Apr. 6, 2017.
Extended European Search Report corresponding to European Appln. No. EP 17 15 3714.5 dated May 11, 2017.
Extended European Search Report corresponding to European Appln. No. EP 17 15 8519.3 dated May 19, 2017.
Extended European Search Report corresponding to European Appln. No. EP 17 15 7606.9 dated May 22, 2017.
European Office Action corresponding to European Appln. No. EP 11 25 0674.6 dated May 23, 2017.
Canadian Office Action corresponding to Canadian Appln. No. CA 2,743,402 dated May 30, 2017.
Chinese First Office Action corresponding to Int'l Appln. No. CN 201510205737.1 dated Nov. 1, 2016.
European Office Action corresponding to Int'l Appln. No. EP 08 73 2820.9 dated Nov. 3, 2016.
Extended European Search Report corresponding to Int'l Appln. No. EP 16 18 5465.8 dated Dec. 21, 2016.
Extended European Search Report corresponding to Int'l Appln. No. EP 16 18 4652.2 dated Jan. 4, 2017.
Chinese First Office Action corresponding to Int'l Appln. No. CN 201510419902.3 dated Jan. 4, 2017.
European Office Action corresponding to European Appln. No. EP 16 15 9324.9 dated Aug. 7, 2017.
Chinese First Office Action corresponding to Chinese Appln. No. CN 2014104295806 dated Aug. 31, 2017.
Extended European Search Report corresponding to European Appln. No. EP 17 17 3508.7 dated Sep. 29, 2017.
Chinese Second Office Action corresponding to Chinese Appln. No. CN 201410076318.8 dated Oct. 10, 2017.
Extended European Search Report corresponding to European Appln. No. EP 17 18 0570.8 dated Dec. 6, 2017.
Japanese Office Action corresponding to counterpart Int'l Application No. JP 2014-245081 dated Oct. 28, 2015.
Canadian Office Action corresponding to counterpart Int'l Application No. CA 2,675,921 dated Oct. 30, 2015.
Chinese Office Action corresponding to counterpart Int'l Application No. CN 201210555570.8 dated Nov. 2, 2015.
Canadian Office Action corresponding to counterpart Int'l Application No. CA 2,676,309 dated Nov. 3, 2015.
Canadian Office Action corresponding to counterpart Int'l Application No. CA 2,676,211 dated Nov. 24, 2015.
Canadian Office Action corresponding to counterpart Int'l Application No. CA 2,676,547 dated Nov. 25, 2015.
Extended European Search Report corresponding to counterpart Int'l Application No. EP 15 17 3809.3 dated Nov. 25, 2015.
Chinese Office Action corresponding to counterpart Int'l Application No. CN 201210586814.9 dated Dec. 2, 2015.
Extended European Search Report corresponding to counterpart Int'l Application No. EP 12 17 2940.4 dated Dec. 14, 2015.
European Search Report for EP 14192026 dated Jul. 17, 2015.
Chinese First Office Action corresponding to counterpart Int'l Appln. No. CN 201210586826.1 dated Dec. 30, 2015.
Extended European Search Report corresponding to counterpart Int'l Appln. No. EP 15 19 1313.4 dated Feb. 1, 2016.
Extended European Search Report corresponding to counterpart Int'l Appln. No. EP 15 18 5362.9 dated Feb. 12, 2016.
Extended European Search Report corresponding to counterpart Int'l Appln. No. EP 12 19 7813.4 dated Mar. 7, 2016.
Canadian Office Action corresponding to counterpart Int'l Appln. No. CA 2,676,465 dated Mar. 8, 2016.
Japanese Office Action corresponding to counterpart Int'l Appln. No. JP 2014-245081 dated Mar. 18, 2016.
Japanese Office Action corresponding to counterpart Int'l Appln. No. JP 2015-005629 dated Mar. 18, 2016.
Extended European Search Report corresponding to counterpart Int'l Appln. No. EP 15 19 3549.1 dated Mar. 22, 2016.

International Search Report and Written Opinion corresponding to counterpart Int'l Appln. No. PCT/CN2015/082199 dated Mar. 31, 2016.
Extended European Search Report corresponding to counterpart Int'l Appln. No. EP 15 19 7251.0 dated Apr. 8, 2016.
Extended European Search Report corresponding to counterpart Int'l Appln. No. EP 16 15 0739.7 dated May 17, 2016.
Canadian Office Action corresponding to counterpart Int'l Appln. No. CA 2,716,672 dated May 31, 2016.
Canadian Office Action corresponding to counterpart Int'l Appln. No. CA 2,717,448 dated May 31, 2016.
Canadian Office Action corresponding to counterpart Int'l Appln. No. CA 2,721,951 dated Jun. 1, 2016.
Partial European Search Report corresponding to counterpart Int'l Appln. No. EP 16 15 0287.7 dated Jun. 16, 2016.
Chinese Second Office Action corresponding to counterpart Int'l Appln. No. CN 201210555570.8 dated Jun. 20, 2016.
International Search Report & Written Opinion corresponding to Int'l Appln. No. PCT/CN2015/091603 dated Jul. 8, 2016.
Japanese Office Action corresponding to JP 2011-160130 dated Dec. 1, 2014.
Chinese Office Action corresponding to CN 201210015011.8 dated Jan. 4, 2015.
Japanese Office Action corresponding to JP 2011-160126 dated Jan. 9, 2015.
Japanese Office Action corresponding to JP 2011-184521 dated Jan. 15, 2015.
Extended European Search Report corresponding to 14 18 2236.1 dated Jan. 20, 2015.
Chinese Office Action corresponding to CN 201110201736.1 dated Feb. 9, 2015.
Extended European Search Report corresponding to EP 14 16 1540.1 dated Feb. 27, 2015.
Australian Office Action corresponding to AU 2010226985 dated Mar. 31, 2015.
Australian Office Action corresponding to AU 2013211526 dated Apr. 6, 2015.
Australian Office Action corresponding to AU 2011211463 dated Apr. 13, 2015.
Australian Office Action corresponding to AU 2013254887 dated Apr. 14, 2015.
Japanese Office Action corresponding to JP 2013-225272 dated May 1, 2015.
European Office Action corresponding to EP 12 152 989.5 dated May 4, 2015.
Australian Office Action corresponding to AU 2009212759 dated May 7, 2015.
Japanese Office Action corresponding to JP 2013-229070 dated May 8, 2015.
Japanese Office Action corresponding to JP 2013-229996 dated May 8, 2015.
Japanese Office Action corresponding to JP 2014-190735 dated May 27, 2015; no English translation attached—unavailable.
Chinese Second Office Action corresponding to Int'l Appln. No. CN 201210586814.9 dated Jul. 18, 2016.
Chinese First Office Action corresponding to Int'l Appln. No. CN 201510093591.6 dated Jul. 25, 2016.
International Search Report & Written Opinion corresponding to Int'l Appln. No. PCT/CN2015/094172 dated Aug. 4, 2016.
Canadian Office Action corresponding to Int'l Appln. No. CA 2,728,538 dated Sep. 6, 2016.
Chinese Second Office Action corresponding to Int'l Appln. No. CN 201210586826.1 dated Sep. 14, 2016.
Extended European Search Report corresponding to Int'l Appln. No. EP 16 15 0287.7 dated Oct. 4, 2016.
The extended European Search Report corresponding to European Application No. EP 07 25 3905.9, completed Jan. 29, 2008; dated Feb. 7, 2008; (7 Pages).
International Search Report corresponding to International Application No. PCT-US08-58185, completed Sep. 4, 2008; dated Sep. 9, 2008; (2 Pages).

(56) References Cited

OTHER PUBLICATIONS

The International Search Report corresponding to International Application No. PCT-US08-59859, completed Sep. 14, 2008; dated Sep. 18, 2008; (2 Pages).
The extended European Search Report corresponding to European Application No. EP 07 25 3807.7, completed Nov. 1, 2008; dated Nov. 26, 2008; (11 Pages).
The extended European Search Report corresponding to European Application No. EP 09 25 2049.3, completed Dec. 11, 2009; dated Jan. 12, 2010; (3 Pages).
The extended European Search Report corresponding to European Application No. EP 09 25 2050.1, completed Dec. 23, 2009; dated Jan. 21, 2010; (3 Pages).
The extended European Search Report corresponding to European Application No. EP 09 25 2051.9, completed Dec. 21, 2009; dated Jan. 28, 2010; (3 Pages).
The extended European Search Report corresponding to European Application No. EP 09 25 2052.7, completed Nov. 16, 2009; dated Nov. 24, 2009; (3 Pages).
The extended European Search Report corresponding to European Application No. EP 09 25 2053.5, completed Nov. 24, 2009; dated Dec. 1, 2009; (3 Pages).
The extended European Search Report corresponding to European Application No. EP 09 25 2054.3, completed Jan. 1, 2010; dated Jan. 22, 2010; (3 Pages).
The extended European Search Report corresponding to European Application No. EP 09 25 2056.8, completed Jan. 3, 2010; dated Feb. 5, 2010; (3 Pages).
The extended European Search Report corresponding to European Application No. EP 10 25 0497.4, completed May 4, 2010; dated May 12, 2010; (6 Pages).
The extended European Search Report corresponding to European Application No. EP 10 25 2079.8, completed Mar. 3, 2011; dated Mar. 17, 2011; (3 Pages).
The European Search Report corresponding to European Application No. EP 05 81 0218.7, completed Apr. 18, 2011; dated May 20, 2011; (3 Pages).
The European Search Report corresponding to European Application No. EP 05 80 7612.6, completed May 2, 2011; dated May 20, 2011; (3 pages).
The extended European Search Report corresponding to European Application No. EP 10 25 1737.2, completed May 9, 2011; dated May 20, 2011; (4 pages).
The extended European Search Report corresponding to European Application No. EP 11 25 0214.1, completed May 25, 2011; dated Jun. 1, 2011; (3 Pages).
The extended European Search Report corresponding to European Application No. EP 11 00 2681.2, completed May 31, 2011; dated Jun. 10, 2011; (3 Pages).
The European Search Report corresponding to European Application No. EP 05 80 2686.5, completed Jan. 9, 2012; dated Jan. 18, 2012; (3 Pages).
The extended European Search Report corresponding to European Application No. EP 12 15 1313.9, completed Mar. 20, 2012 and dated Apr. 12, 2012; (5 Pages).
The extended European Search Report corresponding to European Application No. EP 12 16 1291.5, completed Apr. 24, 2012 and dated May 4, 2012; (5 Pages).
The extended European Search Report corresponding to European Application No. EP 12 16 5891.8, completed Jun. 12, 2012 and dated Jun. 20, 2012; (6 Pages).
The extended European Search Report corresponding to European Application No. EP 12 16 2288.0, completed Jun. 4, 2012 and dated Jul. 7, 2012; (6 Pages).
The extended European Search Report corresponding to European Application No. EP 12 16 4955.2, completed Aug. 23, 2012 and dated Sep. 4, 2012; (5 Pages).
The extended European Search Report corresponding to European Application No. EP 11 25 0754.6, completed Oct. 22, 2012 and dated Oct. 31, 2012; (6 Pages).
The extended European Search Report corresponding to European Application No. EP 12 18 6401.1, completed Nov. 22, 2012 and dated Nov. 30, 2012; (7 Pages).
The extended European Search Report corresponding to European Application No. EP 12 18 6448.2, completed Nov. 28, 2012 and dated Dec. 10, 2012; (6 Pages).
The extended European Search Report corresponding to European Application No. EP 12 19 1706.6, completed Dec. 19, 2012 and dated Jan. 8, 2013; (6 Pages).
The Extended European Search Report corresponding to EP 12 19 8745.7, completed Mar. 19, 2013 and dated Apr. 11, 2013; (8 Pages).
The Extended European Search Report corresponding to EP 12 15 2989.5, completed Apr. 9, 2013 and dated Apr. 18, 2013; (9 Pages).
The Extended European Search Report corresponding to EP 08 73 2820.9, completed Jul. 2, 2013 and dated Jul. 9, 2013; (10 Pages).
The Extended European Search Report corresponding to EP 13 17 2008.8, completed Aug. 14, 2013 and dated Aug. 28, 2013; (8 Pages).
The Extended European Search Report corresponding to EP 13 16 6382.5, completed Nov. 19, 2013 and dated Nov. 28, 2013; (8 Pages).
The Extended European Search Report corresponding to EP 11 25 0194.5, completed Nov. 25, 2013 and dated Dec. 3, 2013; (8 Pages).
The Extended European Search Report corresponding to EP 10 25 1798.4, completed Dec. 12, 2013 and dated Jan. 2, 2014; (9 Pages).
"Salute II Disposable Fixation Device", Technique Guide—Laparoscopic and Open Inguinal and Ventral Hernia Repair; Davol, A Bard Company, 2006; (7 Pages).
The Extended European Search Report corresponding to EP 10 25 2112.7, completed Jul. 29, 2014 and dated Aug. 5, 2014; (8 pp).
The Extended European Search Report corresponding to EP 14 15 1673.2, completed Apr. 25, 2014 and dated May 3, 2014; (8 pp).
Chinese Office Action corresponding to counterpart Int'l Appln No. CN 201210212642.9 dated Jun. 3, 2015.
European Office Action corresponding to counterpart Int'l Appln No. EP 04 719 757.9 dated Jun. 12, 2015.
European Office Action corresponding to counterpart Int'l Appln No. EP 13 166 382.5 dated Jun. 19, 2015.
Japanese Office Action corresponding to counterpart Int'l Application No. JP 2010-226908 dated Jun. 26, 2015.
Extended European Search Report corresponding to counterpart Int'l Application No. EP 15 15 5024.1 dated Jul. 17, 2015.
Japanese Office Action corresponding to counterpart Int'l Application No. JP 2011-160126 dated Aug. 10, 2015.
Extended European Search Report corresponding to counterpart Int'l Application No. EP 14 15 0321.9 dated Sep. 23, 2015.
Extended European Search Report corresponding to counterpart Int'l Application No. EP 11 25 0675.3 dated Oct. 7, 2015.
Extended European Search Report corresponding to counterpart Int'l Application No. EP 11 25 0674.6 dated Oct. 7, 2015.
Extended European Search Report corresponding to counterpart Int'l Application No. EP 12 19 3447.5 dated Oct. 19, 2015.
Canadian Office Action corresponding to counterpart Int'l Application No. CA 2,675,875 dated Oct. 26, 2015.
Japanese Office Action corresponding to counterpart Int'l Application No. JP 2015-005629 dated Oct. 28, 2015.
Extended European Search Report corresponding to Patent Application EP 18154617.7 dated Jun. 25, 2018.
Extended European Search Report corresponding to Patent Application EP 18155158.1 dated Jun. 28, 2018.
European Search Report corresponding to Patent Application EP 15877428.1 dated Jul. 2, 2018.
European Search Report corresponding to Patent Application EP 18157789.1 dated Jul. 5, 2018.
Office Action corresponding to Patent Application CA 2,972,444 dated Aug. 9, 2018.
European Search Report corresponding to Patent Application EP 18156458.4 dated Sep. 3, 2018.
European Search Report corresponding to Patent Application EP 18171682.0 dated Sep. 18, 2018.
European Search Report corresponding to Patent Application EP 15878354.8 dated Sep. 19, 2018.

(56) References Cited

OTHER PUBLICATIONS

European Search Report corresponding to Patent Application EP 18183394.8 dated Sep. 28, 2018.
Extended European Search Report corresponding to Patent Application EP 18163041.9 dated Sep. 28, 2018.
Extended European Search Report corresponding to Patent Application EP 18170524.5 dated Oct. 1, 2018.
Japanese Office Action corresponding to Patent Application JP 2017-536546 dated Oct. 15, 2018.
Extended European Search Report corresponding to Patent Application EP 18187640.0 dated Nov. 30, 2018.
Extended European Search Report corresponding to Patent Application EP 18187690.5 dated Nov. 30, 2018.
Chinese First Office Action corresponding to Patent Application CN 201510696298.9 dated Dec. 3, 2018.
Extended European Search Report corresponding to Patent Application EP 18158143.0 dated Dec. 5, 2018.

* cited by examiner

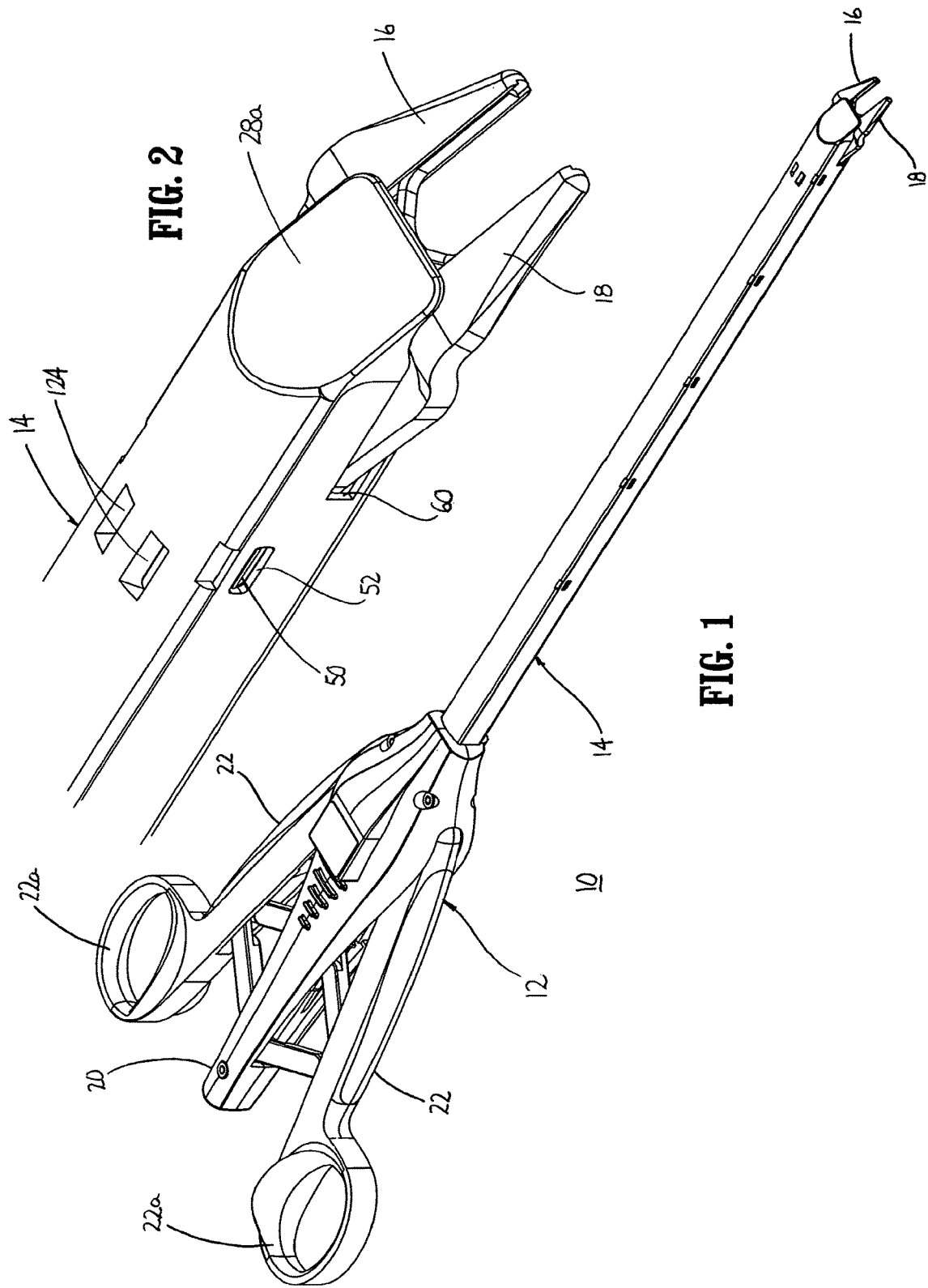

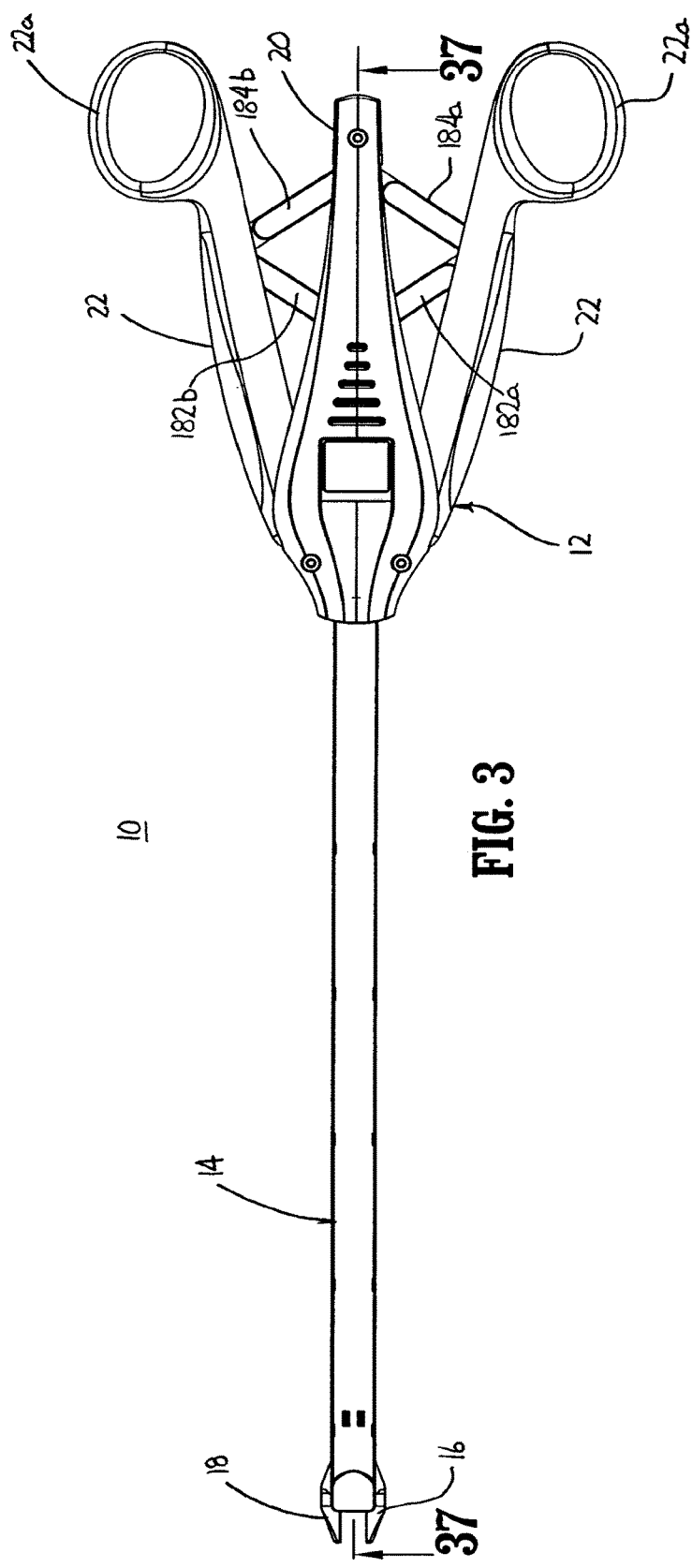
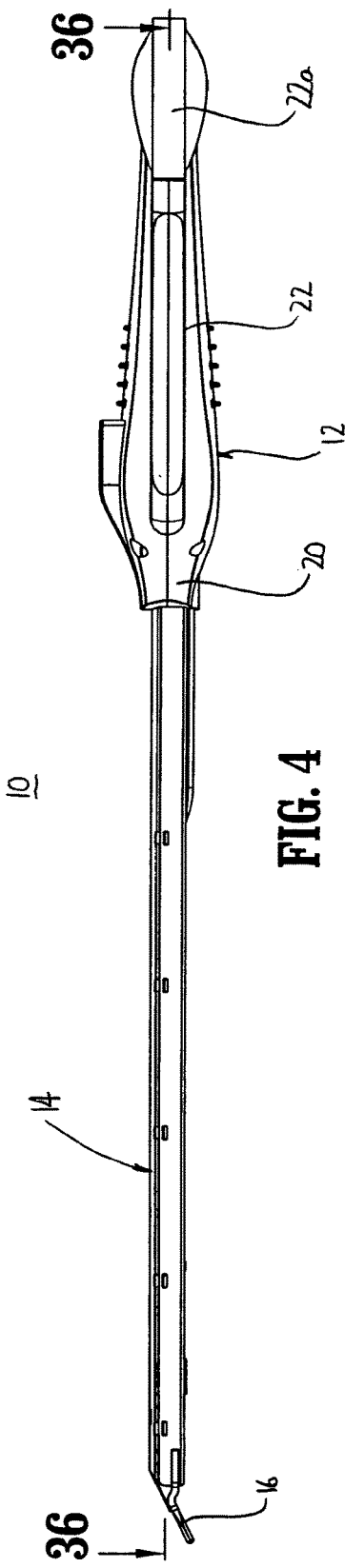
FIG. 3
FIG. 4

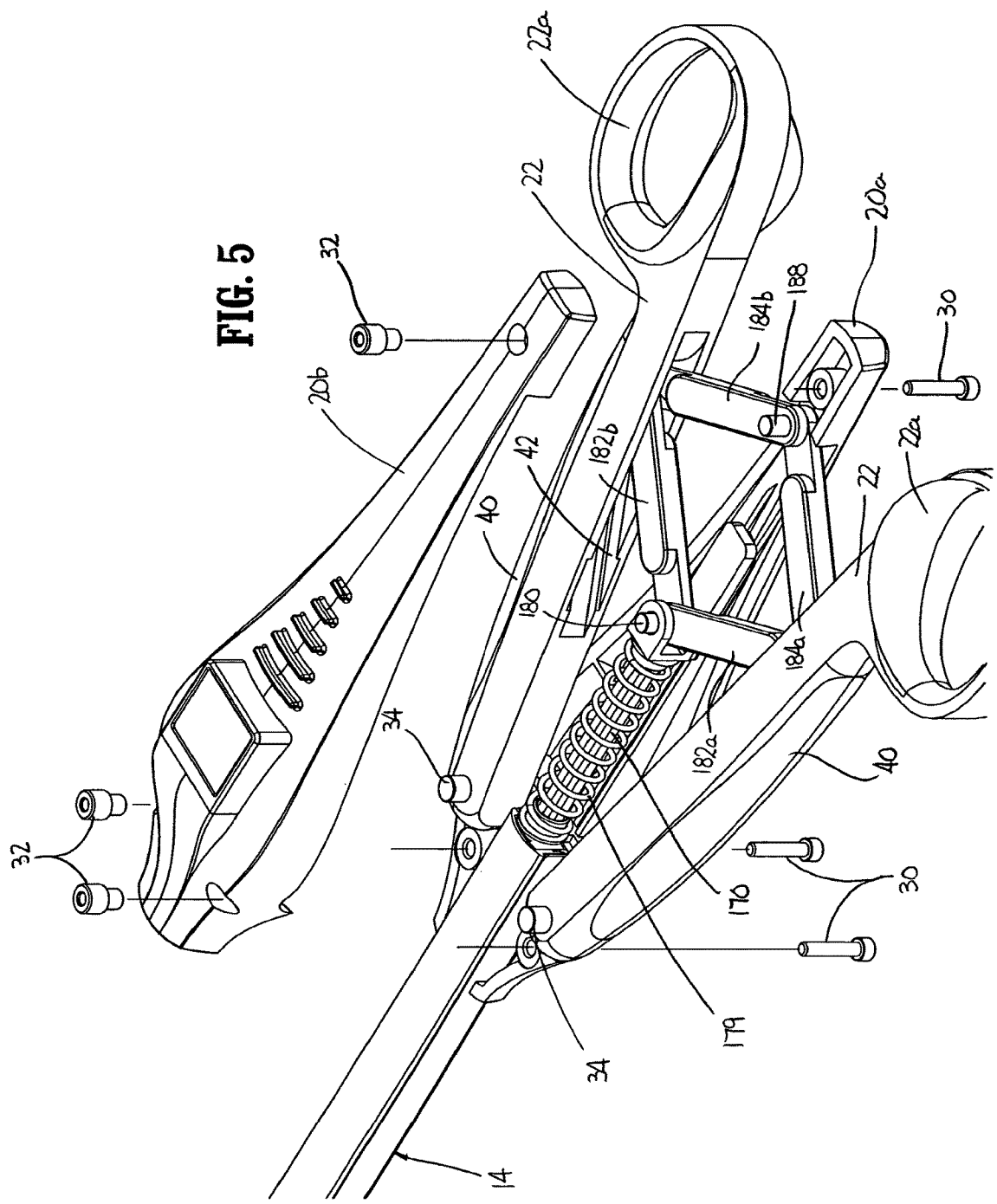

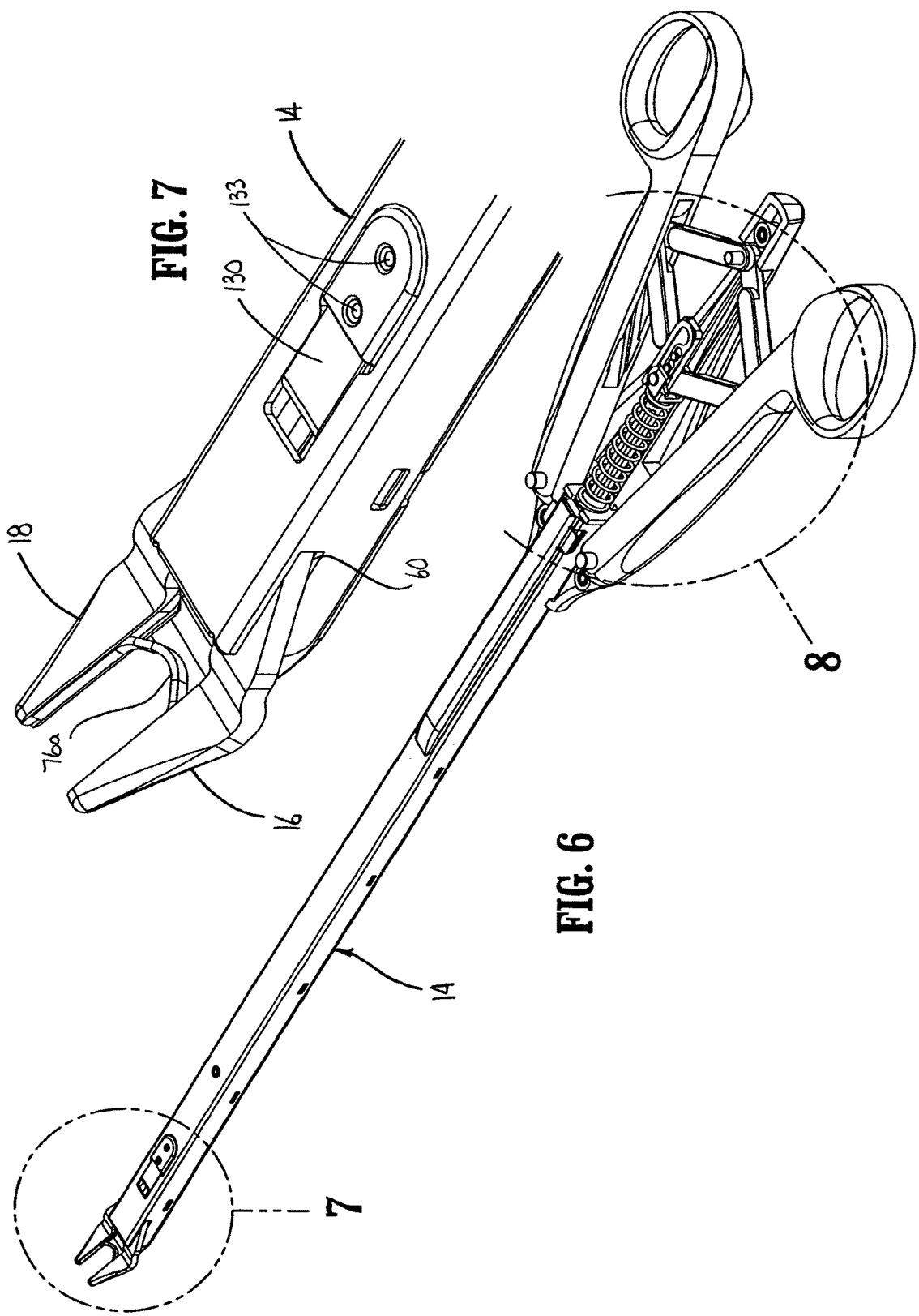

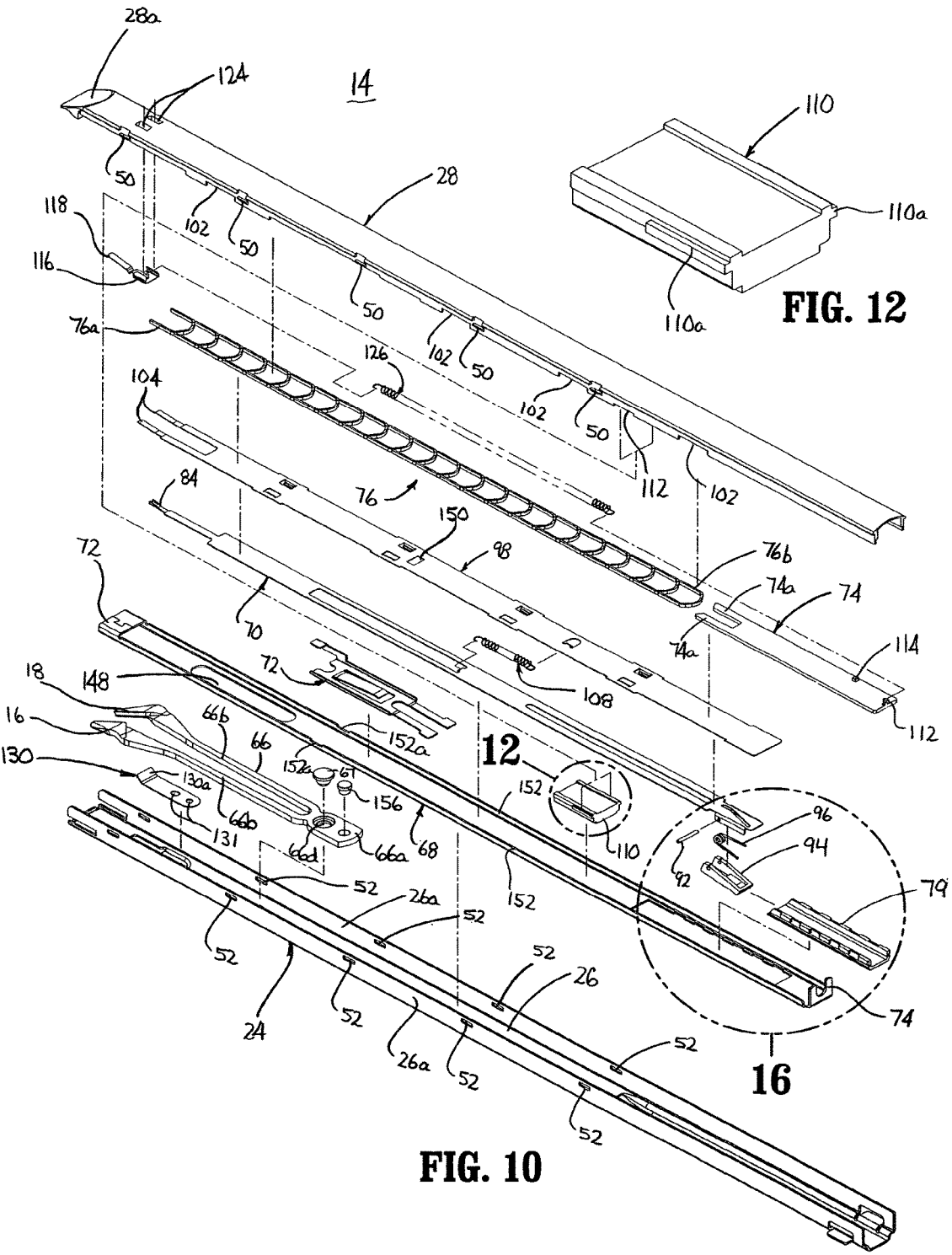

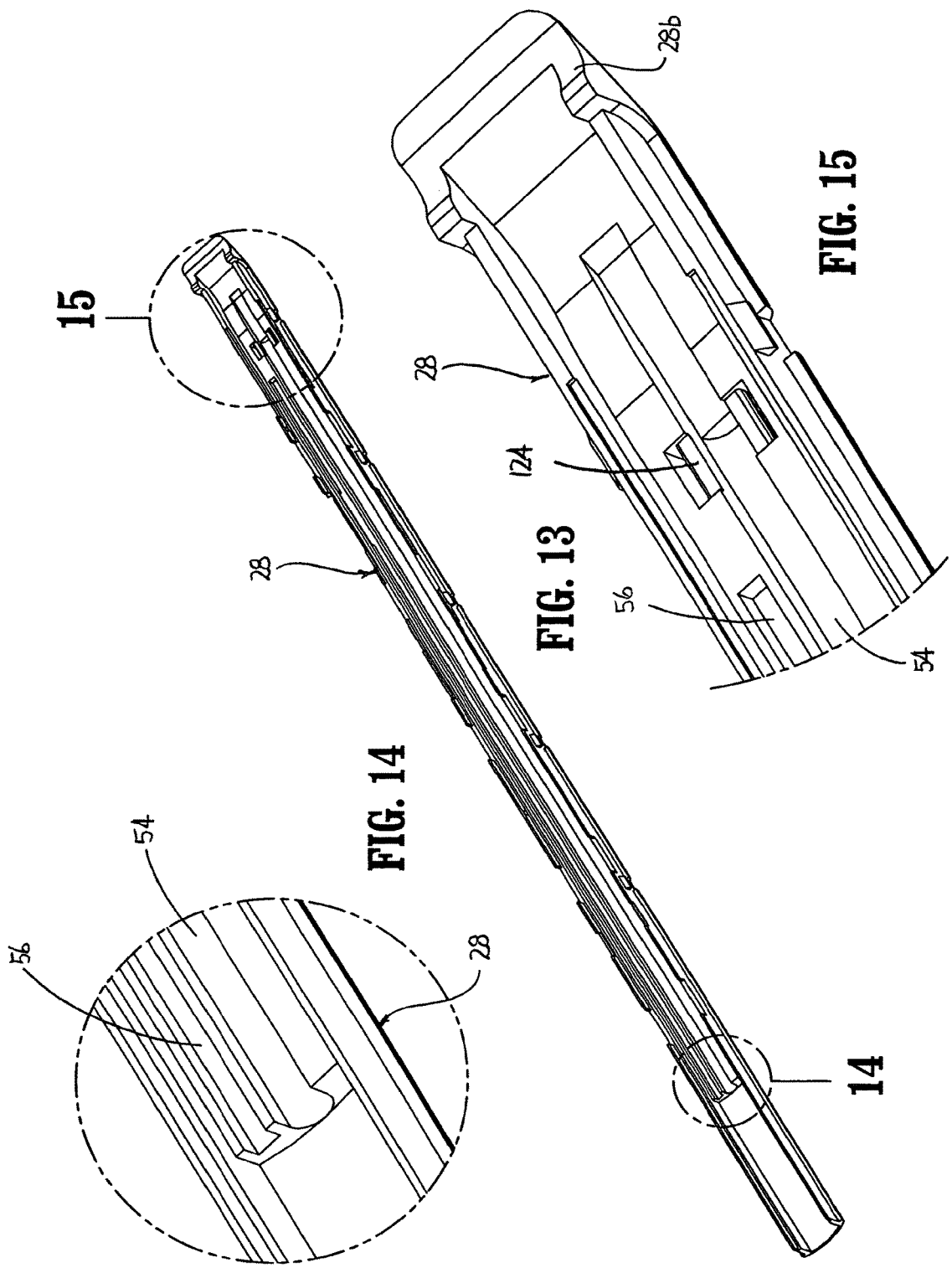

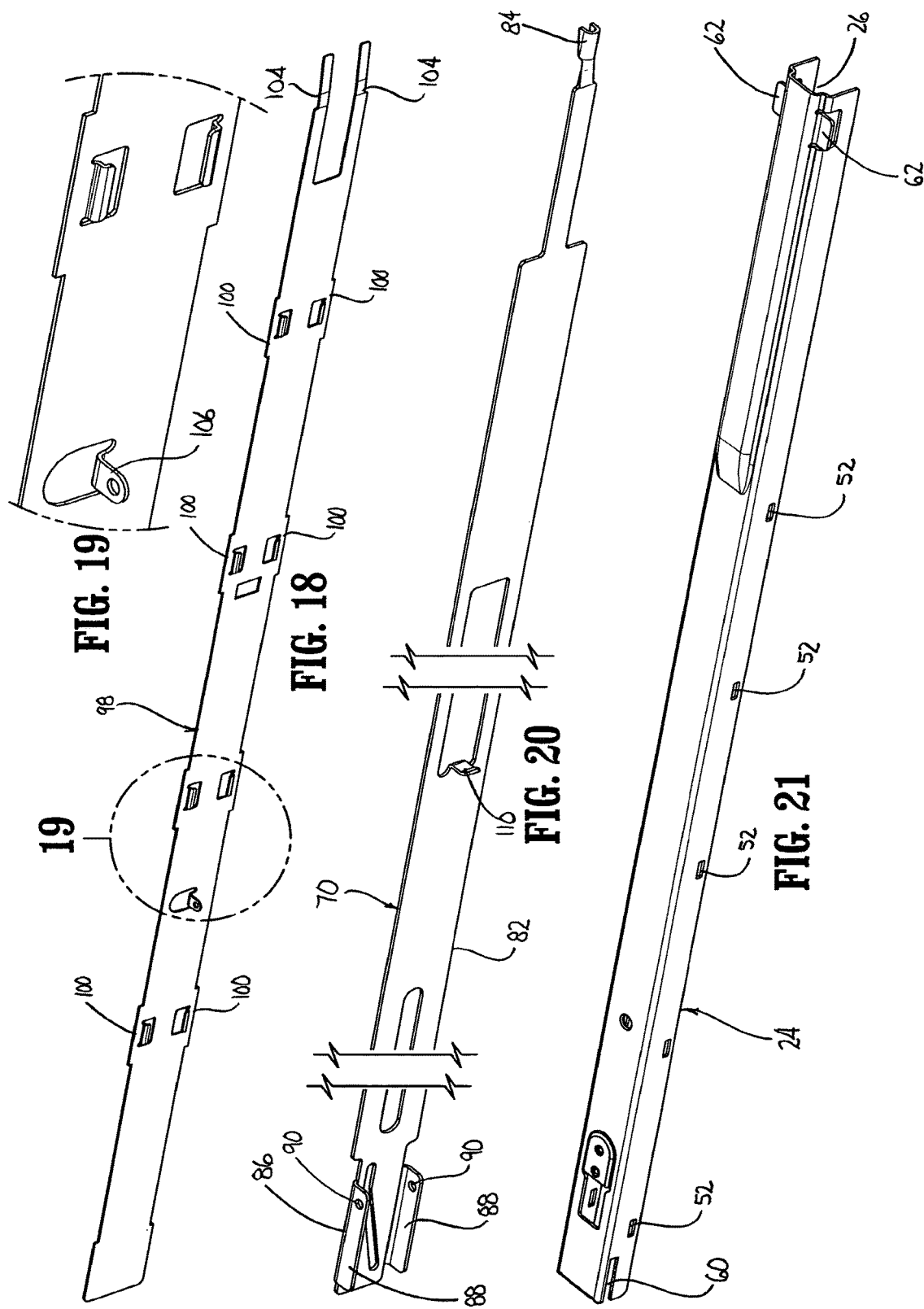

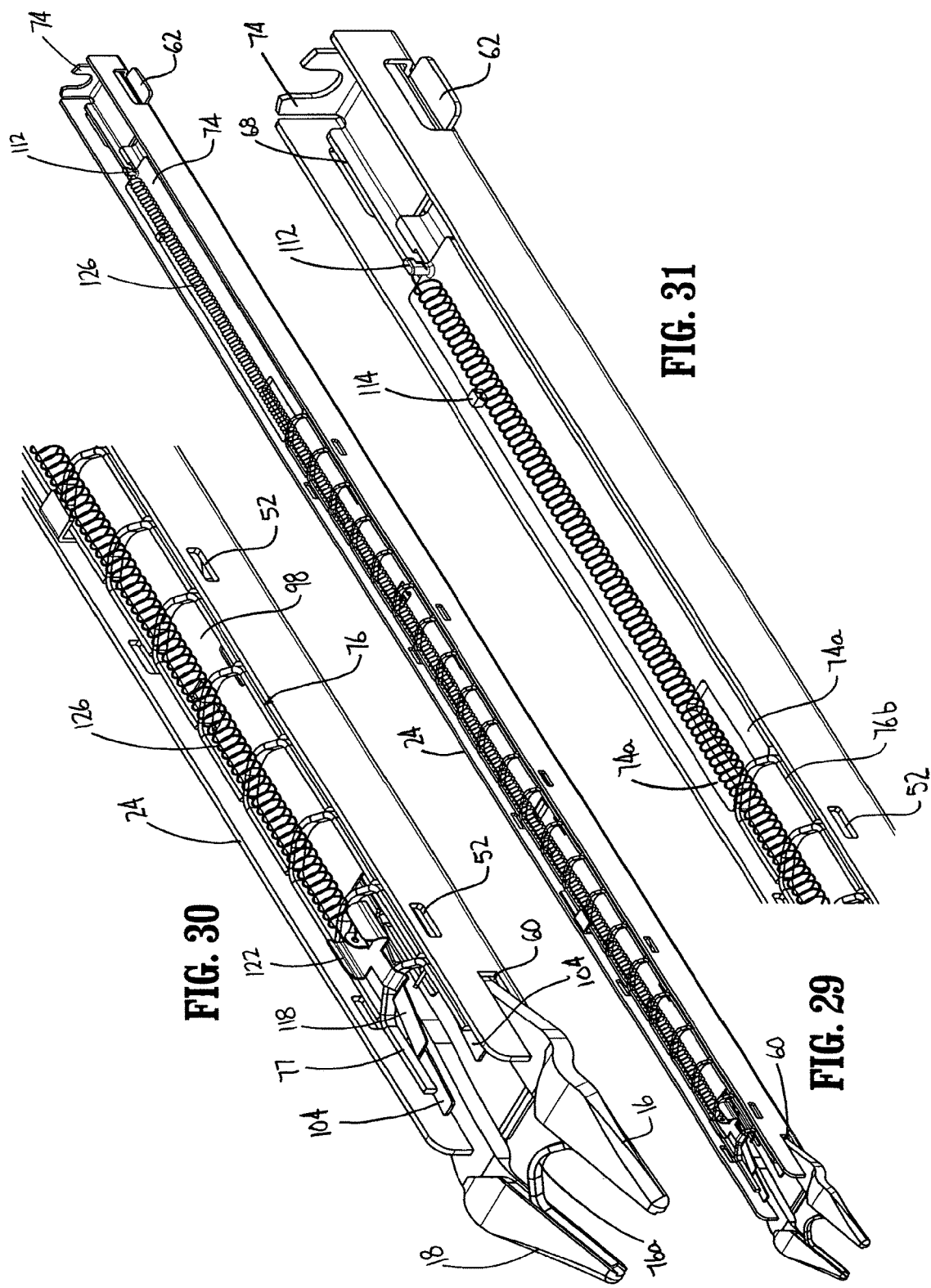

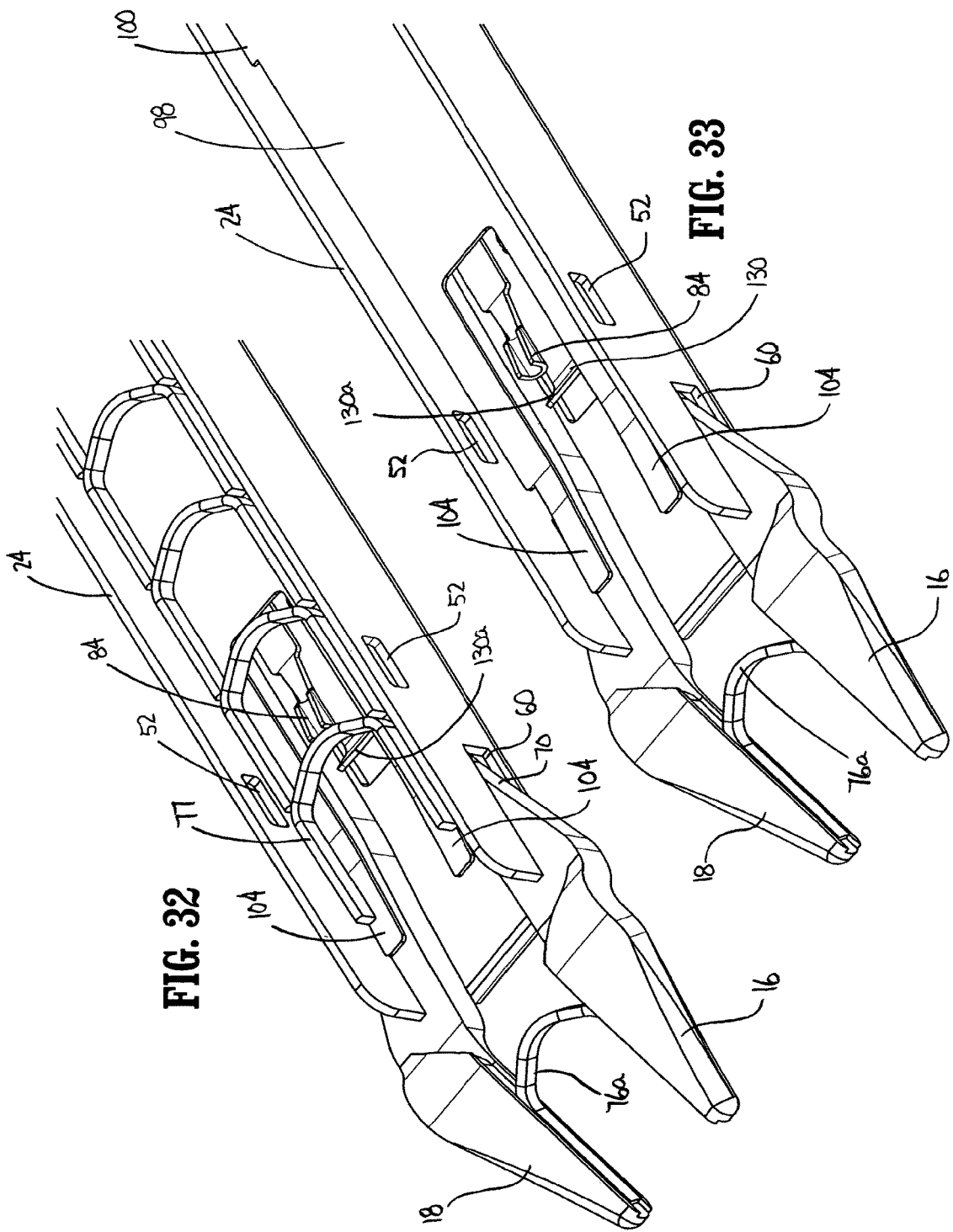

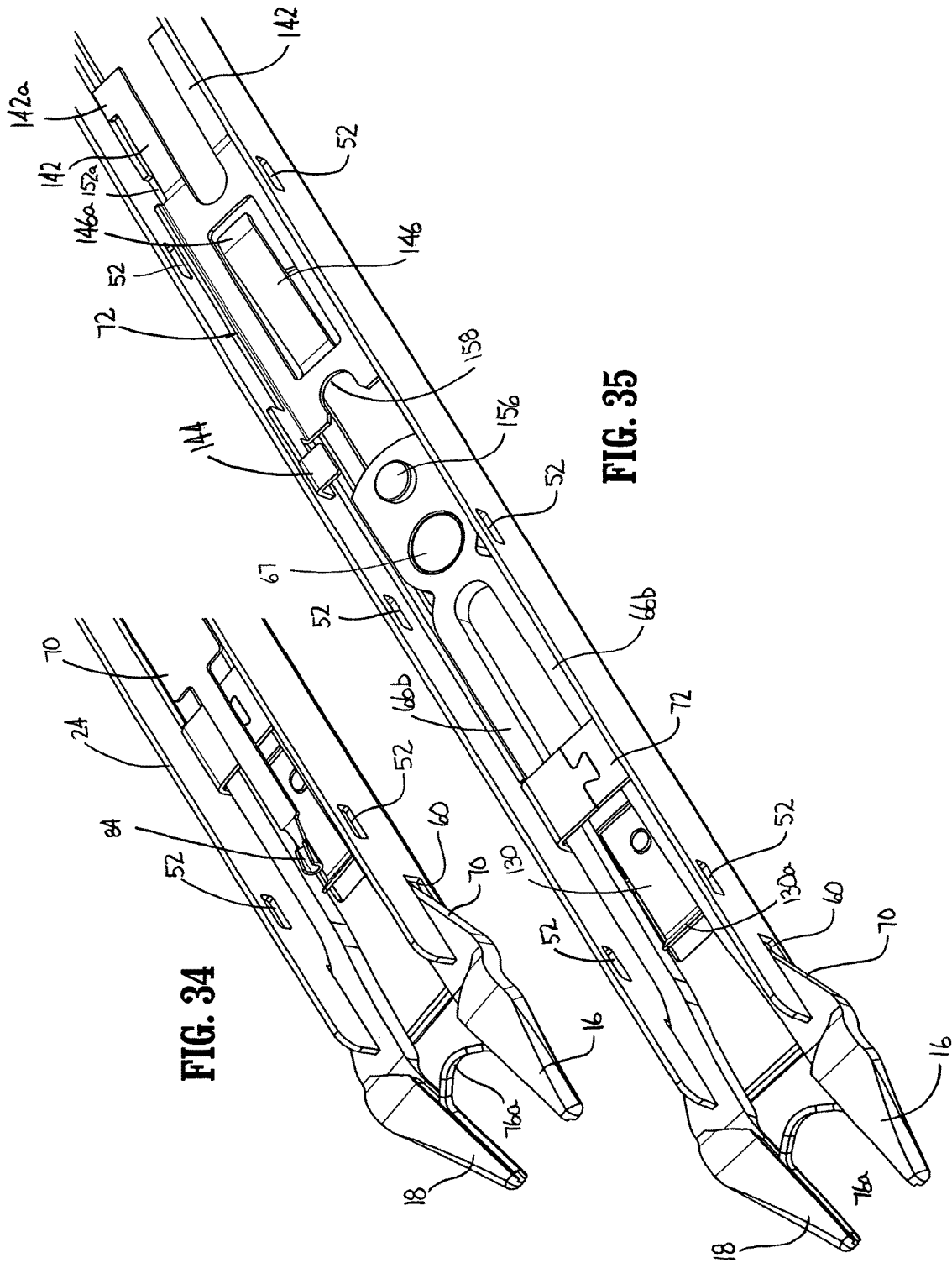

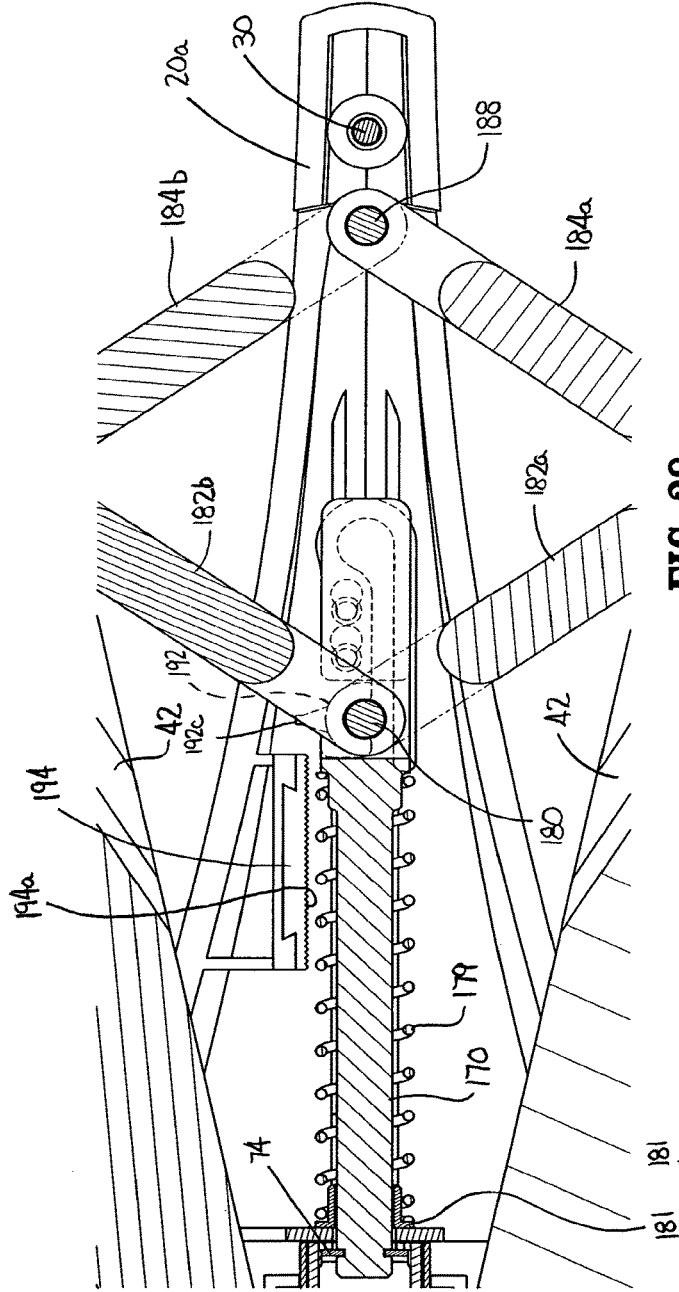
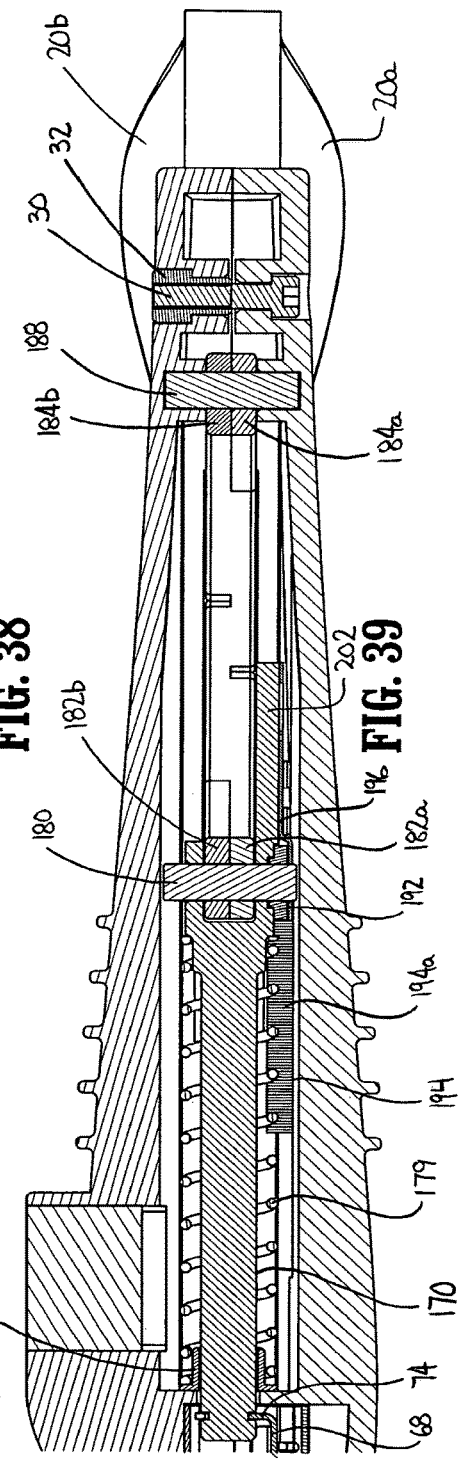
FIG. 38
FIG. 39

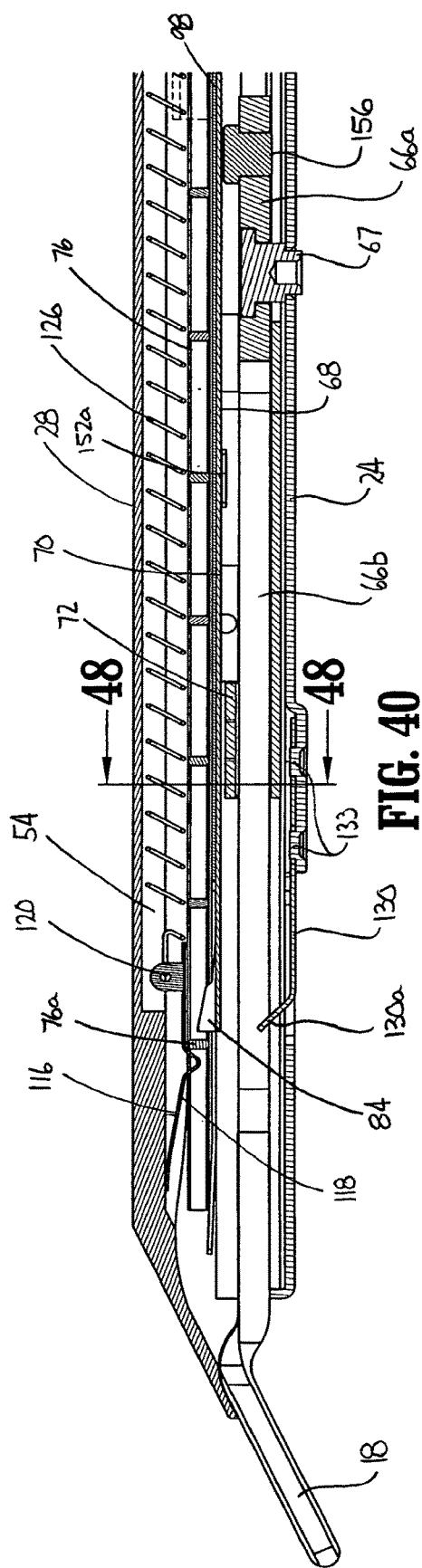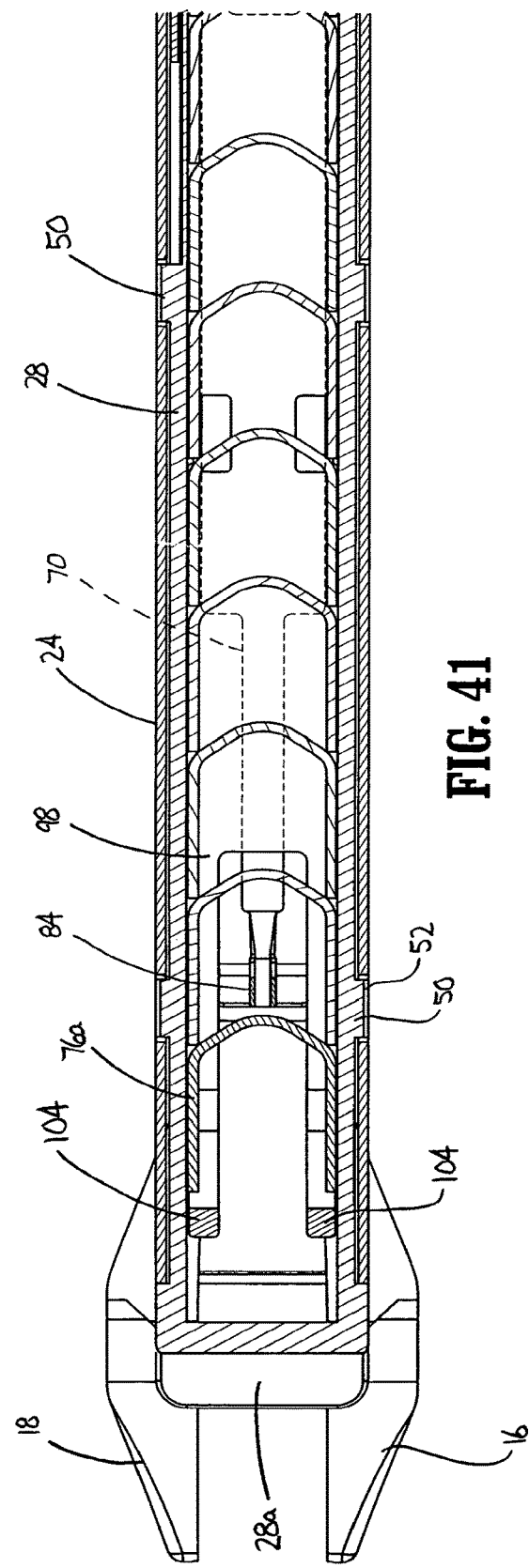

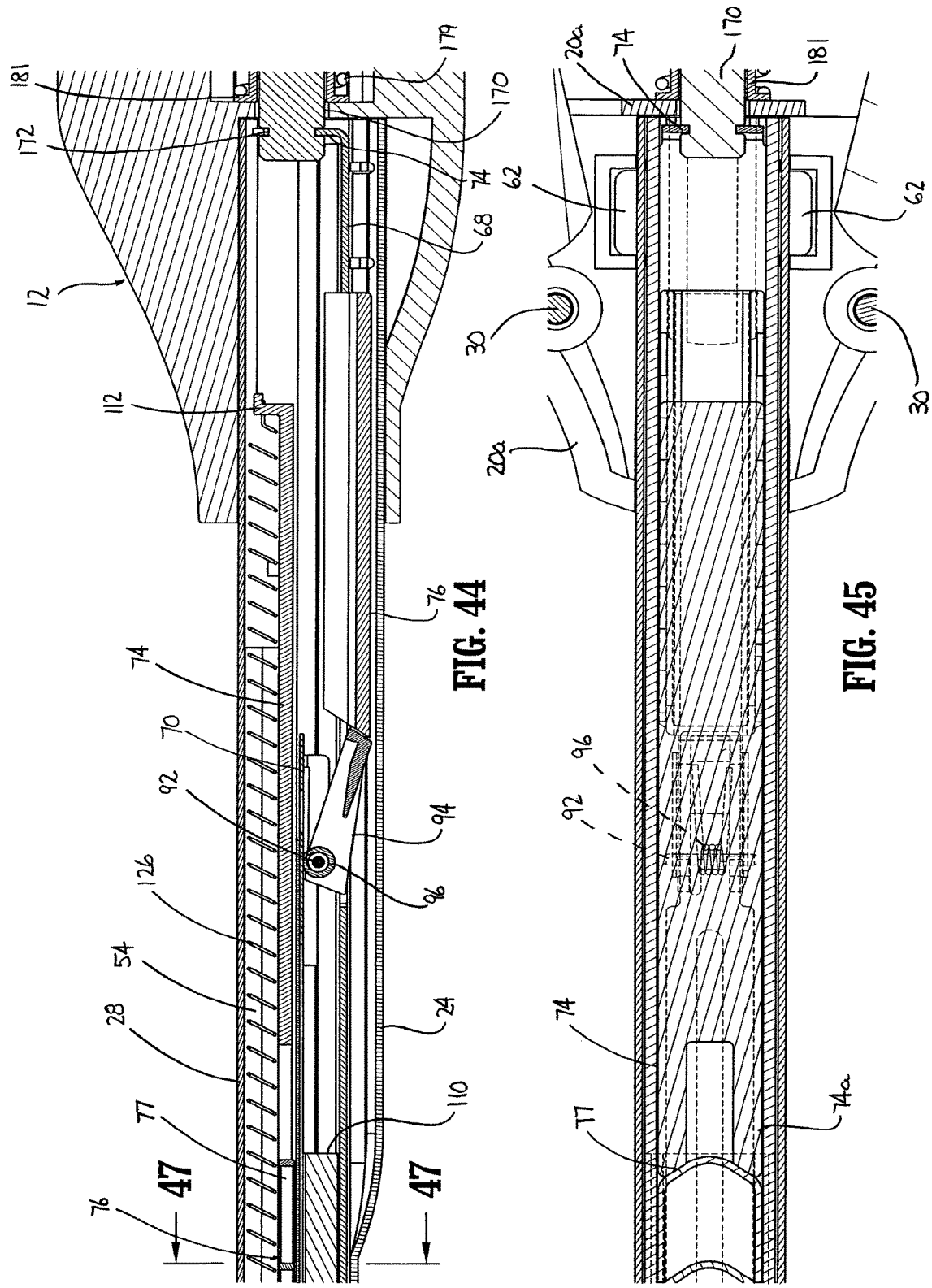

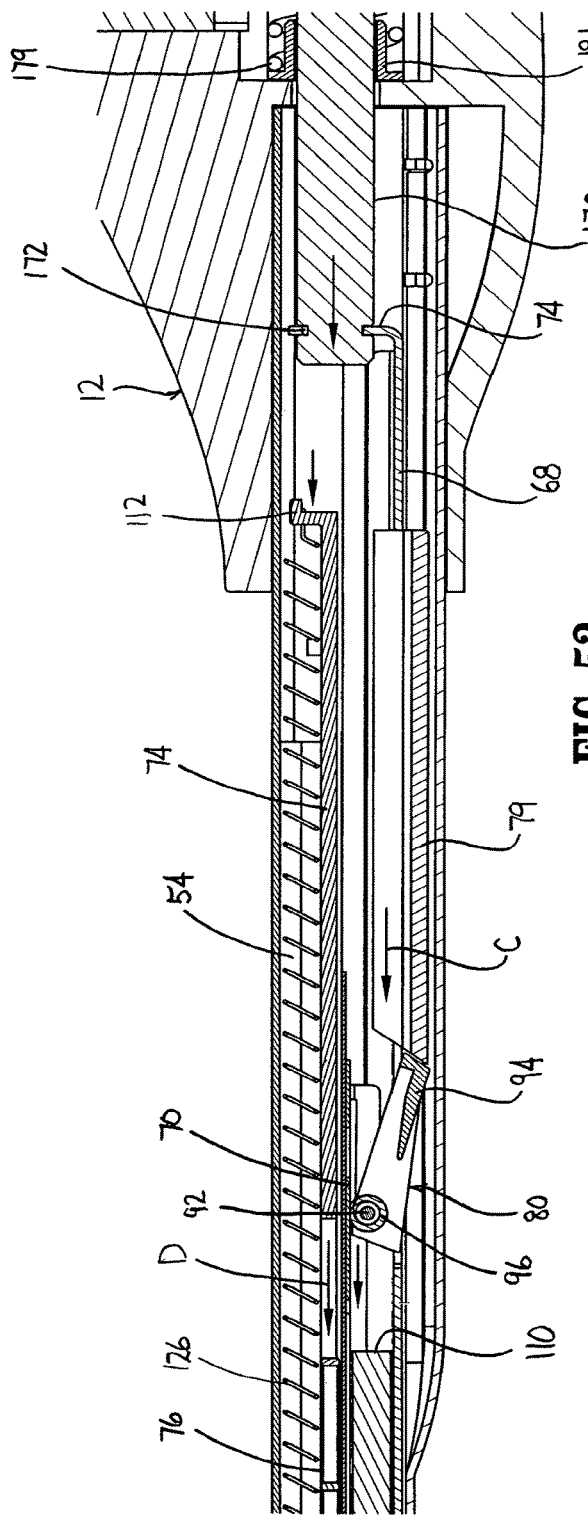
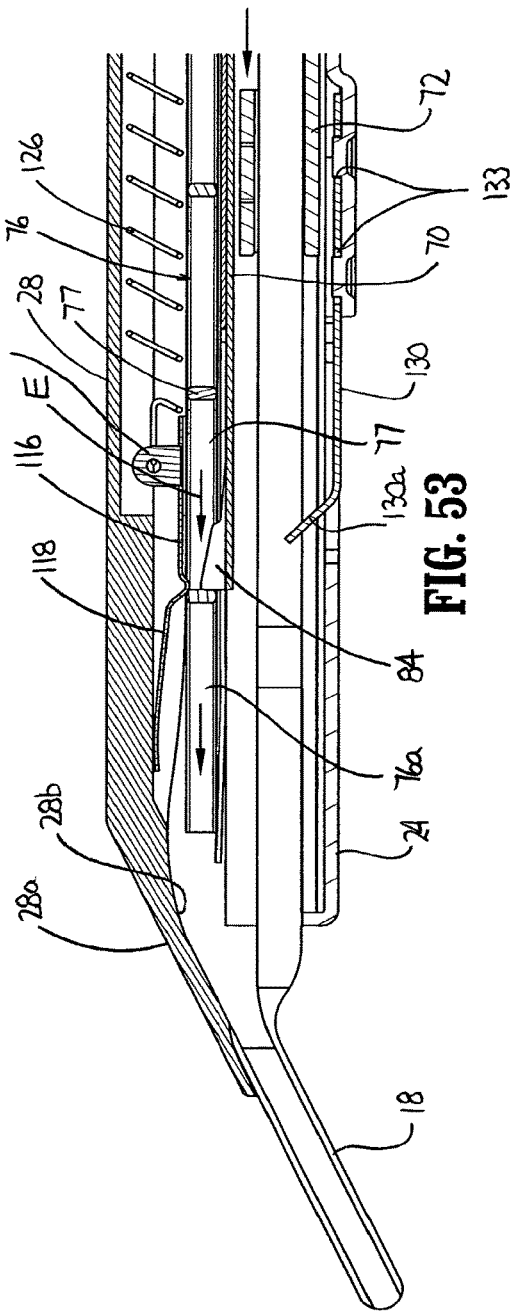
FIG. 52
FIG. 53

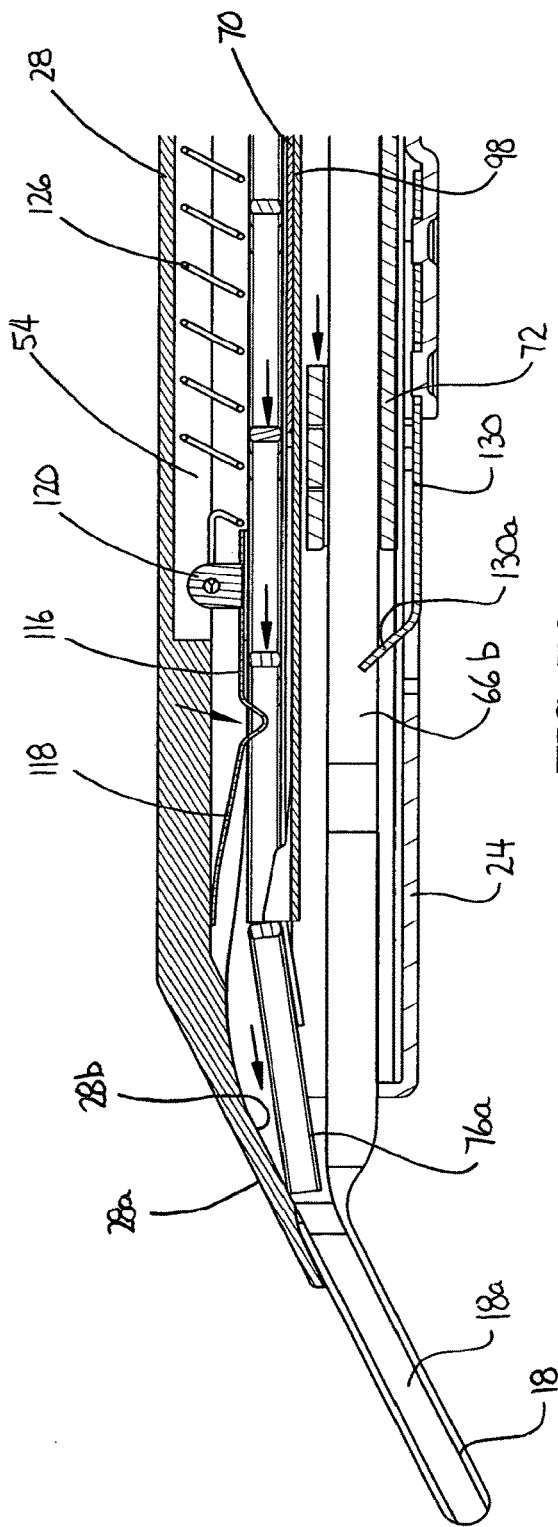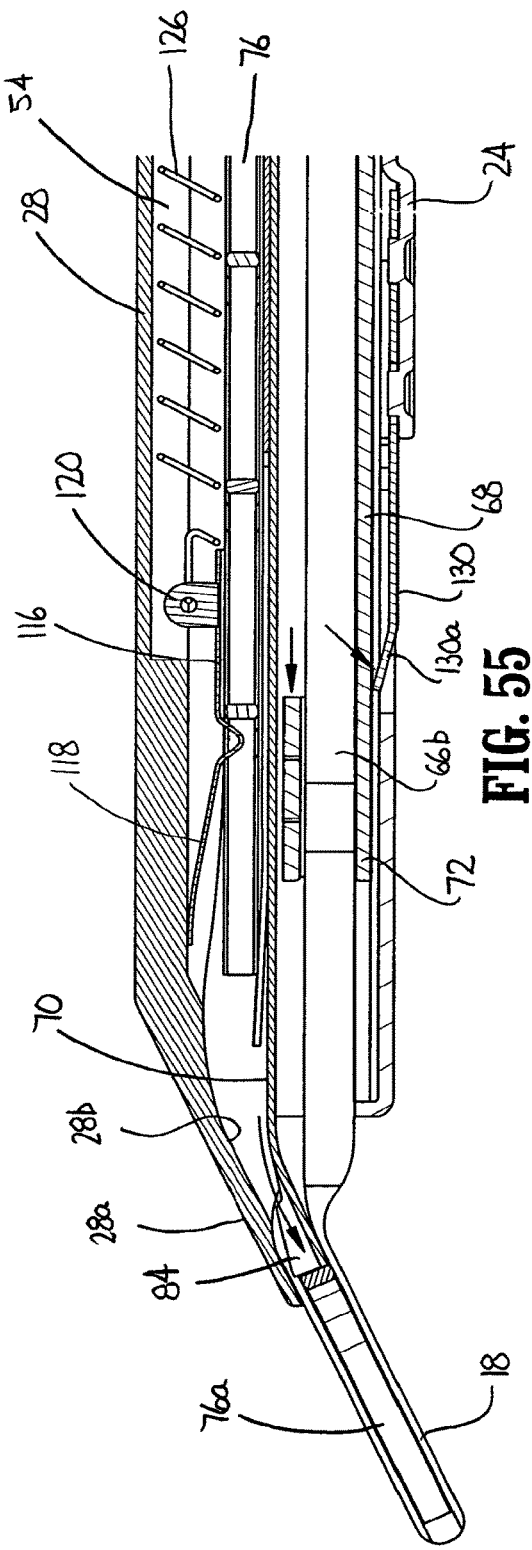
FIG. 54
FIG. 55

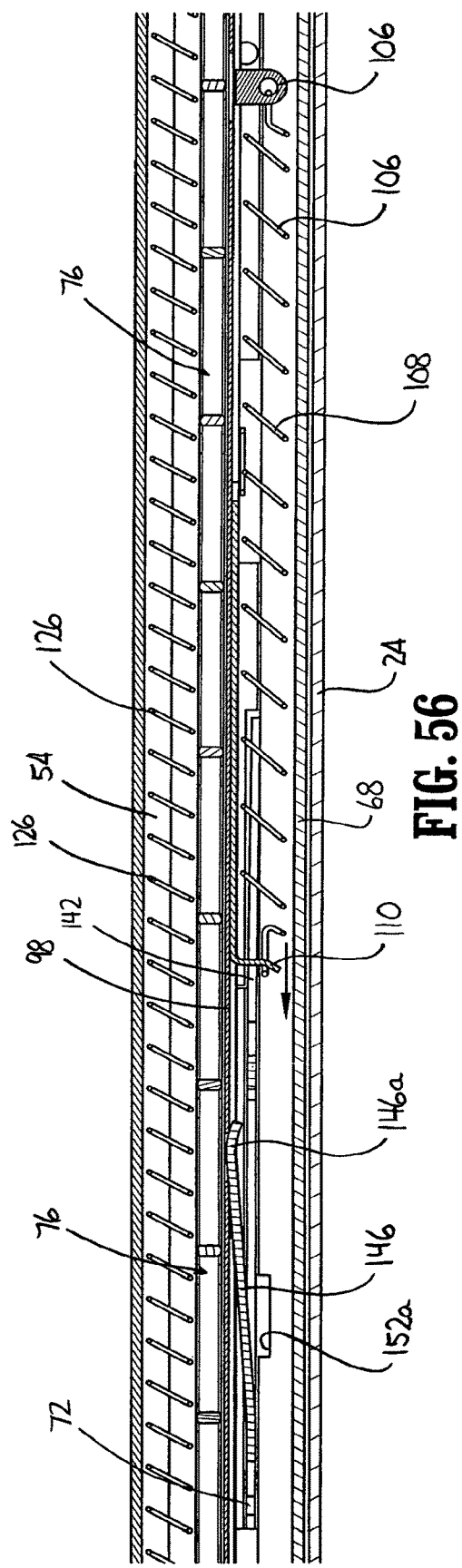
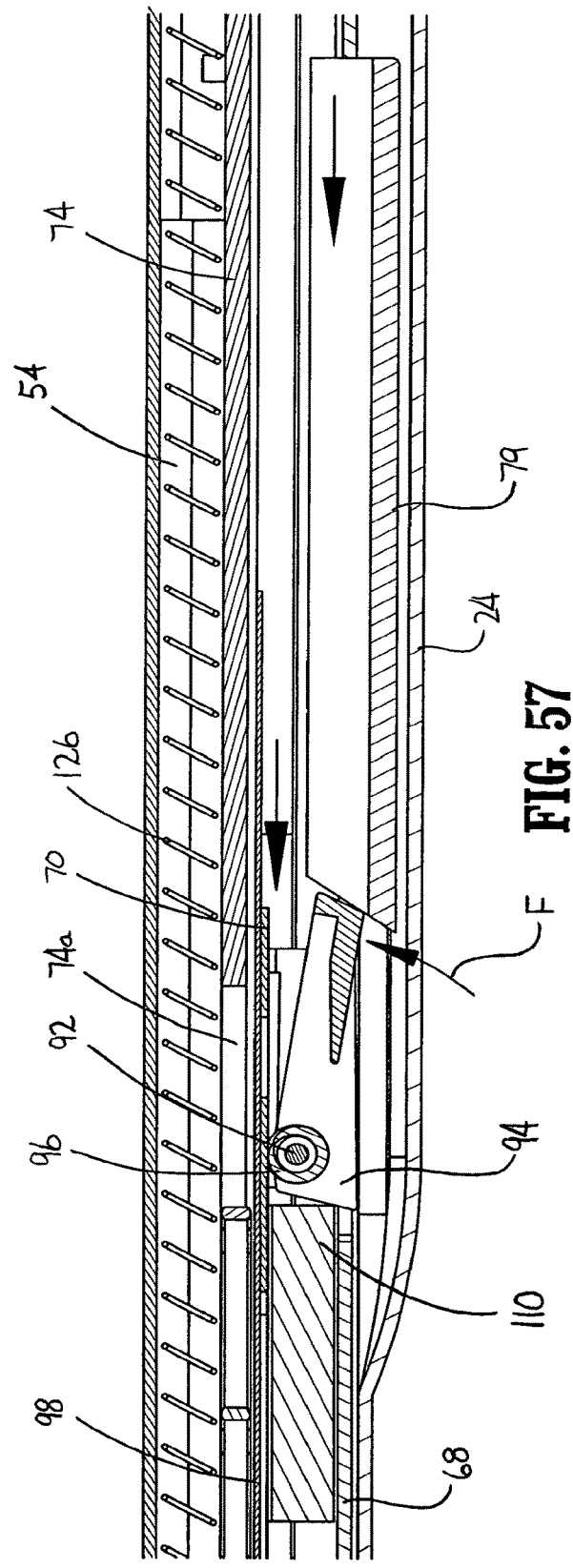
FIG. 56
FIG. 57

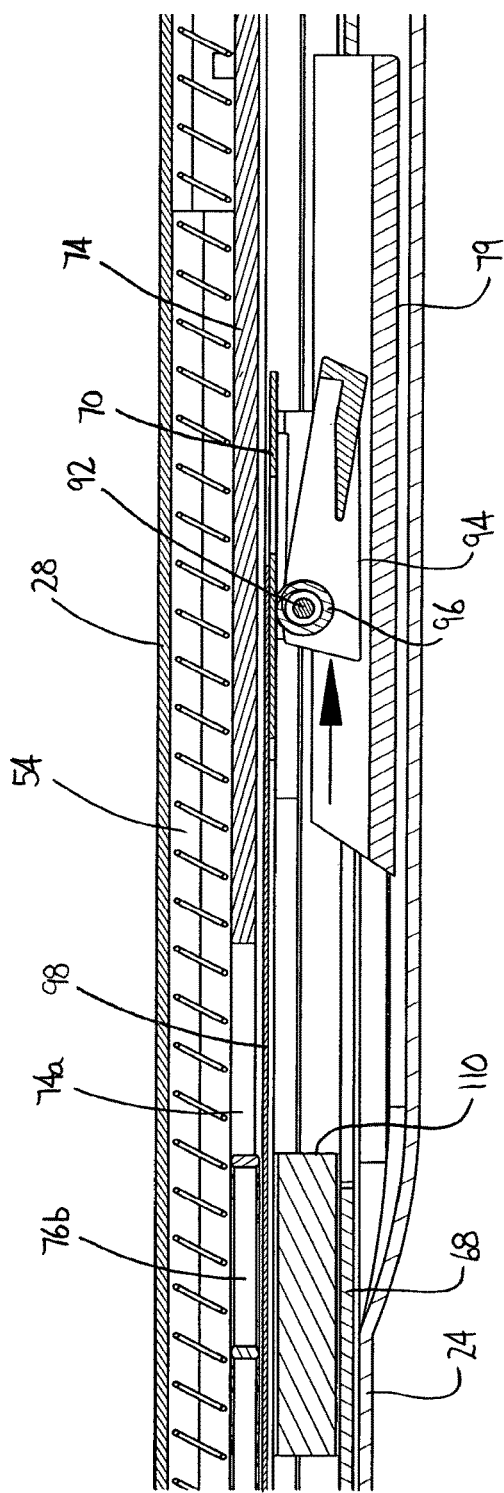
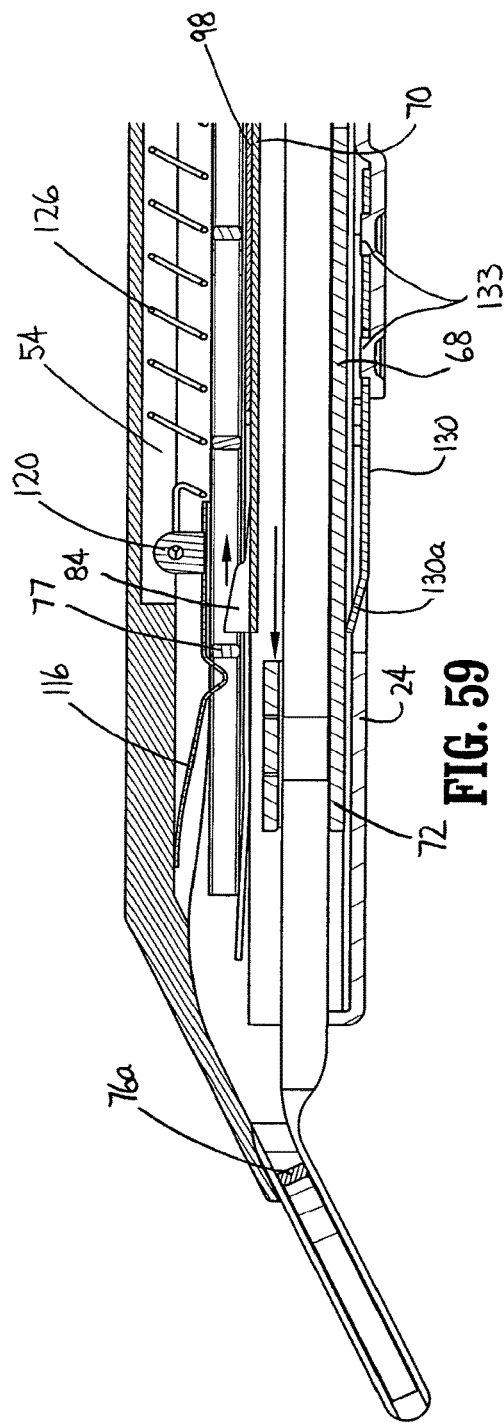
FIG. 58
FIG. 59

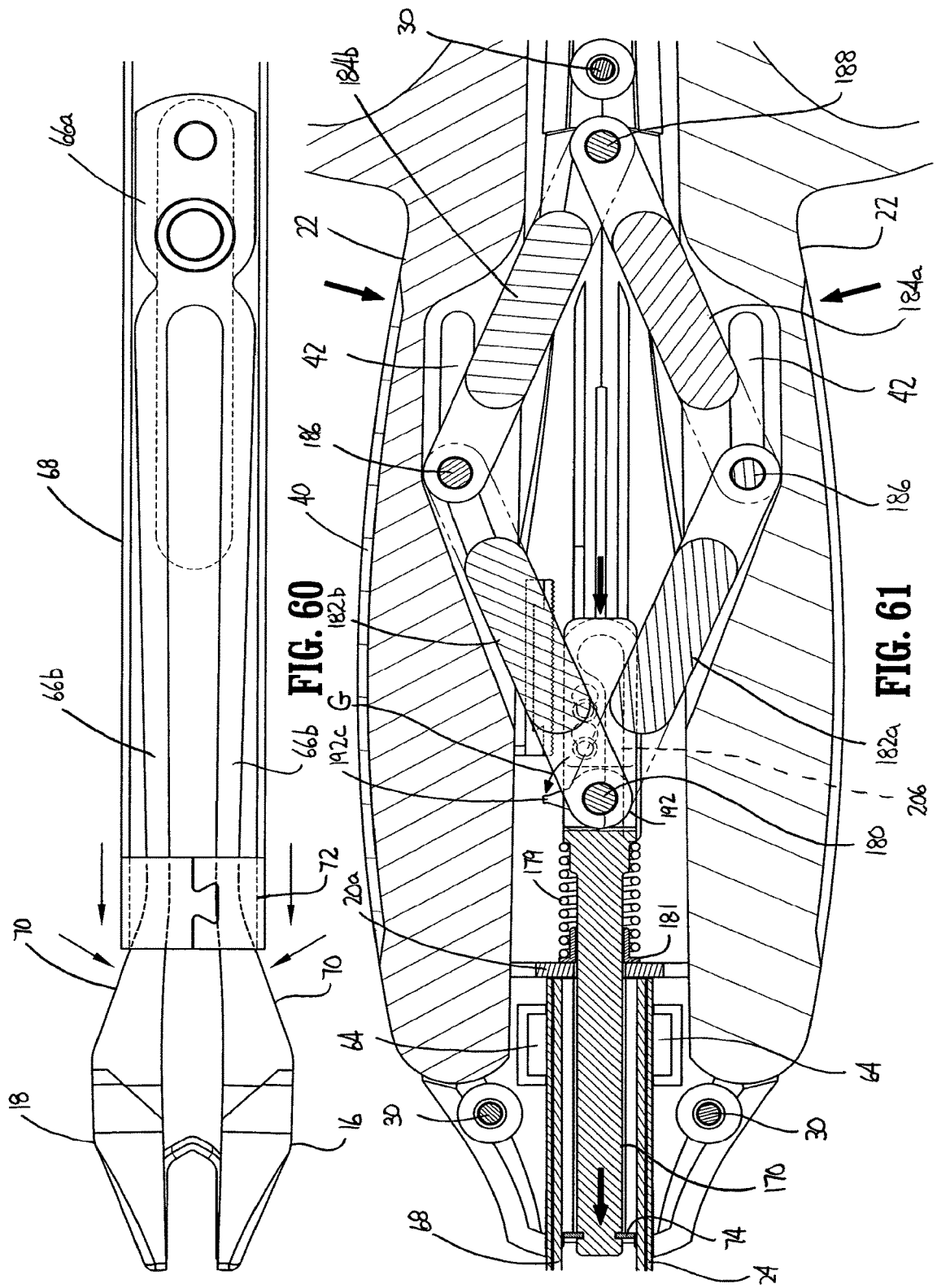

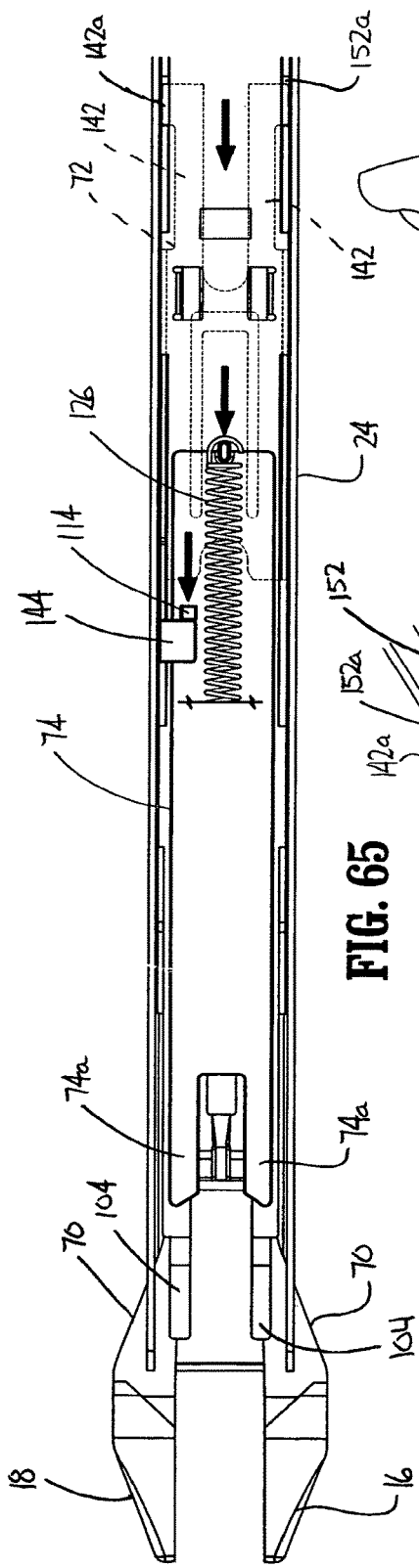
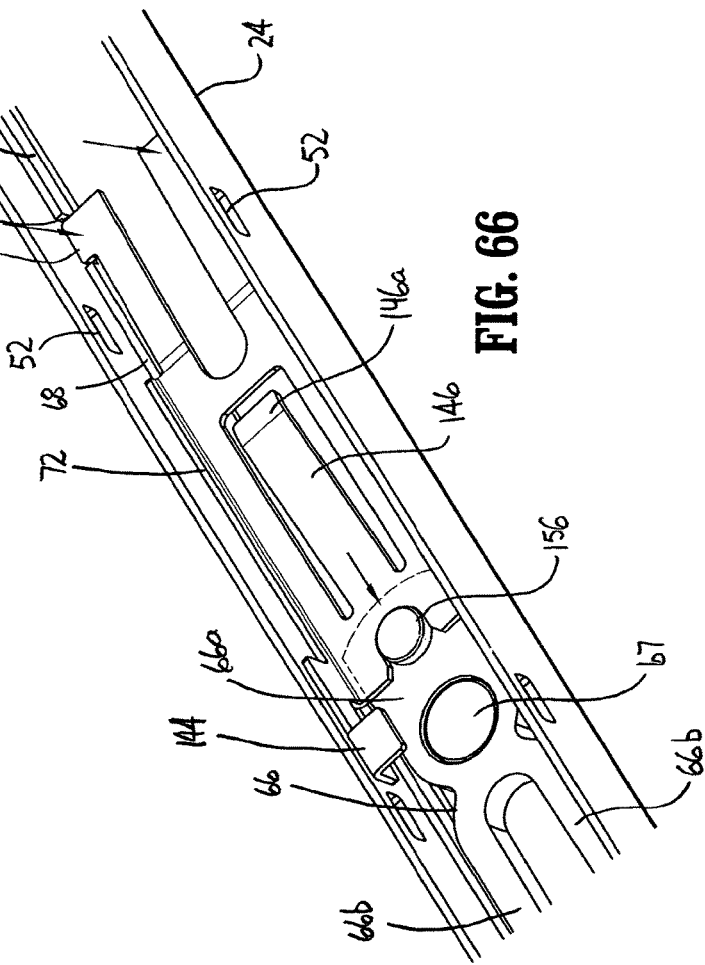
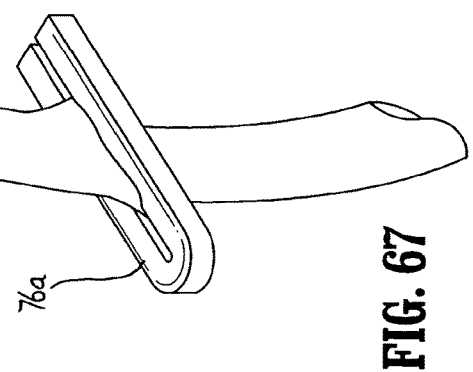
FIG. 65
FIG. 66
FIG. 67

APPARATUS FOR APPLYING SURGICAL CLIPS

CROSS REFERENCE TO RELATED APPLICATIONS

This application is a continuation of U.S. application Ser. No. 14/551,546, filed Nov. 24, 2014, which is a continuation of U.S. application Ser. No. 11/245,866, filed Oct. 7, 2005, now U.S. Pat. No. 8,920,438, which claims the benefit of U.S. Provisional application Ser. No. 60/617,017, filed Oct. 8, 2004, the entire contents of each of which are incorporated herein by reference.

TECHNICAL FIELD

This present disclosure relates generally to an apparatus for applying surgical clips to tissue. More specifically, the present disclosure relates to an apparatus for applying a series of clips to tissue seriatim.

BACKGROUND

Surgical procedures frequently require ligation of blood vessels, severed tissues and/or other organs to control or stop bleeding. Clip applying apparatus for quickly applying a surgical clip about tissue are well known. Such clip applying apparatus include single clip applicators and multiple clip applicators. In single clip applicators, a new clip is loaded into the apparatus after application of each clip. Multiple clip applicators include a series of clips which can be sequentially applied to tissue during the course of a surgical procedure. Because surgical procedures usually require the use of a multiplicity of surgical clips, multiple clip applicators are generally preferred.

Typically, clip applying apparatus include a handle mechanism, an elongated body portion, and a clip crimping assembly, e.g., a jaw or pair of jaws. Such clip applying apparatus are configured for endoscopic or open surgical procedures. Although known clip applying apparatus for sequentially advancing individual clips have provided good results, a continuing need exists for a clip applying apparatus which is less complex and provides effective hemostasis.

SUMMARY

In accordance with the present disclosure, an apparatus for applying surgical clips is provided which includes a handle portion including a housing and at least one movable handle and a body portion housing a clip stack. A pair of jaws is supported at the distal end of the body portion. The body portion includes a clip pusher, a camming member and a clip follower. The clip pusher is movably positioned within the body portion and is operable to advance a distal-most clip from the clip stack to a position between the pair of jaws. The camming member is movably positioned within the body portion and is operable to approximate or move the pair of jaws toward each other to deform the distal-most clip of the clip stack. The clip follower is positioned proximally of the clip stack and is operable to urge the clip stack distally towards the pair of jaws. In one embodiment, the body portion includes a lockout member and a stop member. The lockout member is movable from a first position in slidable relation to the camming member to a second position interlocked with the camming member. In its second position, the lockout member is positioned to abut the stop member to limit distal movement of the camming member.

In one embodiment, the lockout member includes at least one flexible leg having a projection and the camming member includes at least one slot dimensioned to receive the projection to interlock or secure the lockout member to the camming member. The at least one flexible leg can include a pair of flexible legs and the at least one slot can include a pair of slots.

The lockout member can include a resilient finger which is positioned to releasably retain the lockout member in its first position. In one embodiment, the body portion further includes a separator plate which includes an opening dimensioned to receive a portion of the resilient finger of the lockout member to retain the lockout member in its first position. The clip follower may include a tab and the lockout member may include an engagement member such that the tab is movable into the engagement member to move the lockout member from its first position to its second position. In one embodiment, the tab is positioned to engage the engagement member after the proximal most clip has been advanced to the pair of jaws. Alternately, the tab can be positioned to engage the engagement member when one or more clips are remaining in the apparatus.

In one embodiment, an apparatus for applying surgical clips is provided which includes a handle portion having at least one movable handle and a body portion including a clip pusher and a camming member. The clip pusher is movably supported within the body portion to advance a distal-most clip of a clip stack to a position between a pair of jaws supported at a distal end of the body portion. The camming member is movably supported within the body portion from a retracted position to an advanced position to approximate the pair of jaws. A latch assembly is supported on the clip pusher and includes a pivotal latch member which is movable from a first position engaged with an abutment supported on the camming member to a second position disengaged from the abutment of the camming member. The camming member is operably connected to the at least one movable handle such that movement of the at least one movable handle through an actuation stroke effects movement of the camming member from its advanced position to its retracted position. In one embodiment, the pivotal latch member is urged towards its first position by a biasing member such that movement of the camming member from its retracted position to its advanced position initially effects advancement of the clip pusher. A latch cam is fixedly supported on the body portion and is positioned to engage the pivotal latch member after the clip pusher has advanced the distal-most clip of the clip stack to its position between the jaws to disengage the latch member from the abutment. In one embodiment, a biasing member is positioned to urge the clip pusher to a retracted position after the latch member is disengaged from the abutment. In one embodiment, the body portion includes a housing body and a housing cover and the latch cam is supported on the housing cover. The handle portion can include a yoke which is connected to a proximal end of the camming member. In one embodiment, the at least one handle is operably connected to the yoke by at least one front link such that movement of the at least one handle through an actuation stroke effects advancement of the yoke and the camming member. The handle portion can include a pair of handles with each handle operably connected to the yoke by one front link. In one embodiment, a pair of rear links are provided. Each of the rear links has a first end pivotally connected to a respective front link by a first pivot member and a second end pivotally connected to the handle portion by a second pivot member. Each of the pair of handles defines a cam channel for slidably receiving a respective one of the first pivot members.

In one embodiment, an apparatus for applying surgical clips includes a handle portion, a body portion extending distally from the handle portion, and a jaw body supported at a distal end of the body portion. The jaw body includes first and second jaws movable from a spaced position to a more approximated position. In one embodiment, the body portion includes a camming member which is movable from a retracted position to an advanced position to effect movement of the first and second jaws from their spaced position to their more approximated position. The body portion further includes a resilient jaw locking member removably positioned between the first and second jaws to prevent the jaws from moving from their spaced position to their more approximated position. In one embodiment, the jaw locking member is in the form of a resilient plate and the jaw body includes a pair of inwardly deformable legs. Each of the legs supports one of the first and second jaws and the locking member being positioned between the legs of the jaw body. A distal end of the camming is slidably positioned about the legs of the jaw body and is movable from its retracted position to its advanced position to move the locking member from between the legs of the jaw body and subsequently to effect movement of the first and second jaws to their more approximated position.

BRIEF DESCRIPTION OF THE DRAWINGS

Various embodiments of the presently disclosed clip applying apparatus are described herein with reference to the drawings, wherein:

FIG. 1 is a perspective view of one embodiment of the presently disclosed clip applying apparatus;

FIG. 2 is an enlarged perspective view of the distal end of the clip applying apparatus shown in FIG. 1;

FIG. 3 is a top view of the clip applying apparatus shown in FIG. 1;

FIG. 4 is a side view of the clip applying apparatus shown in FIG. 1;

FIG. 5 is a perspective view of the proximal portion of the clip applying apparatus shown in FIG. 4 with the top housing half-section exploded;

FIG. 6 is a perspective view of the clip applying apparatus shown in FIG. 1 with the top housing half-section removed;

FIG. 7 is an enlarged view of the indicated area of detail shown in FIG. 6;

FIG. 10 is an exploded view of the body portion of the clip applying apparatus shown in FIG. 1;

FIG. 12 is an enlarged view of the indicated area of detail shown in FIG. 12;

FIG. 13 is a bottom perspective view of the housing cover of the clip applying apparatus shown in FIG. 1;

FIG. 14 is an enlarged view of the indicated area of detail shown in FIG. 13;

FIG. 15 is an enlarged view of the indicated area of detail shown in FIG. 13;

FIG. 18 is a bottom perspective view of the separator plate of the clip applying apparatus shown in FIG. 1;

FIG. 19 is an enlarged view of the indicated area of detail shown in FIG. 18;

FIG. 20 is a bottom perspective view of the clip pusher of the clip applying apparatus shown in FIG. 1;

FIG. 21 is a bottom perspective view of the housing body of the clip applying apparatus shown in FIG. 1;

FIG. 29 is a perspective view of the body portion of the clip applying apparatus shown in FIG. 1 with the housing cover removed;

FIG. 30 is an enlarged perspective view of the distal end of the body portion shown in FIG. 29;

FIG. 31 is an enlarged perspective view of the proximal end of the body portion shown in FIG. 29;

FIG. 32 is an enlarged perspective view of the distal end of the body portion shown in FIG. 29 with the clip follower biasing member and the clip stop member removed;

FIG. 33 is an enlarged perspective view of the distal end of the body portion shown in FIG. 32 with the clip stack removed;

FIG. 34 is an enlarged perspective view of the distal end of the body portion shown in FIG. 33 with the separator plate shown removed;

FIG. 35 is an enlarged perspective view of the distal end of the body portion shown in FIG. 34 with the clip pusher removed;

FIG. 38 is an enlarged view of the indicated area of detail shown in FIG. 36;

FIG. 39 is an enlarged view of the indicated area of detail shown in FIG. 37;

FIG. 40 is an enlarged view of the indicated area of detail shown in FIG. 37;

FIG. 41 is an enlarged view of the indicated area of detail shown in FIG. 36;

FIG. 44 is an enlarged view of the indicated area of detail shown in FIG. 37;

FIG. 45 is an enlarged view of the indicated area of detail shown in FIG. 36;

FIG. 52 is a side cross-sectional view of the proximal portion of the body portion of the clip applying apparatus shown in FIG. 1 during initial actuation of the handle portion.

FIG. 53 is a side cross-sectional view of the distal end of the body portion of the clip applying apparatus shown in FIG. 1 during initial actuation of the handle portion;

FIG. 54 is a side cross-sectional view of the distal end of the body portion of the clip applying apparatus shown in FIG. 1 during further actuation of the handle portion;

FIG. 55 is a side cross-sectional view of the distal end of the body portion of the clip applying apparatus shown in FIG. 1 during further actuation of the handle portion;

FIG. 56 is a side cross-sectional view of the body portion shown in FIG. 42 after further actuation of the handle portion;

FIG. 57 is a side cross-sectional view of the body portion shown in FIG. 44 after further actuation of the handle portion;

FIG. 58 is a side cross-sectional view of the body portion shown in FIG. 57 after further actuation of the handle portion;

FIG. 59 is a side cross-sectional view of the distal end of the body portion shown in FIG. 55 after further actuation of the handle portion;

FIG. 60 is a top view of the jaw body and camming member shown in FIG. 46 with the camming member advanced further distally;

FIG. 61 is a top cross-sectional view of the handle portion shown in FIG. 51 with the handle portion after further actuation of the handle portion;

FIG. 65 is a top view of the distal portion of the body portion of the clip applying apparatus shown in FIG. 36 illustrating the lockout tab of the clip follower engaging the engagement member of the lockout;

FIG. 66 is top perspective view of a portion of the body portion of the clip applying apparatus shown in FIG. 36 illustrating the lockout engaging the stop member; and FIG. 67 is a perspective view of a clip of the clip stack of the clip applying apparatus shown in FIG. 36 deformed about tissue.

DETAILED DESCRIPTION

Figure 8:
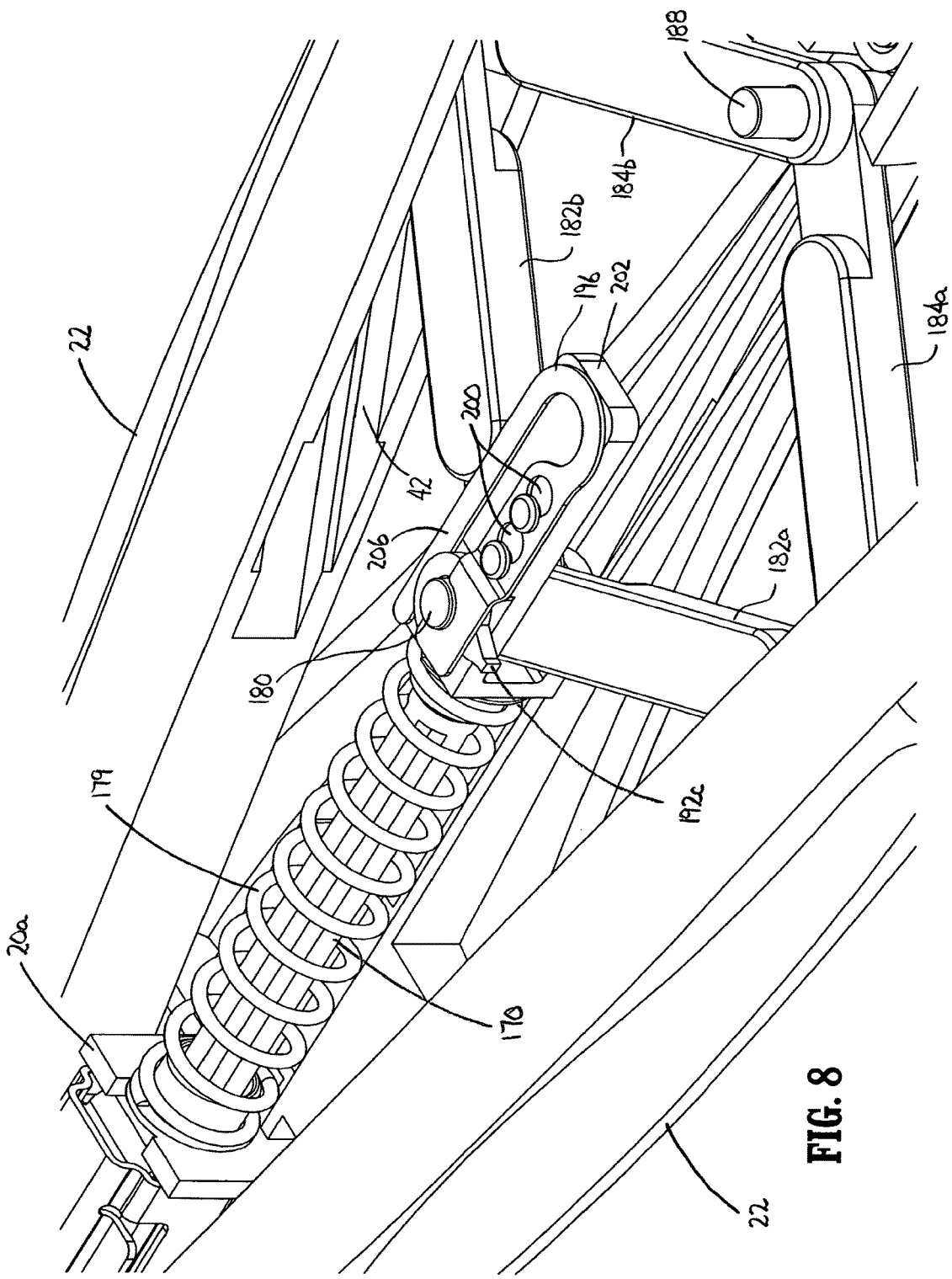
FIG. 8 is an enlarged view of the indicated area of detail shown in FIG. 6.

Embodiments of the presently disclosed surgical clip applier will now be described in detail with reference to the drawings wherein like reference numerals designate identical or corresponding elements in each of the several views. Throughout this description, the term "proximal" will refer to the portion of the instrument closest to the operator and the term "distal" will refer to the portion of the instrument furthest from the operator.

Referring to FIGS. 1-4, the presently disclosed surgical clip applier, shown generally as 10, includes a handle portion 12, an elongated body portion 14 extending distally from handle portion 12 and first and second jaws 16 and 18 which extend from the distal end of body portion 14. Briefly, handle portion 12 includes a handle housing 20 and a pair of movable handles or triggers 22. Each handle 22 includes a finger loop 22a for receiving a finger of a surgeon's hand.

Referring also to FIGS. 5-9, handle housing 20 can be formed from molded housing half-sections 20a and 20b (FIG. 5) which are secured together using screws 30 and nuts 32. Alternately, other fastening techniques may be used to secure housing half-sections 20a and 20b together, e.g., welding, rivets, interlocking structure, adhesives, etc. In one embodiment, the distal end of each handle 22 is pivotally secured about a pivot member 34 such that handles 22, when actuated, move in a scissor-like manner. Each pivot member 34 is positioned between recesses 36a and 36b formed in half-sections 20a and 20b, respectively, and may be formed integrally with a respective handle 22 or, in the alternative, as a separate element from a respective handle 22. In one embodiment, each handle 22 has a slip resistant grip member 40 secured to an outside surface thereof and a cam channel 42 formed on an inside surface thereof. Slip resistant grip member 40 can be formed from a cushioning material and overmolded onto each handle 22. It is also contemplated that other slip resistant materials and methods of application may be used to form grip member 40 and apply grip member 40 to a handle 22. Each cam channel 42 is configured to receive a pivot member for connecting a pair of pivotal links as will be described in more detail below.

Referring to FIG. 10, elongated body portion 14 includes a housing body 24 defining a channel 26 for receiving internal components of surgical clip applier 10. A housing cover 28 is secured to housing body 24 and covers channel 26. In one embodiment, housing cover 28 has a series of projections 50 which are dimensioned to be received within openings 52 formed along channel walls 26a of housing body 24 to secure housing cover 28 to housing body 24. Alternately, other securement techniques are contemplated, e.g., adhesives, crimping, screws, etc.

Referring also to FIGS. 13-15, an internal surface of housing cover 28 includes a first longitudinal groove 54 and a second longitudinal groove 56. Grooves 54 and 56 accommodate other components of the elongated body portion as will be discussed in further detail below. The distal end of housing cover 28 includes an outer surface 28a which is tapered or angled downwardly towards housing body 24. Angled outer surface 28a provides easier access to tissue and reduces the likelihood of the clip applier snagging tissue during use. An inner surface 28b formed on the distal end of housing cover 28 has a curvature which corresponds to the curvature of a top surface of jaws 16 and 18. Inner surface 28b is positioned in abutting relation to jaws 16 and 18 to provide stability to and prevent misalignment of jaws 16 and 18 during operation of clip applier 10.

Referring to FIGS. 10 and 21, housing body 24 includes a pair of distally located cutouts 60 configured to slidably receive jaws 16 and 18. Cutouts 60 are dimensioned to confine jaws 16 and 18 to prevent misalignment of the jaws during actuation of clip applier 10 (FIG. 30). The proximal end of housing body 24 includes a pair of transversely extending wings 62 which are dimensioned to be received within recesses 64 formed in housing half-sections 20*a* and 20*b* (FIG. 9) to secure elongated body portion 14 to handle portion 12.

Figure 23:
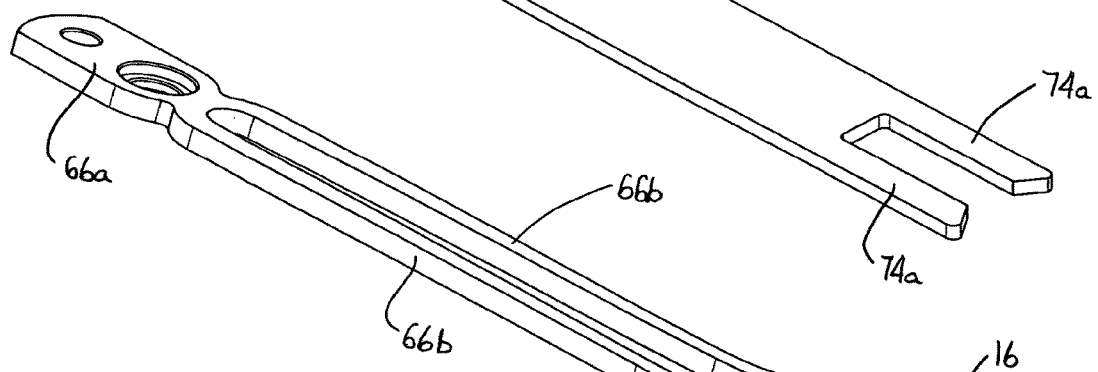
FIG. 23 is a top perspective view of the jaw body of the clip applying apparatus shown in FIG. 1.

As illustrated in FIG. 10, the internal components of clip applier 10 include a jaw body 66, a camming member 68, a clip pusher 70, a clip pusher lockout 72, a clip stack follower 74, and a clip stack 76 including a distal-most clip 76*a* and a proximal-most clip 76*b*. Referring also to FIG. 23, jaw body 66 includes jaws 16 and 18, a proximal mounting portion 66*a* and a pair of spaced distally extending legs 66*b*. Each of jaws 16 and 18 is supported on a distal end of a respective one of legs 66*b* and includes a clip channel 16*a* and 18*a*, respectively. A cam surface 70 is formed on an outer surface of each jaw 16 and 18. Cam surfaces 70 are positioned to be engaged by camming member 68 (FIG. 10) in a manner to be described in further detail below. Jaw body 66 is mounted within channel 26 of housing body 24 using a bolt 67 or the like. Bolt 67 extends through an opening 66*d* in body 66 and through housing body 24.

Figure 16:
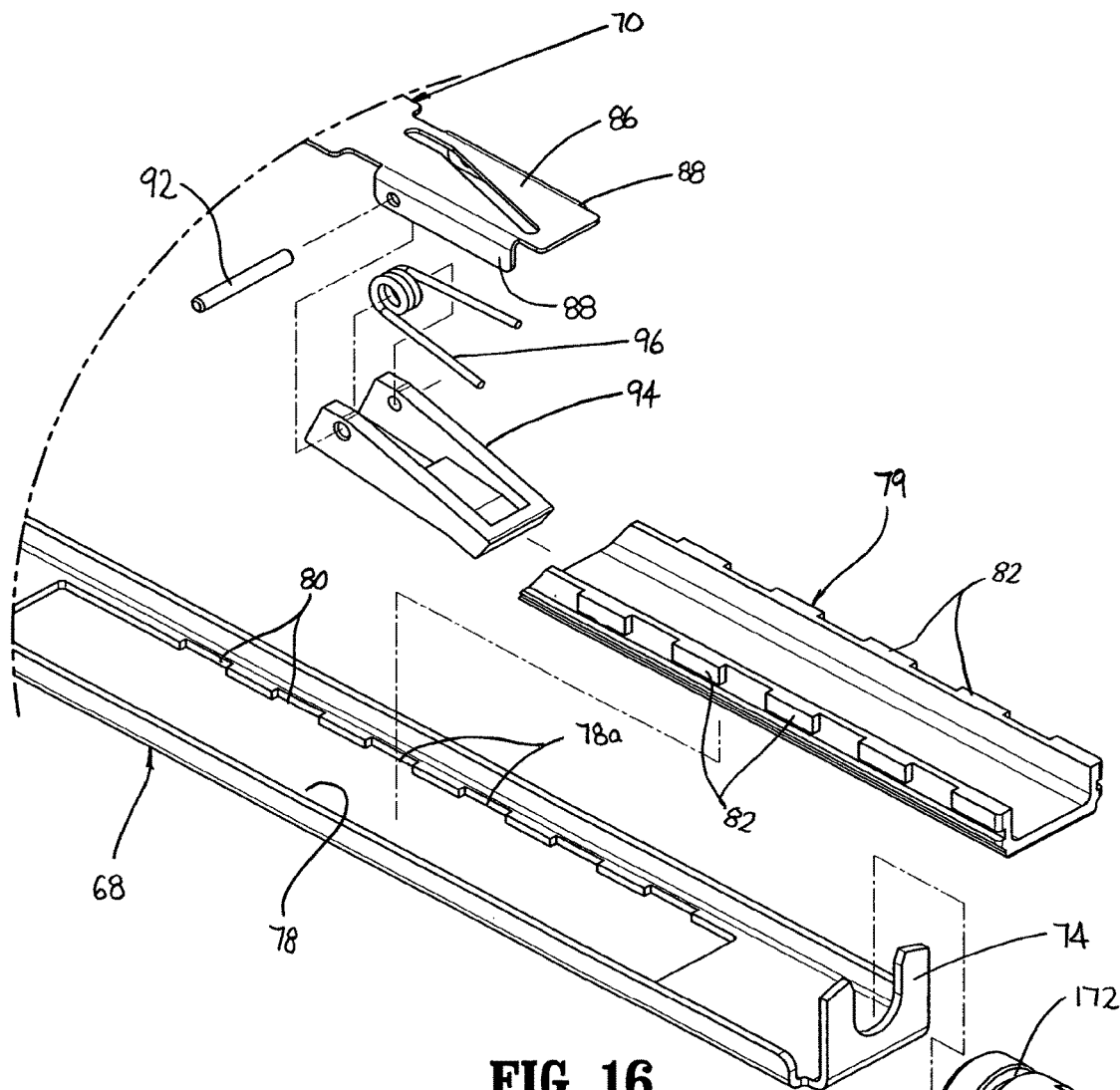
FIG. 16 is an enlarged view of the indicated area of detail shown in FIG. 10.
Figure 17:
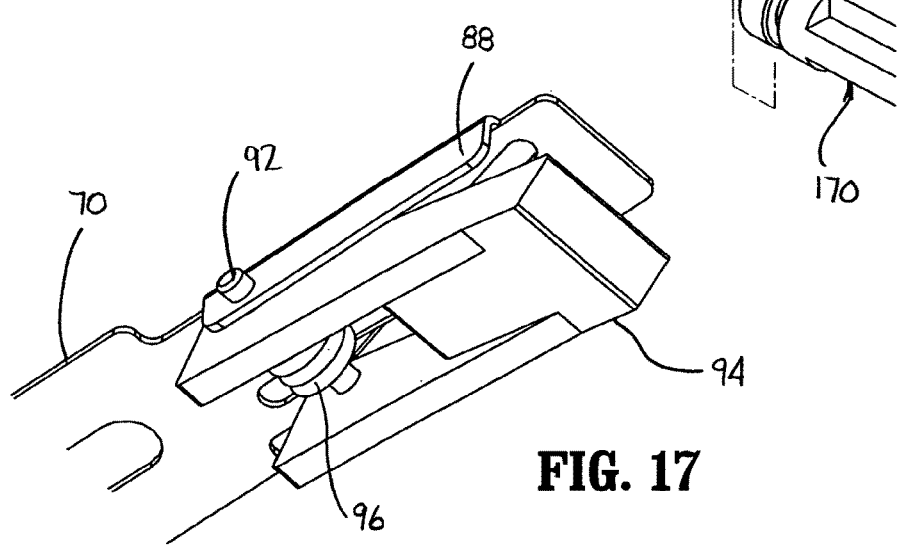
FIG. 17 is a perspective view of the proximal end of the clip pusher of the clip applying apparatus shown in FIG. 1 with the pusher latch assembly secured thereto.
Figure 46:
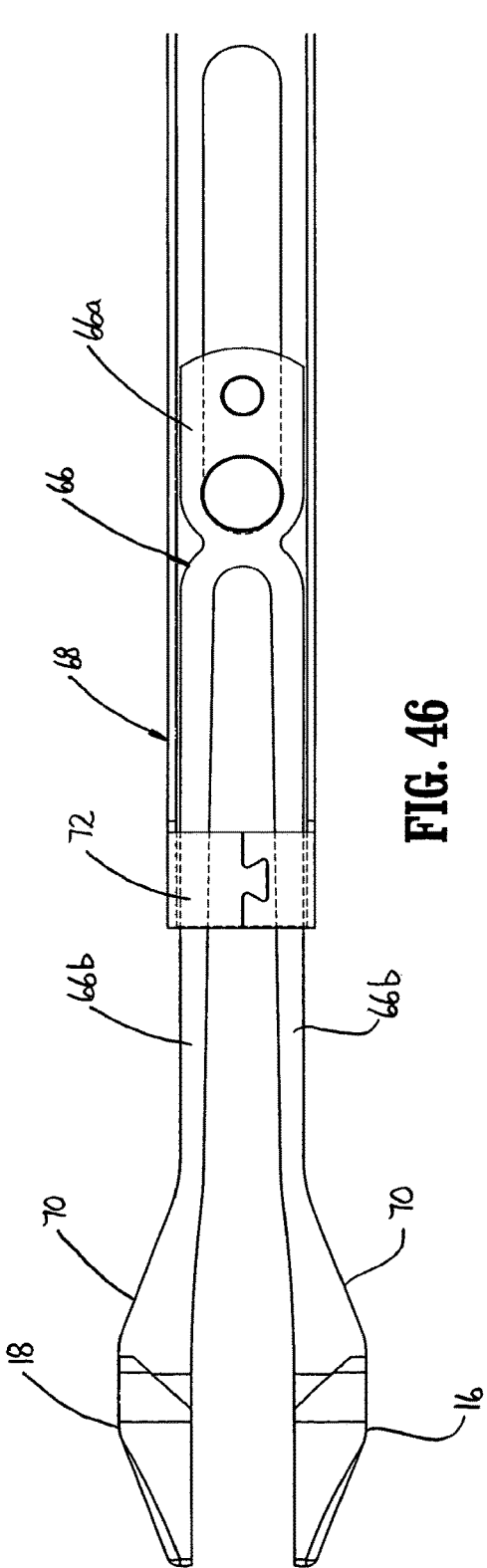
FIG. 46 is a top view of the jaw body and the distal end of the camming member of the clip applying apparatus shown in FIG. 36.
Figure 48:
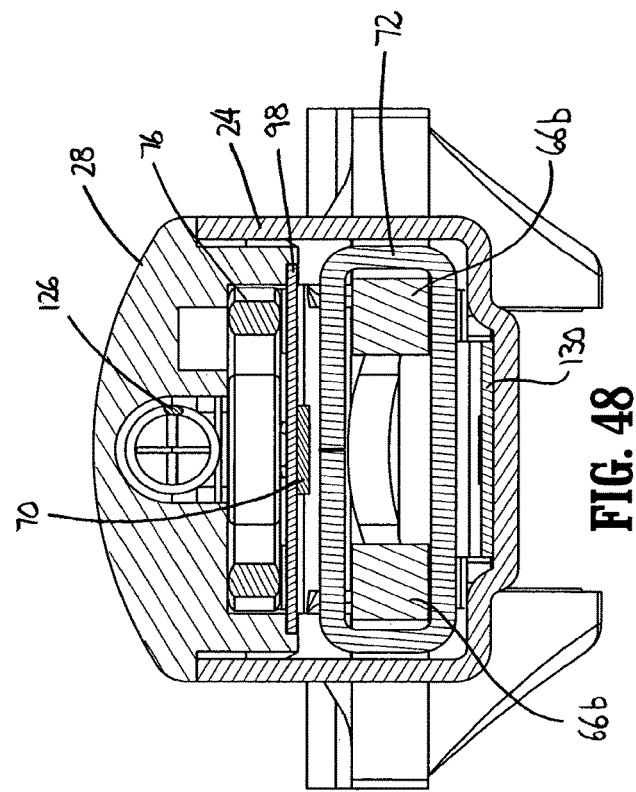
FIG. 48 is a cross-sectional view taken along section lines 48-48 of FIG. 40.
Figure 47:
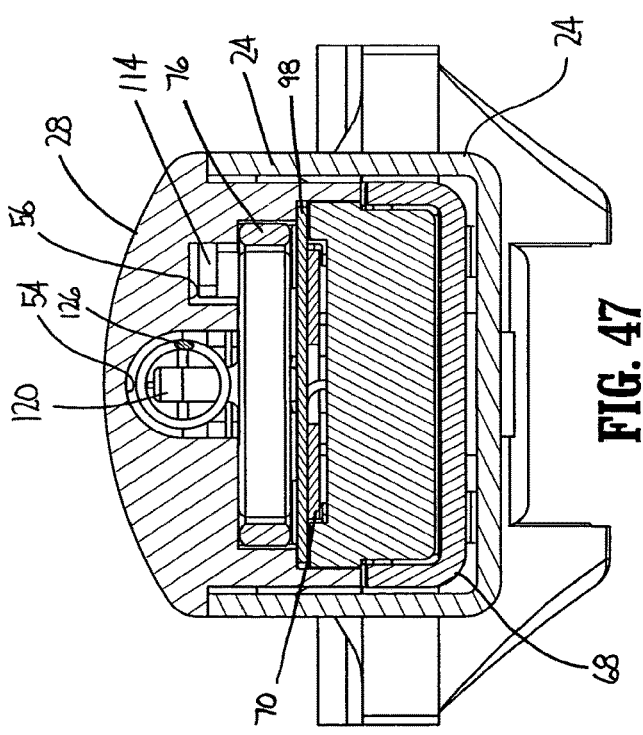
FIG. 47 is a cross-sectional view taken along section lines 47-47 of FIG. 44.
Figure 49:
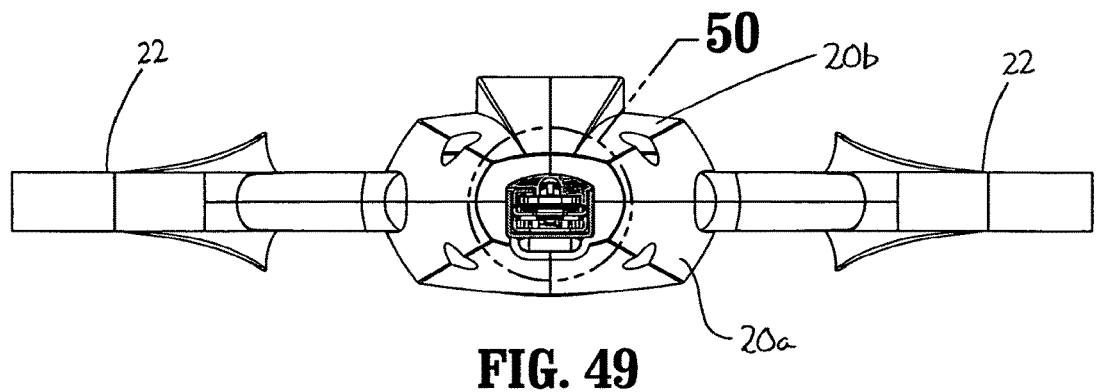
FIG. 49 is a cross-sectional view taken along section lines 49-49 of FIG. 42.
Figure 50:
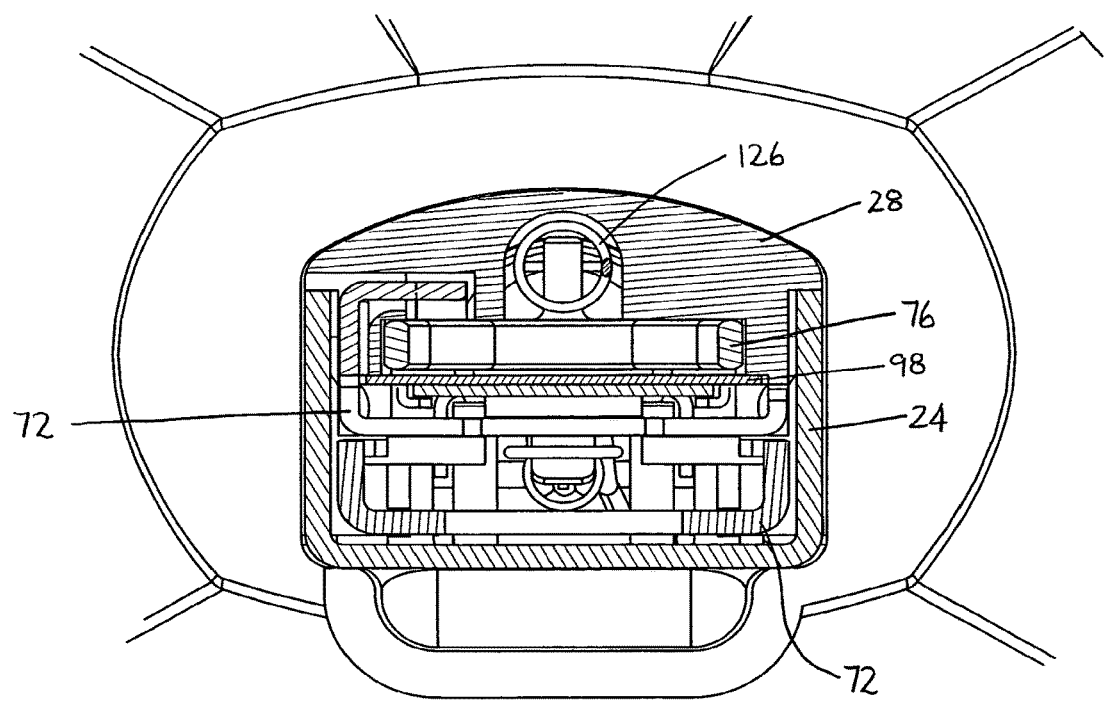
FIG. 50 is an enlarged view of the indicated area of detail shown in FIG. 49.

Referring now to FIGS. 10 and 16, camming member 68 is slidably supported within channel 26 (FIG. 10) of housing body 24 and includes a distal engagement member 72 which is positioned about legs 66*b* of jaw body 66 (FIG. 48). Engagement member 72 can have a substantially rectangular configuration. Alternately, other configurations are contemplated, e.g., C-shaped configuration. The proximal end of camming member 68 includes a bracket 74 to operably connect camming member 68 to handle portion 12 as will be discussed in further detail below. Handles 22 of handle portion 12 (FIG. 1) are operable to move camming member 68 between a retracted position and an advanced position along channel 26 of housing body 24. In the retracted position of camming member 68, engagement member 72 is positioned about legs 66*b* of jaw body 66 at a location proximal of cam surfaces 70 (FIG. 46). In the advanced position of camming member 68, engagement member 72 is positioned about jaws 16 and 18 in abutting relation to cam surfaces 70 (FIG. 60).

The proximal end of camming member 68 supports an abutment member 79. In one embodiment, abutment member 79 is supported within a cutout 78 formed in the proximal end of camming member 68. Cutout 78 includes a plurality of grooves 78*a* which receive tongues or projections 82 formed on abutment member 79 to secure abutment member 79 to camming member 68. It is contemplated that abutment member 79 may be attached to camming member 68 using other known fastening techniques. Alternately, abutment member 79 can be formed integrally with camming member 68. Abutment member 79 is positioned to engage a pusher latch assembly 80, as will be described in detail below.

Referring to FIGS. 10, 16, 17 and 20, clip pusher 70 includes an elongated body 82, a distal finger 84, and a proximal latch assembly mount 86. Distal finger 84 is semi-circular in shape and is positioned to engage distal-most clip 76*a* of the stack of clips 76 when clip pusher 70 is moved from a retracted position to an advanced position (FIG. 53). Latch assembly mount 86 includes a pair of spaced, vertical brackets 88. Brackets 88 each include an opening 90 for receiving a pivot pin 92 (FIG. 16) of pusher latch assembly 80.

Pusher latch assembly 80 includes a latch member 94, a biasing member 96, and pivot pin 92. Latch member 94 is pivotally secured at its distal end between brackets 88 of clip pusher 70 about pivot pin 92. Biasing member 96 is positioned between the proximal end of clip pusher 70 and latch member 94 to urge the proximal end of latch member 94 away from clip pusher 70 to a position to engage abutment member 79 when camming member 68 is moved from its retracted to its advanced position. Latch member 94 is pivotal against the urging of biasing member 96 towards the proximal end of clip pusher 70 to move latch member 94 out of engagement with abutment member 79 as will be discussed in further detail below.

Referring to FIGS. 10 and 18, a separator plate 98 is fixedly supported between housing body 24 and housing cover 28. Separator plate 98 includes a series of projections 100 which are received within recesses 102 formed in housing cover 28 to secure separator plate 98 to housing cover 28. The distal end of separator plate 98 includes a pair of spaced spring fingers 104 which are positioned to guide the distal-most clip 76*a* of clip stack 76 into jaws 16 and 18. A biasing member securement member 106 (FIG. 19) is formed on separator plate 98. A biasing member, which can be a coil spring 108, has one end secured to securement member 106 of separator plate 98 and a second end secured to a securement member 110 (FIG. 20) formed on clip pusher 70. Coil spring 108 is in tension and urges clip pusher 70 to its retracted position. When handles 22 (FIG. 1) are operated to move camming member 68 from its retracted position to its advanced position, abutment member 79 engages latch member 94 to move latch member 94 and clip pusher 70 distally toward its advanced position against the urging of coil spring 108. As clip pusher 70 moves distally with camming member 68, distal finger 82 of clip pusher 70 engages distal-most clip 76*a* of clip stack 76 to advance distal-most clip 76*a* into jaws 16 and 18.

Referring to FIGS. 10 and 12, a pusher latch cam 110 is supported in channel 26 between housing body 24 and housing cover 28. Pusher latch cam 110 includes a pair of tabs 110*a* which are received within recesses 112 formed in housing cover 28 to fixedly secure pusher latch cam 110 in relation to housing cover 28. Pusher latch cam 110 is positioned in channel 26 at a position to engage the distal end of latch member 94 (FIG. 57) to pivot and disengage latch member 94 from abutment member 79 when distal-most clip 76*a* has been fully advanced into jaws 16 and 18. When latch member 94 is disengaged from abutment member 79, coil spring 108 returns clip pusher 70 to its retracted position. Although pusher latch cam 110 is illustrated as block shaped, other configurations are envisioned. Further, pusher latch cam may be integrally formed with housing cover 28 or housing body 24.

Figure 22:
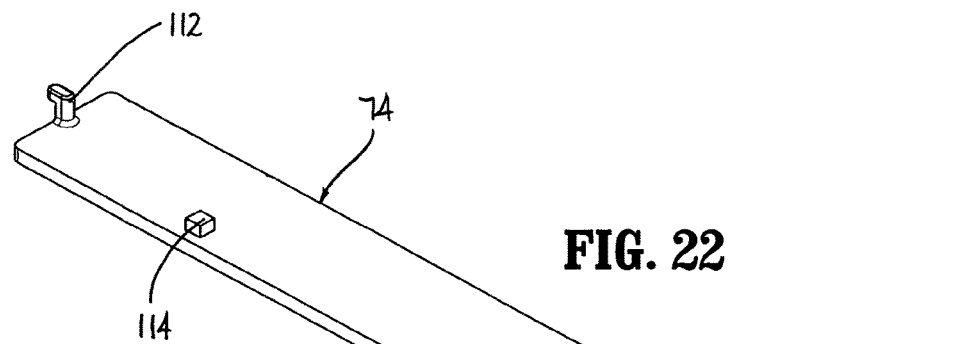
FIG. 22 is a top perspective view of the clip follower of the clip applying apparatus shown in FIG. 1.

Referring to FIGS. 10 and 22, clip stack 76 is slidably supported on a top surface of separator plate 98. A clip follower 74 is positioned behind the proximal-most clip 76*b* of clip stack 76. Clip follower 74 includes a pair of distally extending arms 74*a*. The distal end of each arm 74*a* is configured to engage the backspan of proximal-most clip 76*b*. A top surface of clip follower 74 includes a spring securement member 112 and a lockout tab 114. Lockout tab 114 is positioned to travel in second longitudinal groove 56 (FIG. 14) of housing cover 28 and is movable with clip follower 74 as clip follower 74 is advanced to move clip stack 76 distally within elongated body portion 14.

Figure 11:
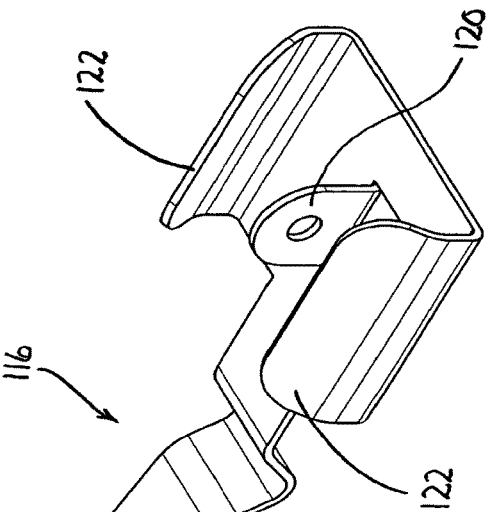
FIG. 11 is a perspective view of the clip stop member of the clip applying apparatus shown in FIG. 1.
Figure 9:
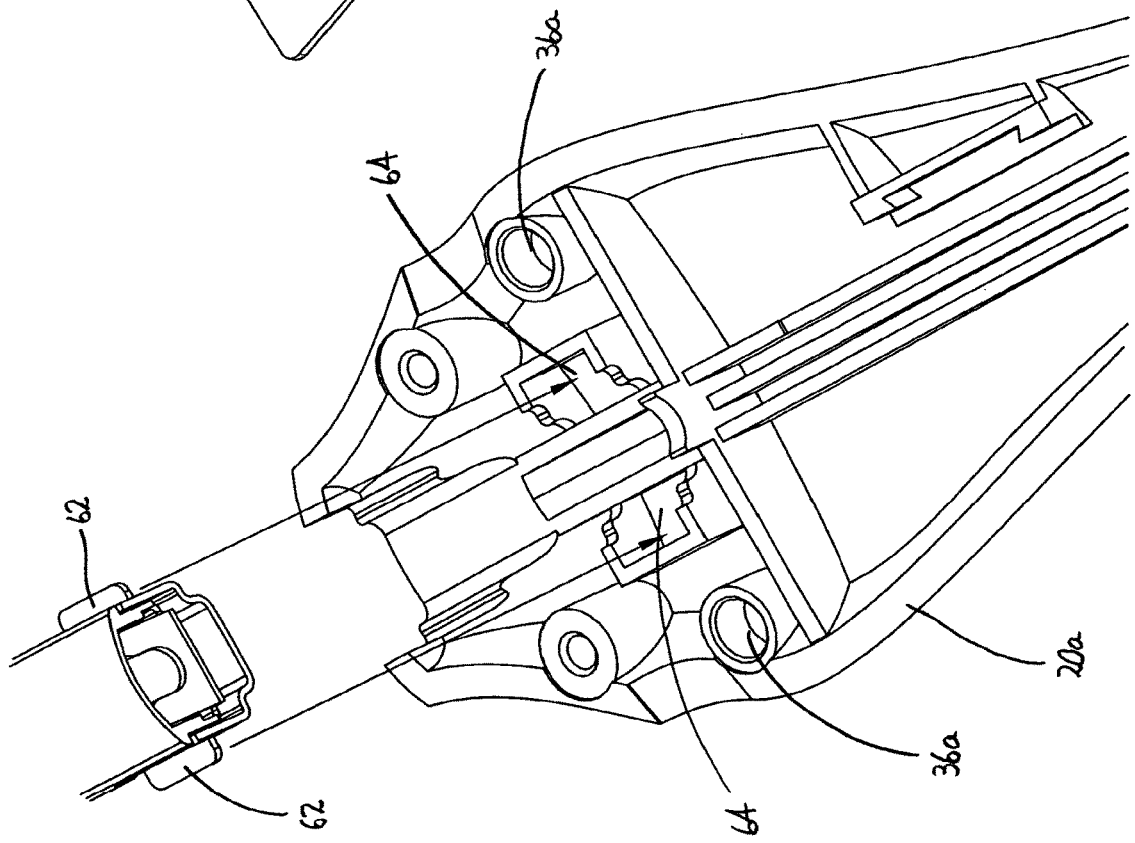
FIG. 9 is a perspective view of the proximal end of the body portion and the interior of a housing half-section with the internal components of the handle portion removed.

Referring to FIGS. 10 and 11, a clip stop member 116 includes a spring arm 118, a spring securement member 120 and a pair of anchor members 122. Anchor members 122 are dimensioned to be snap-fit into a pair of openings 124 formed through a distal portion of housing cover 28 to secure clip stop member 116 to the underside of housing cover 28. A biasing member 126 extends between spring securement member 120 of clip stop member 116 and spring securement member 112 of follower 74. Biasing member 126, which can be a coil spring, is supported in tension between follower 74 and clip stop member 116 to urge follower 74 and clip stack 76 distally within body portion 14 towards jaws 16 and 18. Biasing member 126 is positioned within first longitudinal groove 54 of housing cover 28 (FIG. 14). Clip stop member 116 prevents distal-most clip 76a from being pushed distally into jaws 16 and 18 until clip pusher 70 is moved to its advanced position. When clip pusher 70 is moved to its advanced position, clip stop member 116 is deflected upwardly by movement of distal-most clip 76a (FIG. 53).

A jaw locking member, e.g., plate 130 (FIG. 10) is secured to housing body 24 within channel 26 of housing body 24. Jaw locking plate 130 includes openings 131 which are dimensioned to receive projections 133 (FIG. 59) formed on housing body 24 to secure plate 130 to body 24. Jaw locking plate 130 has a resilient and flexible arm 130a which is positioned between legs 66b of jaw body 66 to prevent jaws 16 and 18 from being closed inadvertently during positioning of clip applier 10 at a surgical site. When camming member 68 is moved to its advanced position, the distal end of engagement member 72 of camming member 68 deflects arm 130a downwardly to move arm 130a from between jaws 16 and 18 and allow for closure of jaws 16 and 18 (FIG. 59). Alternately, the jaw locking member need not be in the form of a flat plate but rather other configurations are envisioned, e.g., cylindrical or any configuration positionable between jaws 16 and 18 to prevent closure of the jaws.

Figure 24:
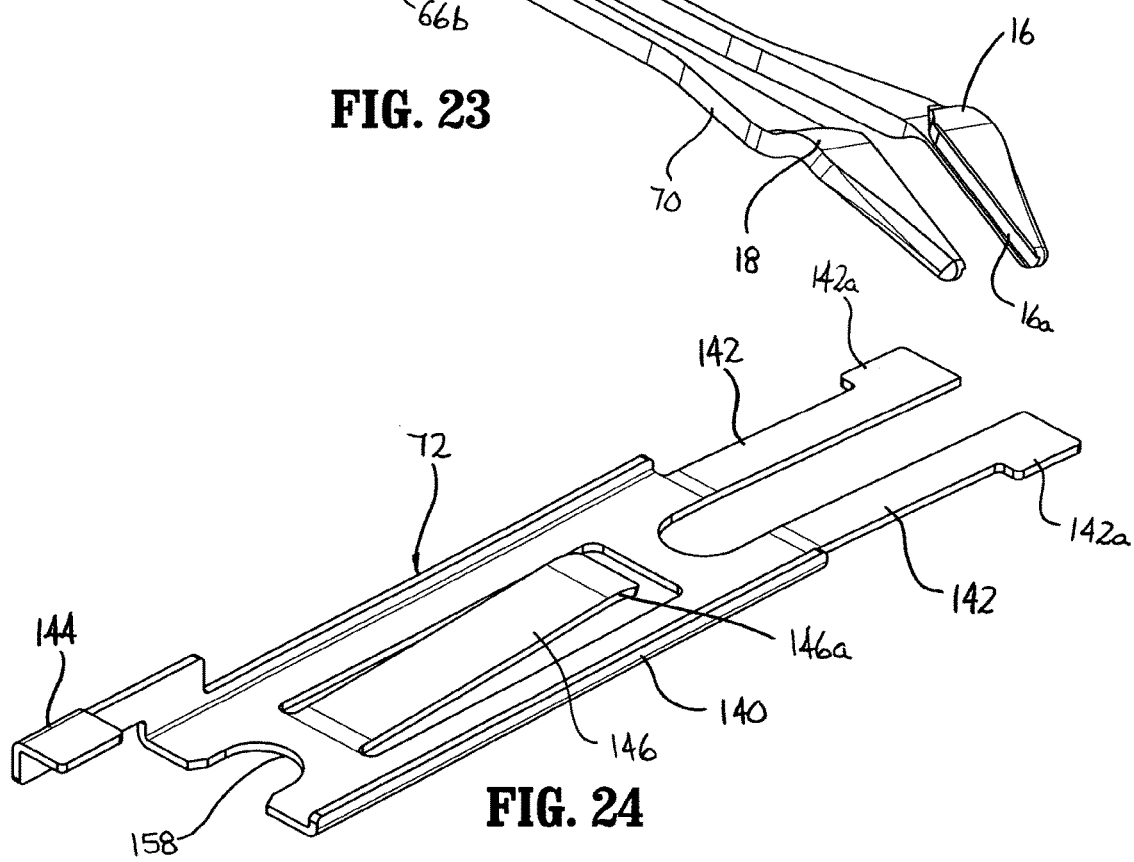
FIG. 24 is a top perspective view of the clip applying apparatus shown in FIG. 1.

Referring to FIGS. 10 and 24, a lockout member 72 is positioned above camming member 68 within channel 26 of housing body 24. Lockout member 72 includes a central body portion 140, a pair of flexible legs 142 and a distally extending engagement member or flag 144. Central body portion 140 includes a proximally extending resilient finger 146 which extends upwardly towards separator plate 98 and includes a downwardly curved end 146a. End 146a is positioned to extend through an elongated slot 148 formed in clip pusher 70 and to be partially received within an opening 150 formed in separator plate 98. Engagement of end 146a of finger 146 in opening 150 of separator plate 98 releasably retains lockout 72 at a fixed position in relation to separator plate 98 until an external force is applied to engagement member 144 as will be discussed in detail below.

Each of flexible legs 142 of lockout 72 includes a radial projection 142a. Legs 142 are positioned within the confines of sidewalls 152 of camming member 68 and are urged inwardly by sidewalls 152. A pair of slots 152a are formed in sidewalls 152 such that when projections 142a are moved into alignment with slots 152a, legs 142 spring outwardly to move radial projections 142a into slots 152a. When projections 142a are positioned within slots 152a, lockout 72 is fixedly secured to camming member 68.

As discussed above, follower 74 is urged distally by biasing member 126 to urge clip stack 76 distally along separator plate 98. As each clip 76a is advanced into jaws 16 and 18, follower 74 moves further distally within elongated body 14. As the proximal-most clip 76b is advanced in jaws 16 and 18, lockout tab 114 of follower 74 engages engagement member or flag 144 of lockout 72 and effects distal movement of lockout 72 in relation to camming member 68, such that after proximal-most clip 76b is crimped between jaws 16 and 18 and camming member 68 is returned to its retracted position, radial projections 142a align with slots 152a in camming member 68 to fixedly secure lockout 72 to camming member 68.

A stop member 156 (FIG. 10) is secured to a proximal end of mounting portion 66a of jaw body 66. In one embodiment, stop member 156 includes a cylindrical dowel. Alternately, other stop member configurations are envisioned. The distal end of lockout 72 includes a recess 158 for receiving stop member 156. Since stop member 156 is fixedly secured within channel 26 of housing body 24, engagement between lockout 72 and stop member 156 prevents further distal advancement of lockout 72. As discussed above, after the proximal-most clip 76b has been applied to tissue, lockout 72 is fixedly secured to camming member 68. Stop member 156 is also received in recess 158 of lockout 72. Thus, after proximal-most clip 76b has been applied to tissue and lockout 72 is fixed to camming member 86, engagement between lockout 72 and stop member 156 prevents distal advancement of camming member 68. As will be discussed below, since camming member 68 is connected via linkages to handles 22 (FIG. 1), engagement between lockout 72 and stop member 156 will prevent actuation of handles 22 and thus, indicate to a surgeon that the clip applier clip stack 76 has been depleted.

Figure 51:
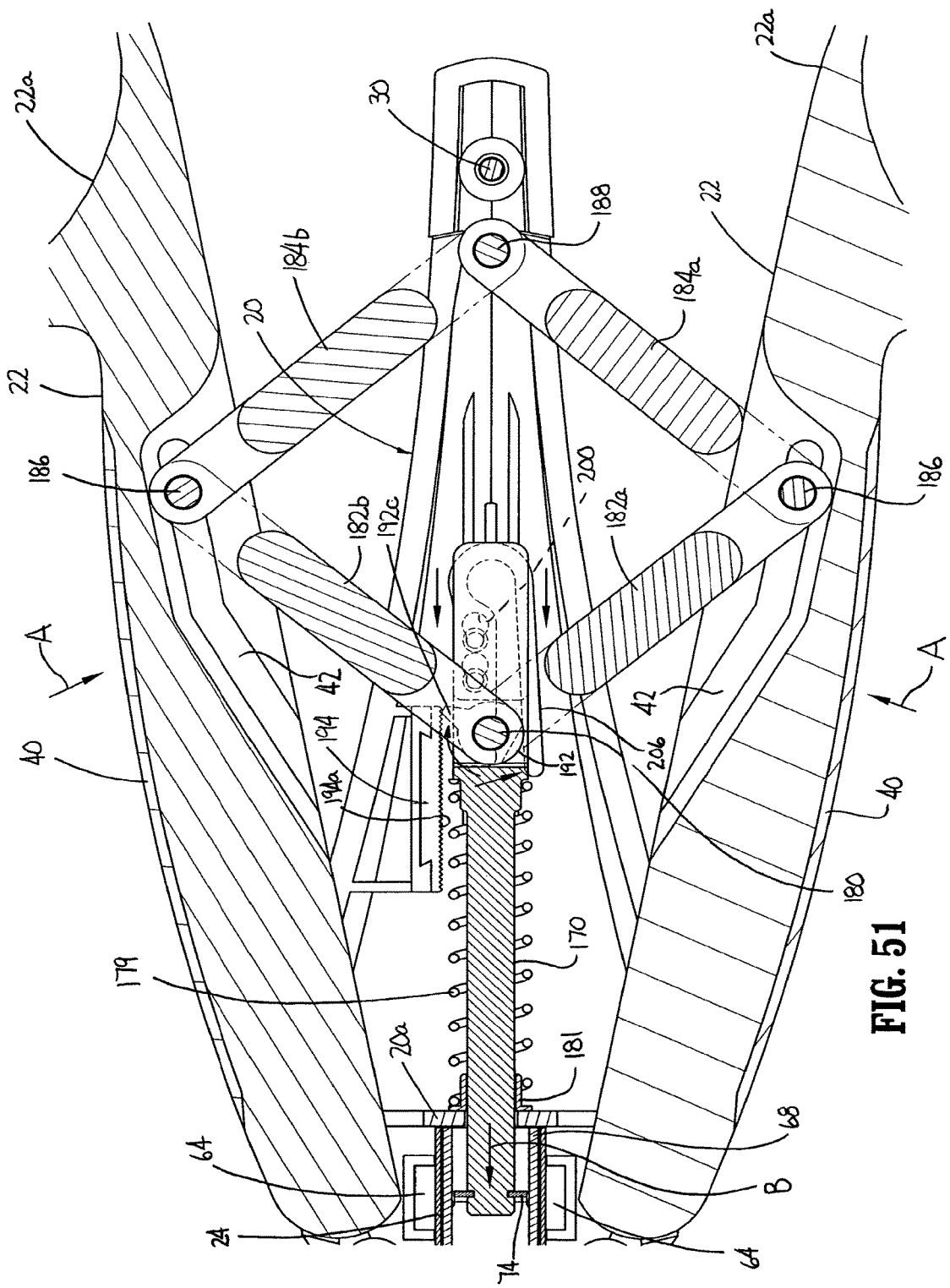
FIG. 51 is a top cross-sectional view of the handle portion of the clip applying apparatus shown in FIG. 1 during initial actuation of the handle portion.

Referring to FIGS. 5, 8, 25 and 28, handle portion 12 includes a yoke 170 which is slidably positioned between housing half-sections 20a and 20b between retracted and advanced positions. The distal end of yoke 170 includes an annular recess 172 which is dimensioned to be positioned in a semi-circular slot 174 (FIG. 16) formed in bracket 74 of camming member 68 to attach yoke 170 to camming member 68. The proximal end of yoke 170 includes a U-shaped connector 176 having a throughbore 178 dimensioned to receive a pivot pin 180. Pivot pin 180 pivotally connects yoke 170 to the distal end of front links 182a and 182b of a linkage assembly which connects handles 22 to yoke 170. The proximal end of front links 182a and 182b are pivotally secured to the distal end of rear links 184a and 184b, respectively, by pivot members 186. The proximal ends of rear links 184a and 184b are connected to each other and to handle housing 20 by a pivot member 188. Pivot member 188 is pivotally mounted between bores 190 formed in housing half-sections 20a and 20b (FIG. 5). Pivot members 186 are received within a respective cam channel 42 formed in a respective handle 22. When handles 22 are actuated, i.e., moved towards housing 20, pivot members 186 are caused to move through cam channels 42 such that front links 182a, 182b and rear links 184a, 184b are moved from a first misaligned position towards an aligned position (FIG. 51). Since the proximal end of rear links 184a and 184b are axially fixed between housing half-sections 20a and 20b, movement of front links 182a and 182b and rear links 184a and 184b toward an aligned position moves the distal end of front links 182a and 182b distally within housing 20. As discussed above, the distal end of front links 182a and 182b is axially fixed to yoke 170 by pivot member 180. As such, when handles 22 are actuated, yoke 170 is moved distally to move camming member 68 distally. A biasing member, e.g., coil spring 179, is positioned about a distal end of yoke 170 and abuts a spring stop 181 supported within housing 20 to urge yoke 170 to its retracted position.

Figure 25:
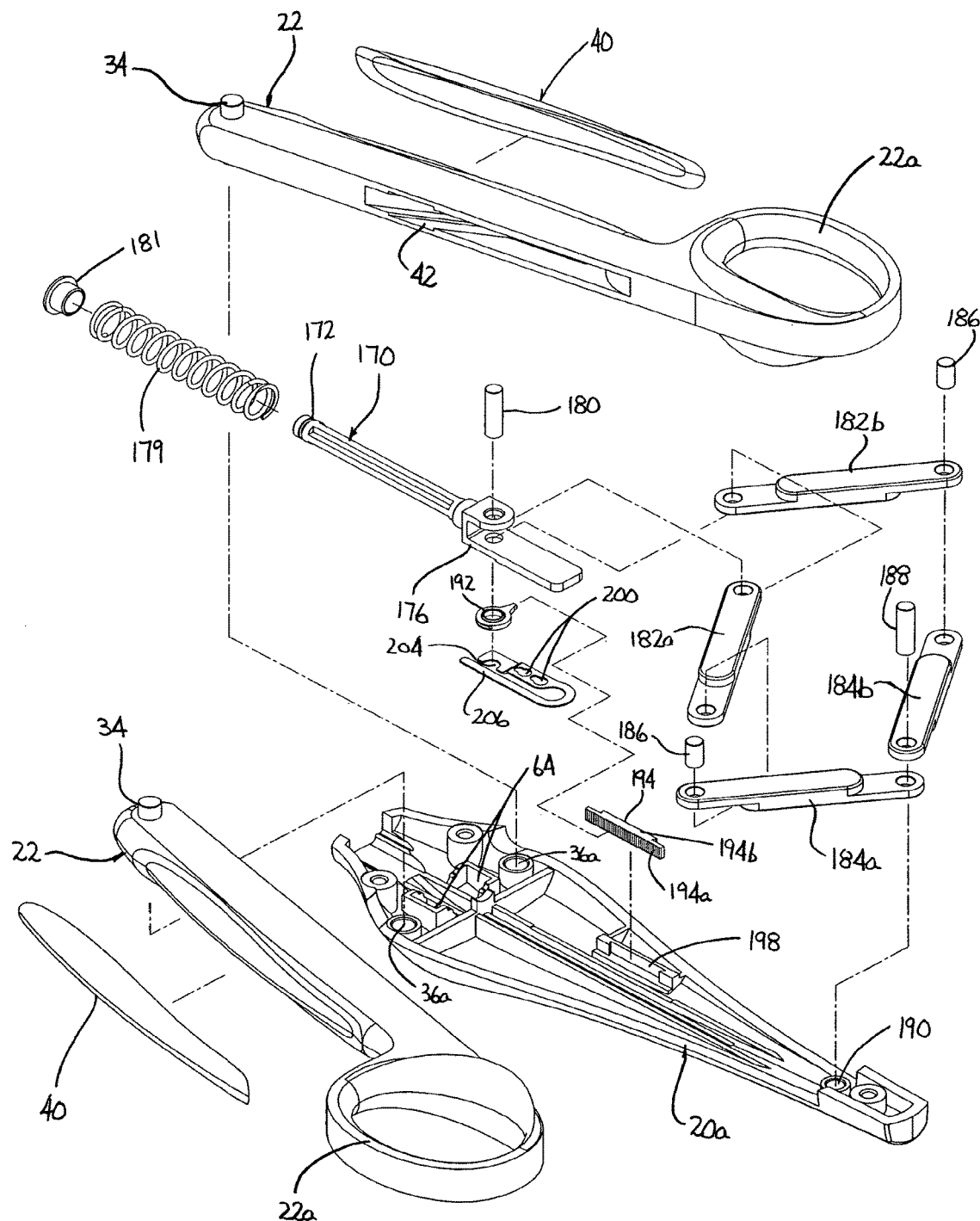
FIG. 25 is an exploded perspective view of the handle portion of the clip applying apparatus shown in FIG. 1.
Figure 26:
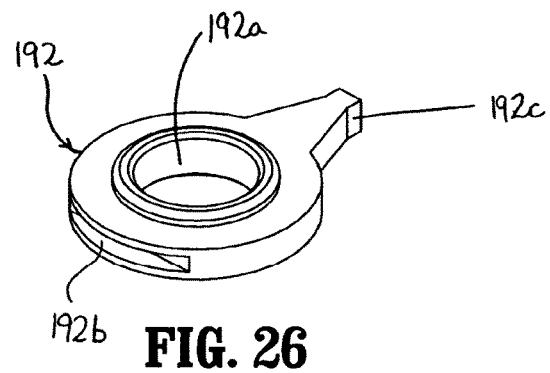
FIG. 26 is a perspective view of the pawl of the handle portion shown in FIG. 25.
Figure 27:
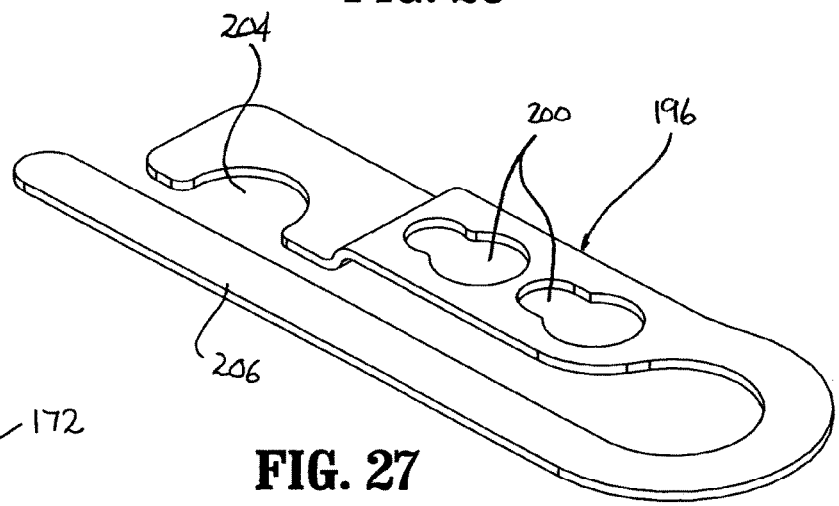
FIG. 27 is a perspective view of the pawl biasing member of the handle portion shown in FIG. 25.
Figure 28:
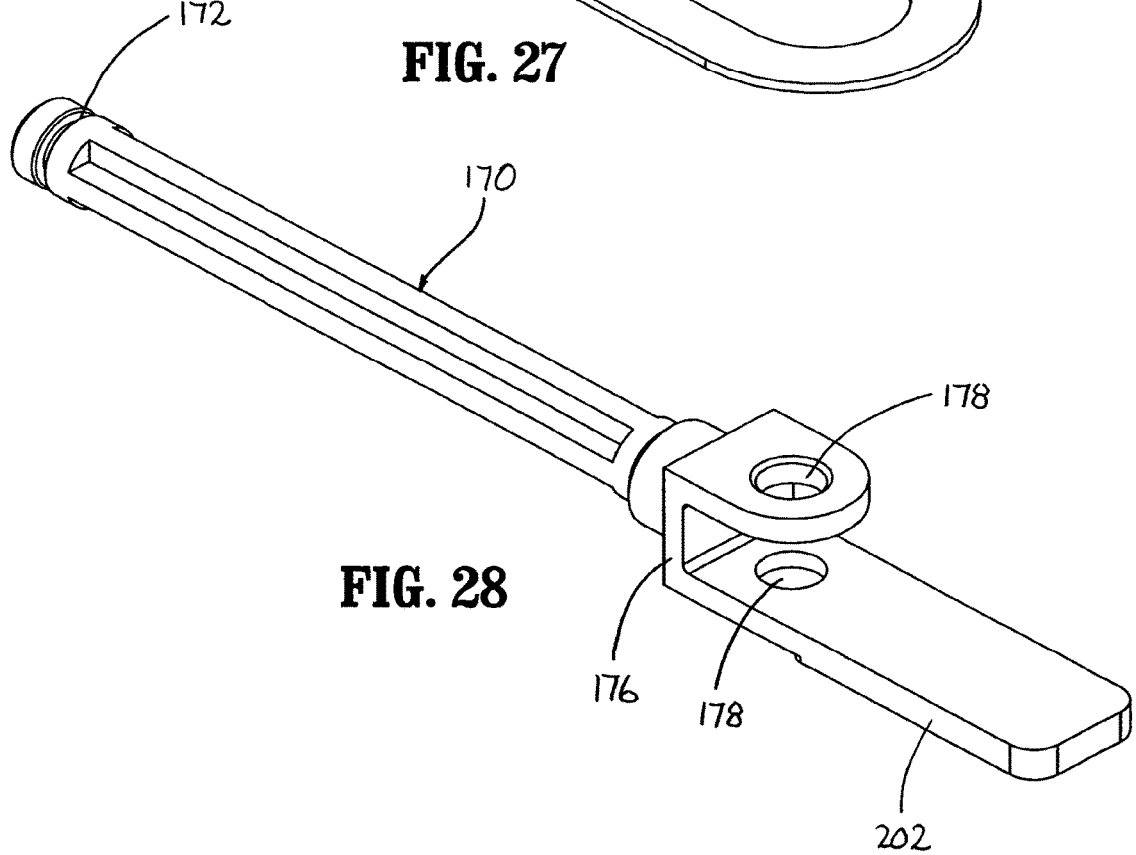
FIG. 28 is a perspective view of the yoke of the handle portion shown in FIG. 25.

Referring to FIGS. 25-27, handle portion 12 includes an anti-reverse ratchet mechanism which includes a pawl 192, a rack 194, and a pawl biasing member 196. Rack 194 includes a series of teeth 194a and is supported within a recess 198 formed in housing half-section 20a. In one embodiment, recess 198 is dovetail shaped and the backside of rack 194 has a dovetail shape projection 194b which is slidably received within recess 198 to secure rack 194 within housing 20. Alternately, other fastening techniques can be used to secure rack 194 within housing 20, e.g., adhesives, pins, welding, etc.

Pawl 192 includes a bore 192a dimensioned to receive pivot member 180 such that pawl 192 is rotatably mounted to yoke 170 about pivot member 180. Pawl biasing member 196 includes a pair of mounting holes 200 for securing bracket 196 to a plate extension 202 (FIG. 28) of yoke 170. Pawl biasing member 196 also includes a semi-circular cutout 204 which is positioned to be clipped partially about pivot member 180, and a cantilever or spring arm 206 which is positioned within a slot 192b formed in a backside of pawl 192. Cantilever arm 206 is resilient and provides a biasing force to urge pawl 192 to a position in which pawl finger 192c is substantially perpendicular to arm 206. Finger 192c is positioned to engage teeth 194a of rack 194 to retain yoke 170 at partially advanced positions during actuation of clip applier 10 against the bias of spring 179 which urges yoke 170 to its retracted position. The anti-reverse ratchet mechanism prevents retraction of yoke 170 and camming member 68 after handles 22 have been partially actuated until the clip applier has been fully actuated.

Figures 36, 37:
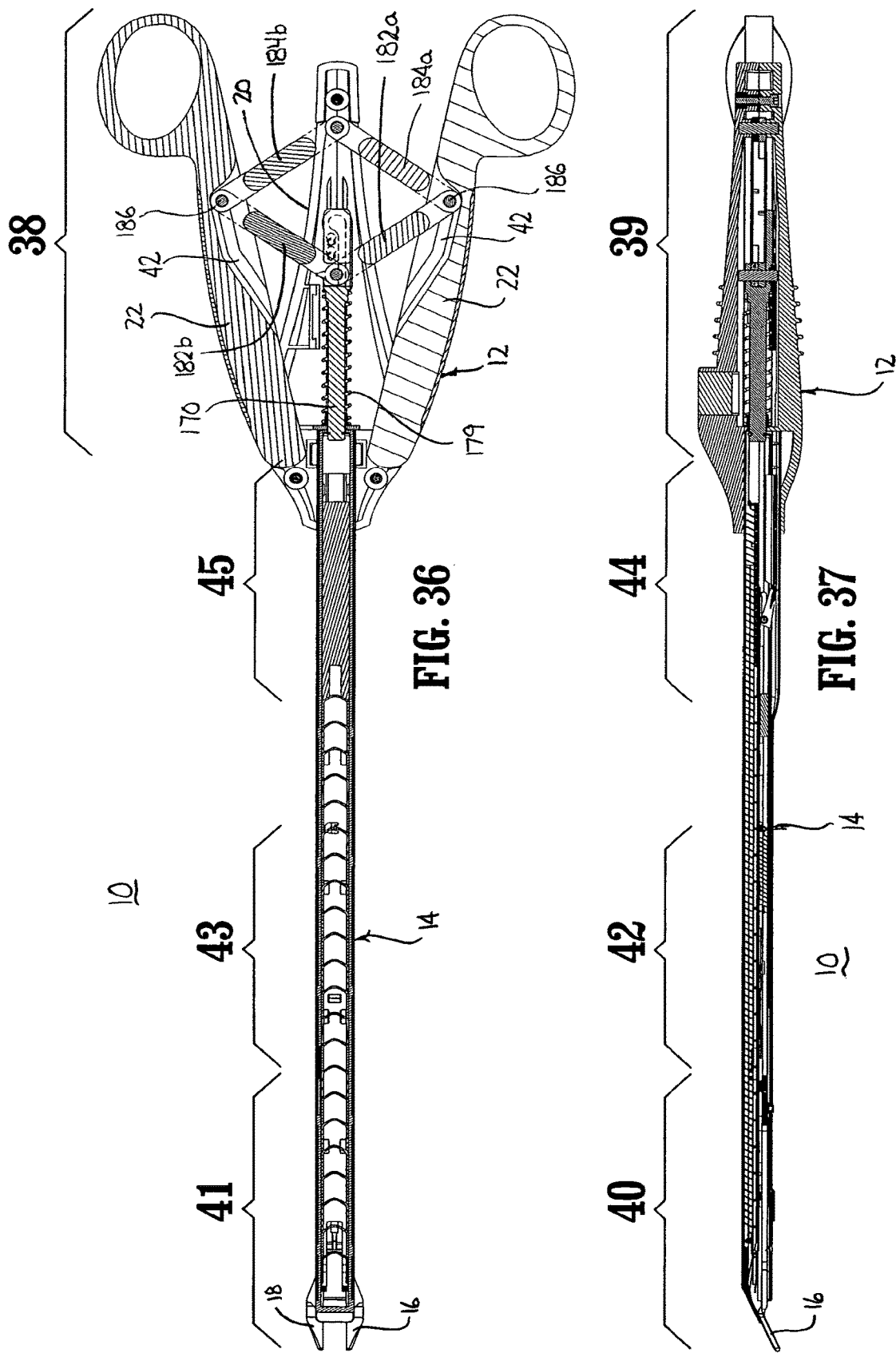
FIG. 36 is a top cross-sectional view of the clip applying apparatus shown in FIG. 1 prior to actuation of the apparatus.
FIG. 37 is a side cross-sectional view of the clip applying apparatus shown in FIG. 36.
Figure 42:
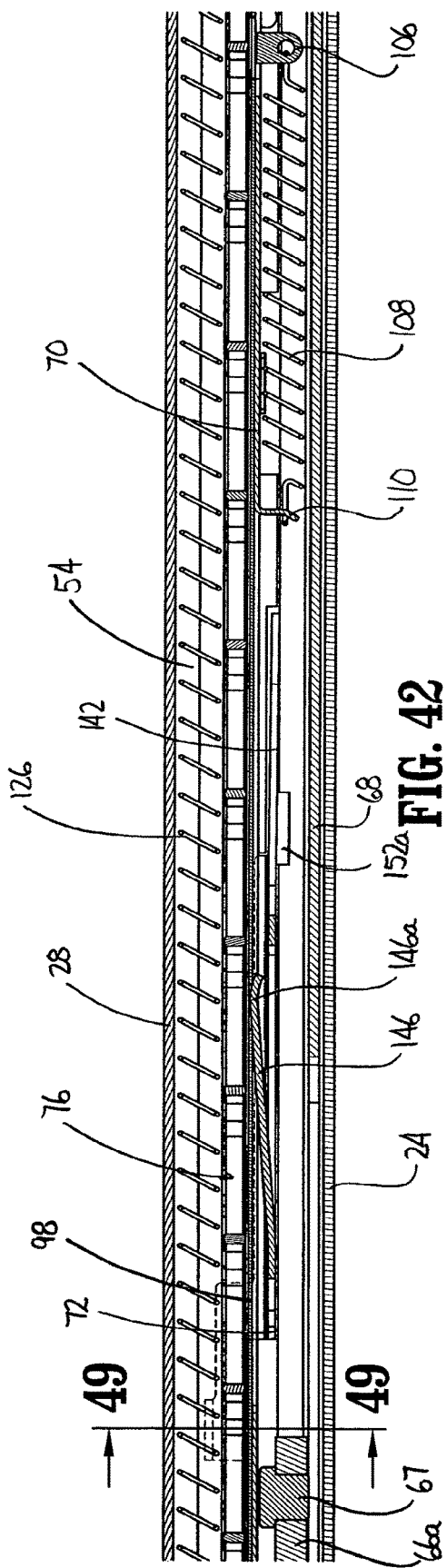
FIG. 42 is an enlarged view of the indicated area of detail shown in FIG. 37.
Figure 43:
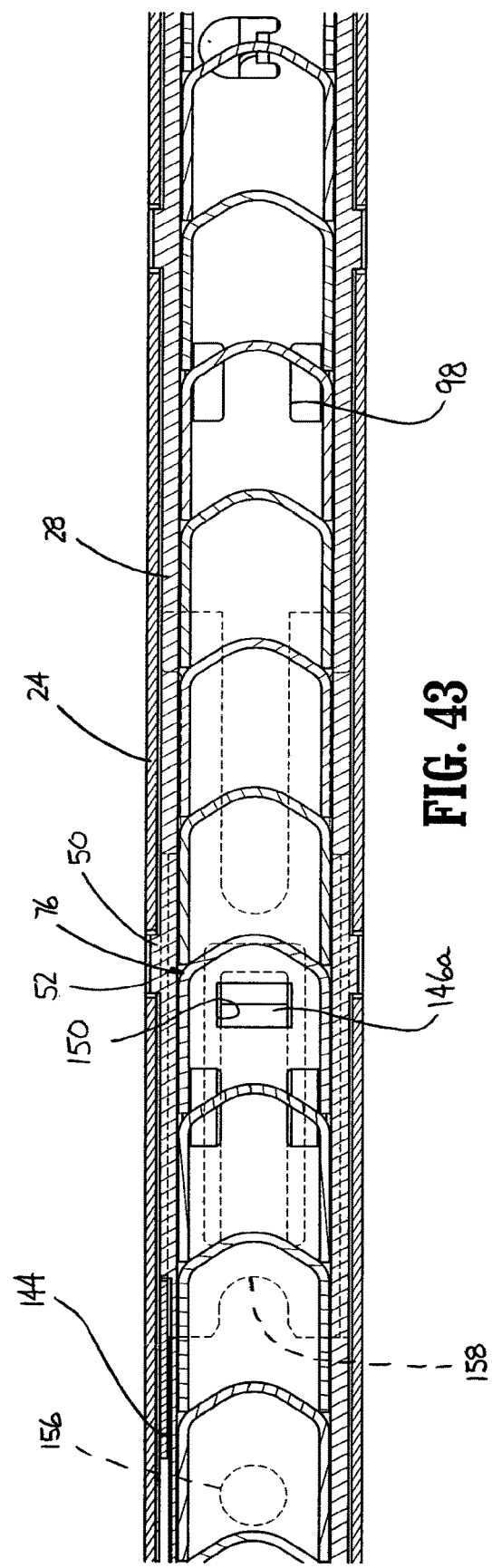
FIG. 43 is an enlarged view of the indicated area of detail shown in FIG. 36.

Referring to FIGS. 36-67, operation of clip applier 10 will now be described. FIGS. 36-50 illustrate clip applier 10 prior to actuation of handles 22, i.e., in the prefired position. In the prefired position, biasing member 179 urges yoke 170 to its retracted position. When yoke 170 is in its retracted position, pivot members 186 are positioned within cam channels 42 (FIG. 36) such that front links 182a and 182b and rear links 184a and 184b are in their misaligned position, handles 22 are spaced from housing 20 of clip applier 10, and pawl 192 (FIG. 38) is positioned proximally of rack 194 (FIG. 38). Referring to FIGS. 40-50, in the prefired position, camming member 68 is urged to its retracted position by yoke 170 and biasing member 179 (FIG. 39). Clip pusher 70 is urged to its retracted position by biasing member 108 (FIG. 42). Clip stack 76 is urged by follower 74 (FIG. 44) and biasing member 126 distally within body 14, but distal-most clip 76a is prevented from moving into jaws 16 and 18 by spring arm 118 of clip stop member 116 (FIG. 40). Jaw locking plate 130 is positioned between jaw legs 66b to prevent inadvertent closure of jaws 16 and 18 (FIG. 40). It is also noted that latch member 94 of pusher latch assembly 80 is spaced distally of but in a position to engage abutment member 79 which is supported on camming member 68 (FIG. 44). Further, radial projections 142a of lockout 72 are positioned proximally of slots 152a of camming member 68 and recess 158 of lockout 72 is positioned proximally of stop member 156.

FIGS. 51-63 illustrate clip applier 10 in various stages of operation. Referring to FIG. 51, handles 22 have been partially actuated or moved towards housing 20 in the direction indicated by arrow "A". Actuation of handles 22 moves front links 182a and 182b towards their aligned position to advance yoke 170 distally in the direction indicated by arrow "B". Referring to FIG. 52, as yoke 170 is advanced, camming member 68 which is secured to yoke 170 is advanced distally within elongated body 14 of clip applier 10. Abutment member 79 is supported on camming member 68 and is also advanced distally within elongated body 14 in the direction indicated by arrow "C". During the initial actuation stroke of handles 22, abutment member 79 engages latch member 94 of pusher latch assembly 80 to effect advancement of clip pusher 70 in the direction indicated by arrow "D". Referring to FIG. 53, as clip pusher 70 advances, engagement finger 84 of clip pusher 70 advances distal-most clip 76a of clip stack 76 past spring arm 118 of clip stop member 116 into jaws 16 and 18. As the distal-most clip 76a of clip stack 76 is advanced into the jaws, follower 74 (FIG. 52) under the force of biasing member 126 advances clip stack 76 distally in the direction indicated by arrow "E" in FIG. 53 to position the second distal-most clip 77 adjacent clip stop member 116 (See FIGS. 53-55).

Referring to FIGS. 55-57, as camming member 68 and clip pusher 70 advance within elongated body 14, the tension in spring 108 is increased, i.e., spring 108 is stretched (FIG. 56). When distal-most clip 76a is fully positioned within jaws 16 and 18, pusher latch cam 110 engages a distal end of latch member 94 and pivots latch member 94 in the direction indicated by arrow "F" against the urging of biasing member 96 to release latch member 94 from abutment member 79. When latch member 94 is released from abutment member 79, biasing member 108 returns clip pusher 70 to its retracted position (FIGS. 58 and 59).

As handles 22 are more fully actuated, i.e., moved closer to housing 20, camming member 68 engages finger 130a of jaw locking plate 130 (FIG. 55) to deform plate 130 downwardly from between legs 66b of jaw body 66. Continued advancement of camming member 68 advances engagement member 72 into camming surfaces 70 of jaws 16 and 18 to move jaws 16 and 18 from a spaced position (FIG. 46) to a crimping position (FIG. 63).

Referring to FIG. 51, as yoke 170 is moved from its retracted position within housing 20 to its advanced position, a finger 192c of pawl 192 engages teeth 194a of rack 194 to prevent spring 179 from returning yoke 170 to its retracted position when handles 22 are released. As such, once handles 22 begin to be actuated and pawl 192 engages rack 194 (FIG. 51) yoke 170 cannot be returned to its retracted position until clip applier 10 is fully actuated. When yoke 170 is moved to its advanced position, pawl 192 passes by the distal end of rack 194 (FIG. 61) and cantilevered or spring arm 206 of pawl biasing member 196 will rotate pawl 192 in the direction indicated by arrow "G" in FIG. 61 to a position in which finger 192a of pawl 192 is positioned at 12:00. Thus, when handles 22 are released and spring 179 returns yoke 170 to its retracted positioned (FIG. 64) finger 192c will engage the distal end of rack 194 and rotate counter-clockwise in the direction indicated by arrow "H" in FIG. 64 and ratchet over teeth 194a of rack 194. Note, in the fully retracted position of yoke 170, pawl 192 is positioned proximally of rack 194. In this position cantilevered arm 206 (FIG. 61) returns finger 192c of pawl 192 to the 12:00 position.

Figure 62:
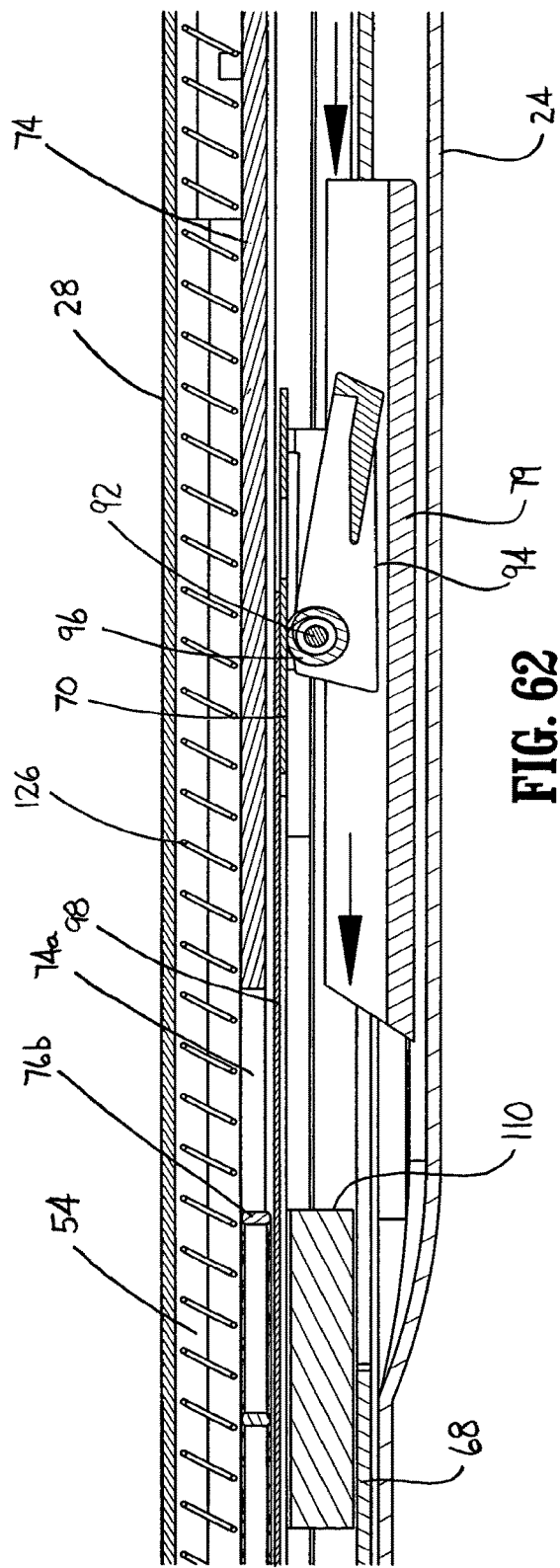
FIG. 62 is a side cross-sectional view of the body portion shown in FIG. 58 after further actuation of the handle portion.
Figure 63:
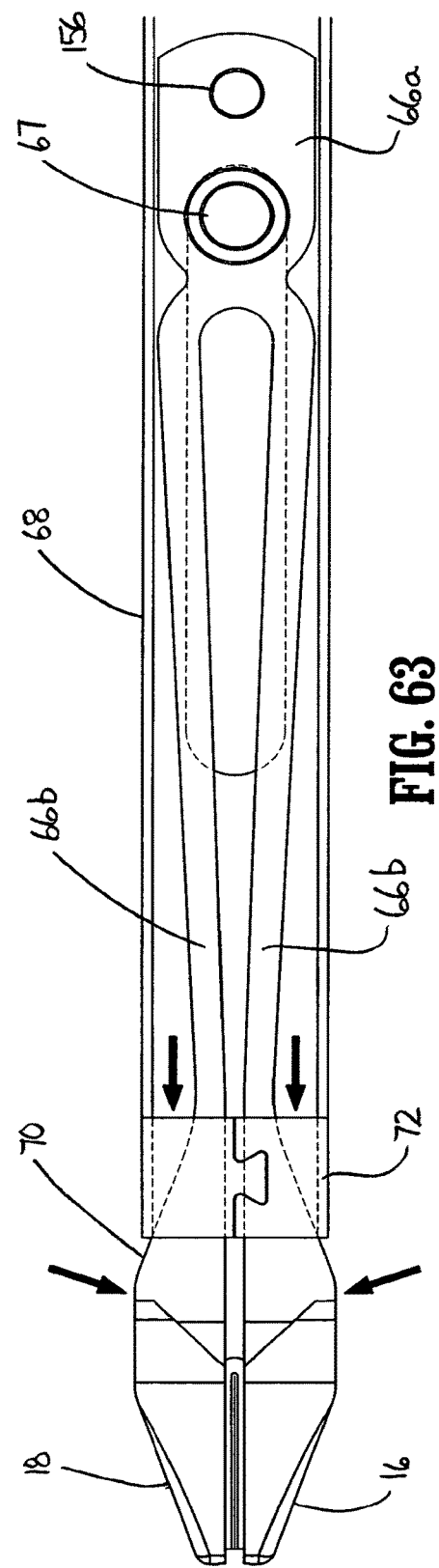
FIG. 63 is a top view of the jaw body and camming member shown in FIG. 60 with camming member fully advanced.
Figure 64:
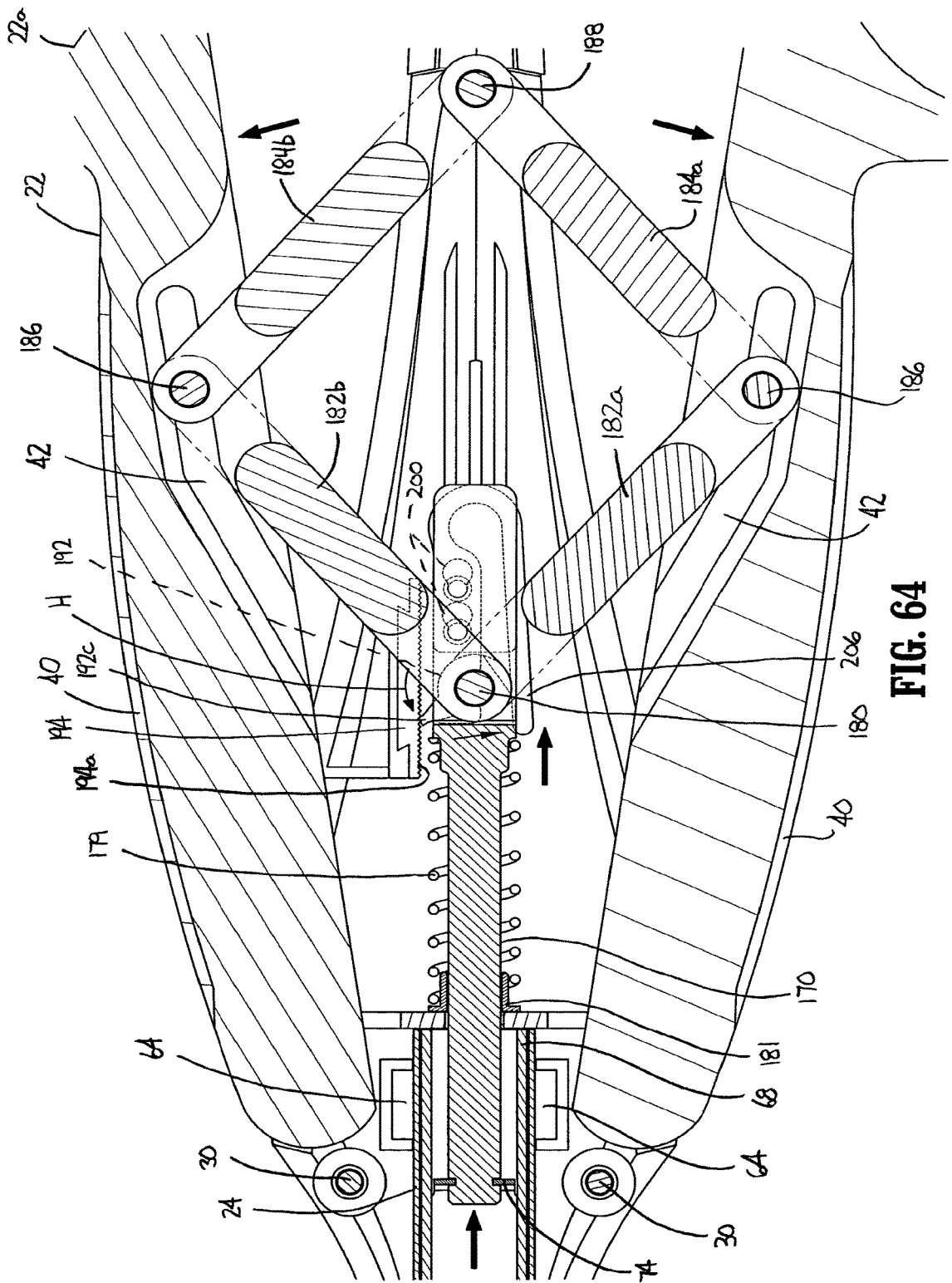
FIG. 64 is a top cross-section view of the handle portion shown in FIG. 61 after the handle portion has been returned to the unactuated position.

After the device has been fully actuated as shown in FIGS. 61-63 and handles 22 have been released, yoke 170 is moved to its retracted position by spring 179. Camming member 68, which is secured to yoke 170, is also moved toward its retracted position. As this occurs, resilient jaws 16 and 18 return to their spaced position and camming member 68 moves past jaw locking plate 130 allowing locking plate finger 130a to return to a position located between legs 66b of jaw body 66. As discussed above, the positioning of locking plate 130 between legs 66b of jaw body 66 prevents inadvertent closure of jaws 16 and 18.

Referring to FIGS. 65 and 66, after the proximal-most clip 76b has been advanced beyond clip stop member 116, clip follower 74 is advanced towards its fully advanced position by biasing member 126. As this occurs, lockout tab 114 formed on follower 74 engages engagement member 144 of lockout 72 to advance lockout 72 distally in relation to camming member 68 to move radial projections 142*a* of flexible legs 142 of lockout 72 into slots 152*a* of camming member 68 and secure or interlock lockout 72 to camming member 68. When lockout 72 is moved distally within elongated body 14 by follower 74, distal recess 158 of lockout 72 receives stop member 156, which is secured to mounting portion 66*a* of jaw body 66 such that the distal end of lockout 72 engages stop member 156. Engagement between the distal end of lockout 72 and stop member 156 prevents further distal movement of lockout 72 and, thus, camming member 68.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. An apparatus for applying surgical clips, comprising:
 a body portion supporting a clip stack, the clip stack including a distal-most clip;
 jaw members;
 a clip pusher supported by the body portion and positioned to advance the distal-most clip between the jaw members;
 a camming member positioned to move along the body portion between a retracted position and an advanced position to selectively approximate the jaw members, the camming member supporting an abutment; wherein the camming member defines a cutout and the abutment is supported within the cutout and
 a latch assembly supported on the clip pusher, the latch assembly including a latch member pivotable relative to the clip pusher between a first position and a second portion to selectively engage the abutment.

2. The apparatus according to claim 1, wherein the latch assembly further includes a biasing member that is configured to urge the latch member away from the clip pusher.

3. The apparatus according to claim 1, further including a latch cam supported on the body portion, the latch cam positioned to engage the latch member after the clip pusher advances the distal-most clip of the clip stack between the jaw members to disengage the latch member from the abutment.

4. The apparatus according to claim 3, wherein the body portion includes a housing body and a housing cover, the latch cam supported on the housing cover.

5. The apparatus according to claim 3, wherein the at least one moveable handle includes a pair of handles, each handle of the pair of handles is operably connected to the yoke by the at least one link.

6. The apparatus according to claim 1, wherein movement of the camming member from the retracted position to the advanced position causes the abutment to engage the latch member to move the latch member and the clip pusher distally.

7. The apparatus according to claim 1, wherein the abutment includes at least one projection that is received within the cutout to secure the abutment to the camming member.

8. The apparatus according to claim 1, wherein the abutment is integrally formed with the camming member.

9. The apparatus of claim 1, further comprising at least one movable handle, wherein the camming member is operably connected to the at least one movable handle such that movement of the at least one movable handle through an actuation stroke effectuates movement of the camming member between the retracted position and the advanced position.

10. The apparatus according to claim 9, further comprising a yoke connected to the camming member, the at least one moveable handle operably connected to the yoke by at least one link such that movement of the at least one moveable handle through an actuation stroke effectuates advancement of the yoke and the camming member.

* * * * *